United States Patent
Woo et al.

(10) Patent No.: US 9,359,354 B2
(45) Date of Patent: *Jun. 7, 2016

(54) KINASE INHIBITORS

(71) Applicant: CHIESI FARMACEUTICI S.p.A., Parma (IT)

(72) Inventors: Chi-Kit Woo, Harlow (GB); Lilian Alcaraz, Harlow (GB); Carmelida Capaldi, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/296,730

(22) Filed: Jun. 5, 2014

(65) Prior Publication Data

US 2014/0364411 A1 Dec. 11, 2014

(30) Foreign Application Priority Data

Jun. 6, 2013 (EP) ..................................... 13170921

(51) Int. Cl.
*A61K 31/44* (2006.01)
*C07D 471/02* (2006.01)
*C07D 471/10* (2006.01)
*C07D 471/04* (2006.01)

(52) U.S. Cl.
CPC ............ *C07D 471/10* (2013.01); *C07D 471/04* (2013.01)

(58) Field of Classification Search
None
See application file for complete search history.

(56) References Cited

U.S. PATENT DOCUMENTS 8,907,094 B2 * 12/2014 Van Niel et al. ............... 546/119
2014/0364412 A1 * 12/2014 Alcaraz et al. ........... 514/210.21

FOREIGN PATENT DOCUMENTS

WO  2007/091152  8/2007
WO  2010/094956  8/2010

OTHER PUBLICATIONS

U.S. Appl. No. 14/513,663, filed Oct. 14, 2014, Van Niel, et al.
European Search Report in Application No. 13170921.4 issued Sep. 5, 2013.
U.S. Appl. No. 14/296,794, filed Jun. 5, 2014, Alcaraz, et al.
U.S. Appl. No. 14/330,145, filed Jul. 14, 2014, Van Niel, et al.
U.S. Appl. No. 14/451,600, filed Aug. 5, 2014, Van Niel, et al.

* cited by examiner

*Primary Examiner* — Heidi Reese
(74) *Attorney, Agent, or Firm* — Oblon, McClelland, Maier & Neustadt, L.L.P.

(57) ABSTRACT

Compounds of formula (I) described herein are p38 MAPK inhibitors and are useful as anti-inflammatory agents in the treatment of, inter alia, diseases of the respiratory tract.

6 Claims, No Drawings

KINASE INHIBITORS

CROSS REFERENCES TO RELATED APPLICATIONS

This application claims priority to European Patent Application No. 1,317,0921.4 filed on Jun. 6, 2013, which is incorporated herein by reference in its entirety.

BACKGROUND OF THE INVENTION

1. Field of the Invention

This invention relates to compounds and compositions that are p38 MAPK inhibitors, and which are useful as anti-inflammatory agents in the treatment of, inter alia, diseases of the respiratory tract.

2. Discussion of the Background

Mitogen activated protein kinases (MAPK) constitute a family of proline-directed serine/threonine kinases that activate their substrates by dual phosphorylation. There are four known human isoforms of p38 MAP kinase, p38α, p38β, p38γ and p38δ. The p38 kinases, which are also known as cytokine suppressive anti-inflammatory drug binding proteins (CSBP), stress activated protein kinases (SAPK) and RK, are responsible for phosphorylating (Stein et al., Ann. Rep. Med Chem., 1996, 31, 289-298, which is incorporated herein by reference in its entirety) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (Herlaar E. & Brown Z., Molecular Medicine Today, 1999, 5, 439-447, which is incorporated herein by reference in its entirety). The products of p38 phosphorylation have been shown to mediate the production of inflammatory cytokines, including tumor necrosis factor alpha (TNF α) and interleukin-(IL)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (e.g. Dinarello et al., Rev. Infect. Disease, 1984, 6, 51, which is incorporated herein by reference in its entirety). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (Badger et al., J. Pharm. Exp. Thera., 1996, 279, 1453-1461; Griswold et al, Pharmacol. Comm., 1996, 7, 323-229, which are incorporated herein by reference in their entireties). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α, IL-1β, IL-6, IL-4, IL-5, and IL-13 (Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288, which are incorporated herein by reference in their entireiesy). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (Lee et al., Immunopharmacology, 2000, 47, 185-200, which is incorporated herein by reference in its entirety). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425, which is incorporated herein by reference in its entirety). It is believed that the compounds of the present invention can be used to treat p38 mediated diseases such as: chronic obstructive pulmonary disease (COPD), asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemangiomas, angiofibroma of the nasopharynx, and avascular necrosis of bone, benign and malignant tumors/neoplasia including cancer, leukaemia, lymphoma, systemic lupus erythematosus (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6

(HHV-6), human herpesvirus-7 (HHV7), human herpesvirus-8 (HHV-8), pseudorabies and rhinotracheitis, among others.

Known P38 kinase inhibitors have been reviewed by G. J. Hanson (Expert Opinions on Therapeutic Patents, 1997, 7, 729-733) J Hynes et al. (Current Topics in Medicinal Chemistry, 2005, 5, 967-985), C. Dominguez et al (Expert Opinions on Therapeutics Patents, 2005, 15, 801-816) and L. H. Pettus & R. P. Wurtz (Current Topics in Medicinal Chemistry, 2008, 8, 1452-1467), which are incorporated herein by reference in their entireties. P38 kinase inhibitors containing a triazolopyridine motif are known in the art, for example WO07/091152, WO04/072072, and WO06/018727, which are incorporated herein by reference in their entireties.

International Patent Application WO2010/094956, which is incorporated herein by reference in its entirety, discloses triazolopyridine derivatives of formula (I) as being p38 MAP Kinase inhibitors:

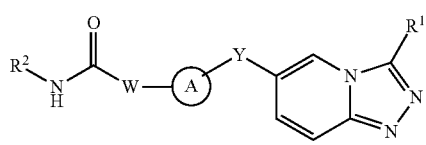

(I)

In such compounds, A represents an optionally substituted divalent arylene radical, an heteroarylene radical, a ($C_5$-$C_6$) divalent cycloalkylene radical having 5 or 6 ring atoms or a pyperidinylene radical.

Other p38 MAP Kinase inhibitors are described in the co-pending applications PCT/EP2011/072375, PCT/EP2012/074446, and PCT/EP2012/074450, which are incorporated herein by reference in their entireties. The compounds are said to be useful in as anti-inflammatory agents in the treatment of diseases of the respiratory tract.

However, a need remains for p38 mitogen activated protein kinase inhibitors which are useful in the treatment of inflammatory and obstructive diseases of the respiratory tract.

SUMMARY OF THE INVENTION

Accordingly, it is one object of the present invention to provide novel and potent p38 mitogen activated protein kinase inhibitors which are useful in the treatment of inflammatory and obstructive diseases of the respiratory tract.

It is another object of the present invention, to identify novel potent p38 mitogen activated protein kinase inhibitors which show an appropriate developability profile on inhalatory administration to effectively treat respiratory obstructive or inflammatory diseases. It is to be understood that such profile may be achieved in a number of different ways by modulation of specific properties; by way of example, it could be achieved by administration of a low effective dose of the drug thus limiting side effects or via a long duration of action in the lungs which may reduce the frequency of administration.

It is another object of the present invention to provide novel pharmaceutical compositions which contain such a p38 mitogen activated protein kinase inhibitor.

It is another object of the present invention to provide novel methods of treating certain diseases and conditions by administering such a p38 mitogen activated protein kinase inhibitor.

These and other objects, which will become apparent during the following detailed description, have been achieved by the inventors' discovery of the compounds of formula (I) described below.

The compounds of the present invention are inhibitors of p38 mitogen activated protein kinase ("p38 MAPK", "p38 kinase" or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

DETAILED DESCRIPTION OF THE PREFERRED EMBODIMENTS

According to one aspect of the invention, there is provided a compound of formula (I), or a pharmaceutically acceptable salt thereof:

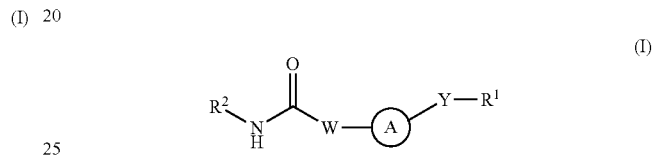

(I)

wherein:

W is a heteroatom selected from N or O, wherein N is substituted with —H, $C_1$-$C_6$ alkyl, or $C_3$-$C_5$ cycloalkyl;

Y is selected in the group consisting of: a group —S(O)$_p$— wherein p is 0, 1 or 2; a group —O(CR$^3$R$^4$)$_n$—; a group —(CR$^5$R$^6$)$_n$—; a group —NR$^7$—; a group —OC(O)—; a group —OC(O)NH—; and a group —OC(O)O—;

n is 0, 1, 2 or 3;

R$^3$, R$^4$, R$^5$ and R$^6$ are each independently —H, fluorine or $C_1$-$C_6$ alkyl, or, respectively, R$^3$ and R$^4$, or R$^5$ and R$^6$ may form together with the carbon atom to which they are attached a saturated 3-6 membered carbocyclic monocyclic ring optionally substituted by a group $C_1$-$C_6$ alkyl, hydroxyl or halo;

R$^7$ is —H, $C_1$-$C_6$ alkyl, or $C_3$-$C_7$ cycloalkyl wherein such $C_1$-$C_6$ alkyl or $C_3$-$C_7$ cycloalkyl are optionally substituted by a group $C_1$-$C_3$ alkyl, $C_3$-$C_6$ cycloalkyl, hydroxyl, —CN or halo;

R$^1$ is a group (IIa)

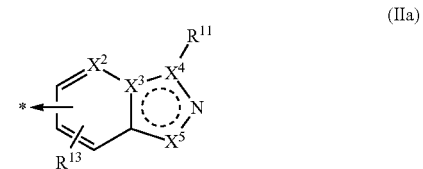

(IIa)

X$^2$, X$^3$, X$^4$ and X$^5$ are each independently a carbon atom, a nitrogen atom, a group —(CH)— or a group —NH—; such that each combination thereof forms an aromatic ring system;

R$^{11}$ is linked to X$^4$ and is selected from a group consisting of:

—NR$^A$R$^B$, —N(R$^C$)($C_2$-$C_6$alkylene)-NR$^A$R$^B$, —N(R$^C$)($C_3$-$C_7$cycloalkylene)-NR$^A$R$^B$, —($C_1$-$C_6$alkylene)-NR$^A$R$^B$, —($C_3$-$C_7$cycloalkylene)-NR$^A$R$^B$, —O—($C_2$-$C_6$alkylene)-NR$^A$R$^B$, —O—($C_3$-$C_7$cycloalkylene)-NR$^A$R$^B$, —S—($C_2$-$C_6$alkylene)-NR$^A$R$^B$, —S—($C_3$-$C_7$cycloalkylene)-NR$^A$R$^B$, —N(R$^C$)C(O)—($C_1$-$C_6$alkylene)-NR$^A$R$^B$, —N(R$^C$)C(O)—($C_3$-$C_7$cycloalkylene)-NR$^A$R$^B$, —C(O)N(R$^C$)—($C_2$-

$C_6$alkylene)-$NR^AR^B$, —C(O)N($R^C$)—($C_3$-$C_7$cycloalkylene)-$NR^AR^B$, —C(O)N($R^C$)—($C_2$-$C_6$alkylene)-$OR^D$, —C(O)N($R^C$)—($C_3$-$C_7$cycloalkylene)-$OR^D$, —N($R^C$)C(O)N($R^AR^B$), —C(O)N($R^AR^B$), —N($R^C$)C(O)N($R^C$)—($C_2$-$C_6$alkylene)-$NR^AR^B$, —N($R^C$)C(O)N($R^C$)—($C_3$-$C_7$cycloalkylene)-$NR^AR^B$, —O—($C_2$-$C_6$alkylene)-$OR^D$, —O—($C_3$-$C_7$cycloalkylene)-$OR^D$, —S—($C_2$-$C_6$alkylene)-$OR^D$, —S—($C_3$-$C_7$cycloalkylene)-$OR^D$, —N($R^C$)S(O)$_2$—($C_1$-$C_6$alkylene)-$NR^AR^B$, —N($R^C$)S(O)$_2$—($C_3$-$C_7$cycloalkylene)-$NR^AR^B$, —S(O)$_2$N($R^C$)—($C_2$-$C_6$alkylene)-$NR^AR^B$, —S(O)$_2$N($R^C$)—($C_3$-$C_7$cycloalkylene)-$NR^AR^B$, —S(O)$_2$N($R^C$)—($C_2$-$C_6$alkylene)-$OR^D$, —S(O)$_2$N($R^C$)—($C_3$-$C_7$cycloalkylene)-$OR^D$, —N($R^C$)S(O)$_2$—($C_2$-$C_6$alkylene)-$OR^D$, —N($R^C$)S(O)$_2$($C_3$-$C_7$cycloalkylene)-$OR^D$, —S(O)$_2$N($R^AR^B$), —N($R^C$)S(O)$_2R^D$, —N($R^C$)C(O)$R^C$, $OR^C$, $SR^C$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl) and ($C_3$-$C_7$heterocycloalkyl)carbonyl, wherein any of such $C_1$-$C_6$alkyl, $C_3$-$C_6$cycloalkyl, —($C_1$-$C_6$alkylene)- —($C_2$-$C_6$alkylene)-, —($C_3$-$C_7$cycloalkylene)-, —($C_3$-$C_7$heterocycloalkyl) and ($C_5$-$C_7$heterocycloalkyl) portion in the above listed groups may be optionally substituted by one, two or three groups $R^{25}$ which are independently selected in the list consisting of: $C_1$-$C_6$ alkyl, ($C_1$-$C_3$) haloalkyl, ($C_1$-$C_4$) hydroxyalkyl, $C_3$-$C_7$ cycloalkyl, hydroxyl and halo; or $R^{11}$ is linked to $X^4$ and is phenyl or 5- or 6-membered monocyclic heteroaryl, wherein such phenyl or 5- or 6-membered monocyclic heteroaryl is optionally substituted by one or more group(s) independently selected from: halo, $OR^D$, —CN, —SO$_2R^D$, $C_1$-$C_6$ alkyl which is substituted by one or more groups —CN; $C_3$-$C_6$ cycloalkyl which is substituted by a group selected from:

—CN, —$OR^C$, —$SR^C$ or halo; —N($R^C$)($C_2$-$C_6$alkylene)-$NR^AR^B$, —N($R^C$)($C_3$-$C_7$cycloalkylene)-$NR^AR^B$, —($C_1$-$C_6$alkylene)-$NR^AR^B$, —($C_3$-$C_7$cycloalkylene)-$NR^AR^B$, —O—($C_3$-$C_7$cycloalkylene)-$NR^AR^B$, —S—($C_2$-$C_6$alkylene)-$NR^AR^B$, —S—($C_3$-$C_7$cycloalkylene)-$NR^AR^B$, —N($R^C$)C(O)—($C_1$-$C_6$alkylene)-$NR^AR^B$, —N($R^C$)C(O)—($C_3$-$C_7$cycloalkylene)-$NR^AR^B$, —C(O)N($R^C$)—($C_2$-$C_6$alkylene)-$NR^AR^B$, —C(O)N($R^C$)—($C_3$-$C_7$cycloalkylene)-$NR^AR^B$, —C(O)N($R^C$)—($C_2$-$C_6$alkylene)-$OR^D$, —C(O)N($R^C$)—($C_3$-$C_7$cycloalkylene)-$OR^D$, —N($R^C$)C(O)N($R^C$)—($C_2$-$C_6$alkylene)-$NR^AR^B$, —N($R^C$)C(O)N($R^C$)—($C_3$-$C_7$cycloalkylene)-$NR^AR^B$, —O—($C_3$-$C_7$cycloalkylene)-$OR^D$, —S—($C_3$-$C_7$cycloalkylene)-$OR^D$, —N($R^C$)S(O)$_2$—($C_1$-$C_6$alkylene)-$NR^AR^B$, —N($R^C$)S(O)$_2$—($C_3$-$C_7$cycloalkylene)-$NR^AR^B$, —S(O)$_2$N($R^C$)—($C_2$-$C_6$alkylene)-$NR^AR^B$, —S(O)$_2$N($R^C$)—($C_3$-$C_7$cycloalkylene)-$NR^AR^B$, —S(O)$_2$N($R^C$)—($C_2$-$C_6$alkylene)-$OR^D$, —S(O)$_2$N($R^C$)—($C_3$-$C_7$cycloalkylene)-$OR^D$, —N($R^C$)S(O)$_2$—($C_2$-$C_6$alkylene)-$OR^D$, —N($R^C$)S(O)$_2$—($C_3$-$C_7$cycloalkylene)-$OR^D$, —N($R^C$)S(O)$_2R^D$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl) and ($C_3$-$C_7$heterocycloalkyl)carbonyl, wherein any of such $C_1$-$C_6$alkyl, $C_3$-$C_6$cycloalkyl, —($C_1$-$C_6$alkylene)- —($C_2$-$C_6$alkylene)-, —($C_3$-$C_7$cycloalkylene)-, —($C_3$-$C_7$heterocycloalkyl) and —($C_5$-$C_7$heterocycloalkyl) portion in the above listed groups may be optionally substituted by one, two or three groups $R^{25}$ which are independently selected in the group consisting of: $C_1$-$C_6$alkyl, ($C_1$-$C_3$) haloalkyl, ($C_1$-$C_4$)hydroxyalkyl, $C_3$-$C_7$cycloalkyl, hydroxyl, —CN and halo;

$R^A$ and $R^B$ are at each occurrence independently —H, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$ cycloalkyl, —$OR^D$, —CN, —$NR^{A'}R^{B'}$ or halo; alternatively, $R^A$ and $R^B$, may form together with the nitrogen atom to which they are attached an azetidine or a 4-11-membered saturated heterocyclic monocyclic or bicyclic ring system which is optionally substituted by one or more groups independently selected from —$OR^D$, —CN, —$NR^{A'}R^{B'}$, halo, $C_1$-$C_6$ alkyl, —($C_3$-$C_7$)cycloalkyl-$NR^{A'}R^{B'}$, —($C_1$-$C_5$alkylene)-$NR^{A'}R^{B'}$, —O—($C_1$-$C_5$ alkylene)-$NR^{A'}R^{B'}$ and —O—($C_3$-$C_7$cycloalkyl)-$NR^{A'}R^{B'}$, —N($R^C$)C(O)—($C_1$-$C_6$alkylene)-$NR^{A'}R^{B'}$, —N($R^C$)C(O)—($C_3$-$C_7$cycloalkylene)-$NR^{A'}R^{B'}$, —C(O)N($R^C$)—($C_2$-$C_6$alkylene)-$NR^{A'}R^{B'}$, —C(O)N($R^C$)—($C_3$-$C_7$cycloalkylene)-$NR^{A'}R^{B'}$ such $C_1$-$C_6$ alkyl, $C_2$-$C_5$ alkyl and $C_3$-$C_7$ cycloalkyl portions being optionally substituted by a group $C_1$-$C_3$ alkyl, $C_3$-$C_7$cycloalkyl, —$OR^D$, —CN, —$NR^{A'}R^{B'}$ or halo; and which 6-11-membered saturated heterocyclic monocyclic or bicyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^D$, —CN, or halo; or $R^A$ and $R^B$ may be linked to one carbon atom of the —($C_1$-$C_6$alkylene)- or —($C_3$-$C_7$cycloalkylene)-portion of the group linked to the nitrogen to which they are connected to form a saturated cycle of up to 6 ring atoms;

$R^C$ is at each occurrence independently —H, $C_1$-$C_6$ alkyl, ($C_1$-$C_4$)hydroxyalkyl or $C_3$-$C_6$ cycloalkyl, such $C_1$-$C_6$ alkyl, ($C_1$-$C_4$)hydroxyalkyl and $C_3$-$C_6$ cycloalkyl being optionally substituted by a group $C_1$-$C_3$ alkyl, —$OR^D$, —CN or halo;

alternatively $R^C$ may be linked to one carbon atom of the —($C_2$-$C_6$alkylene)- or —($C_3$-$C_7$cycloalkylene)-portion of the group linked to the nitrogen to which they are connected to form a saturated cycle of up to 6 ring atoms;

$R^D$ is at each occurrence independently —H, —CH$_3$, —C$_2$H$_5$ or ($C_1$-$C_4$)hydroxyalkyl;

$R^{A'}$ and $R^{B'}$ are at each occurrence independently —H, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$ cycloalkyl, —$OR^{D'}$, —CN or halo; alternatively, $R^{A'}$ and $R^{B'}$, may form together with the nitrogen atom to which they are attached a 4-11-membered saturated heterocyclic monocyclic or bicyclic ring system which is optionally substituted by one or more group —$OR^D$, —CN, halo, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^{D'}$, —CN or halo; and which 6-11-membered saturated heterocyclic monocyclic or bicyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^{D'}$, —CN, or halo; or $R^{A'}$ and $R^{B'}$ may be linked to one carbon atom of the —($C_1$-$C_6$alkylene)- or —($C_3$-$C_7$cycloalkylene)-portion of the group linked to the nitrogen to which they are connected to form a saturated cycle of up to 6 ring atoms;

$R^{D'}$ is at each occurrence independently —H, —CH$_3$ or —C$_2$H$_5$;

$R^{C'}$ is at each occurrence independently —H, $C_1$-$C_6$ alkyl or $C_3$-$C_6$ cycloalkyl, such $C_1$-$C_6$ alkyl and $C_3$-$C_6$ cycloalkyl being optionally substituted by a group $C_1$-$C_3$ alkyl, —$OR^{D'}$, —CN or halo;

$R^{13}$ are independently —H, $C_1$-$C_6$ alkyl or halo;

A is a divalent cycloalkylene radical having 5, 6 or 7 ring atoms; said cycloalkylene ring being attached to W and Y, and optionally fused to a phenyl ring or to a monocyclic heteroaryl ring having 5 or 6 ring atoms, such phenyl or heteroaryl ring being optionally substituted by one or two groups $R^{24}$;

$R^{24}$ is at each occurrence independently selected from the group consisting of $C_1$-$C_6$ alkyl, halo and CN;

$R^2$ is a radical of formula (IIIa)

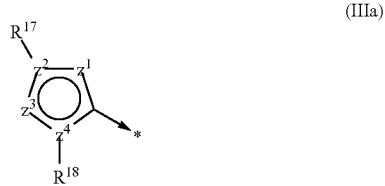

(IIIa)

$R^{17}$ is a group of general formula (IV):

(IV)

$R^{19}$ is selected from the group consisting of: —H, —$CH_3$, CN and OH; $R^{20}$ is selected from the group consisting of: —H, —F, —$CH_3$, —$C_2H_5$, —$CH_2OH$, —$CH_2OMe$, —$CF_2CF_3$, —$CH_2SCH_3$, —$SCH_3$ and —$SC_2H_5$; $R^{21}$ is —H, —$CH_3$ or —$C_2H_5$;

$R^{18}$ is absent or is selected from the group consisting of aryl, heteroaryl, —($C_1$-$C_6$alkyl), —($C_3$-$C_7$cycloalkyl), —($C_3$-$C_7$heterocycloalkyl), ($C_5$-$C_7$heterocycloalkyl)-($C_1$-$C_6$alkyl) and ($C_5$-$C_7$heterocycloalkyl)-($C_3$-$C_6$ cycloalkyl), wherein any of such aryl, heteroaryl, —($C_1$-$C_6$alkyl), —($C_3$-$C_7$cycloalkyl), —($C_3$-$C_7$heterocycloalkyl), ($C_5$-$C_7$heterocycloalkyl)-($C_1$-$C_6$alkyl) and ($C_5$-$C_7$heterocycloalkyl)-($C_3$-$C_6$ cycloalkyl) may be optionally substituted by one or more group(s) selected from —CN, —OH, =O, halo, —$COOR^M$, $C_1$-$C_6$alkyl, $C_3$-$C_6$cycloalkyl, —O—($C_1$-$C_6$alkyl), —O—($C_3$-$C_6$cycloalkyl), —$SO_2R^M$; —S—($C_1$-$C_6$alkyl), —S—($C_3$-$C_6$cycloalkyl), —$NR^HR^J$, —N($R^L$)($C_2$-$C_6$alkylene)-$NR^HR^J$, —N($R^L$)($C_3$-$C_7$cycloalkylene)-$NR^HR^J$, —($C_1$-$C_6$alkylene)-$NR^HR^J$, —($C_3$-$C_7$cycloalkylene)-$NR^HR^J$, —O—($C_2$-$C_6$alkylene)-$NR^HR^J$, —O—($C_3$-$C_7$cycloalkylene)-$NR^HR^J$, —S—($C_2$-$C_6$alkylene)-$NR^HR^J$, —S—($C_3$-$C_7$cycloalkylene)-$NR^HR^J$, —N($R^L$)C(O)—($C_1$-$C_6$alkylene)-$NR^HR^J$, —N($R^L$)C(O)—($C_3$-$C_7$cycloalkylene)-$NR^HR^J$, —C(O)N($R^L$)—($C_2$-$C_6$alkylene)-$NR^HR^J$, —C(O)N($R^L$)—($C_3$-$C_7$cycloalkylene)-$NR^HR^J$, —N($R^L$)C(O)N($R^HR^J$), —C(O)N($R^HR^J$), —N($R^L$)C(O)N($R^L$)—($C_2$-$C_6$alkylene)-$NR^HR^J$, —N($R^L$)C(O)N($R^L$)—($C_3$-$C_7$cycloalkylene)-$NR^HR^J$, —N($R^L$)S(O)$_2$—($C_1$-$C_6$alkylene)-$NR^HR^J$, —N($R^L$)S(O)$_2$—($C_3$-$C_7$cycloalkylene)-$NR^HR^J$, —S(O)$_2$N($R^L$)—($C_2$-$C_6$alkylene)-$NR^HR^J$, —S(O)$_2$N($R^L$)—($C_3$-$C_7$cycloalkylene)-$NR^HR^J$, —S(O)$_2$N($R^HR^J$), $OR^L$, $SR^L$ wherein any of such $C_1$-$C_6$alkyl, $C_3$-$C_6$cycloalkyl, —($C_1$-$C_6$alkylene)-, —($C_2$-$C_6$alkylene)-, —($C_3$-$C_7$cycloalkylene)-, —($C_3$-$C_7$heterocycloalkyl) and ($C_5$-$C_7$heterocycloalkyl) portion in the above listed groups, may be optionally substituted by a group $C_1$-$C_6$ alkyl, $C_3$-$C_7$ cycloalkyl, —$OR^L$ or halo;

$R^H$ and $R^J$, are at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN or halo; alternatively, $R^H$ and $R^J$ may form together with the nitrogen atom to which they are attached an azetidine or a 4-11 membered saturated monocyclic or bicyclic heterocyclic ring system which is optionally substituted by one or more groups —$OR^M$, —CN, halo, $NR^OR^P$, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^M$, —CN or halo; and which 6-11-membered saturated monocyclic or bicyclic heterocyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^M$, —CN, or halo;

$R^L$ is at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN or halo;

$R^M$ is at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group hydroxyl, —CN or halo;

$R^O$ and $R^P$ are each independently $C_1$-$C_6$ alkyl or $C_1$-$C_6$ cycloalkyl, optionally substituted by a group $C_1$-$C_3$ alkyl, —$OR^Q$, —CN or halo; alternatively, $R^O$ and $R^P$ may form together with the nitrogen atom to which they are attached a 4-8-membered saturated monocyclic heterocyclic ring system which is optionally substituted by one or more groups —$OR^Q$, —CN, halo, $C_1$-$C_6$ alkyl or $C_3$-$C_7$ cycloalkyl, and which 6-8-membered saturated monocyclic heterocyclic ring optionally contains a further heteroatom which is oxygen or nitrogen, said nitrogen atom optionally substituted by $C_1$-$C_6$ alkyl or $C_3$-$C_6$ cycloalkyl;

$R^Q$ is —H, —$CH_3$ or —$C_2H_5$;

$z^1$, $z^2$, $z^3$, and $z^4$ are independently selected in the group consisting of: C, N, S, O, a group —CH—, and a group —NH—, in such a combination that the resulting ring formed is an aromatic system;

with the proviso that when there is any combination among any of the substituents of $R^{19}$ selected in a group consisting of —$CH_3$ and $R^{20}$ selected from the group consisting of —F, —$CH_3$, —$C_2H_5$, —$CH_2OH$, —$CH_2OMe$, —$CF_2CF_3$, —$CH_2SCH_3$, —$SCH_3$ and —$SC_2H_5$ and $R^{21}$ selected from —$CH_3$ and —$C_2H_5$;

and

A is a divalent cycloalkylene radical having 5, 6 or 7 ring atoms fused to a phenyl ring or monocyclic heteroaryl, then —$R^{11}$ is —$NR^AR^B$, —N($R^C$)($C_2$-$C_6$alkylene)-$NR^AR^B$, —N($R^C$)($C_3$-$C_7$cycloalkylene)-$NR^AR^B$, —($C_1$-$C_6$alkylene)-$NR^AR^B$, —($C_3$-$C_7$cycloalkylene)-$NR^AR^B$, —O—($C_2$-$C_6$alkylene)-$NR^AR^B$, —O—($C_3$-$C_7$cycloalkylene)-$NR^AR^B$, —S—($C_2$-$C_6$alkylene)-$NR^AR^B$, —S—($C_3$-$C_7$cycloalkylene)-$NR^AR^B$, —N($R^C$)C(O)—($C_1$-$C_6$alkylene)-$NR^AR^B$, —N($R^C$)C(O)—($C_3$-$C_7$cycloalkylene)-$NR^AR^B$, —C(O)N($R^C$)—($C_2$-$C_6$alkylene)-$NR^AR^B$, —C(O)N($R^C$)—($C_3$-$C_7$cycloalkylene)-$NR^AR^B$, —N($R^C$)C(O)N($R^AR^B$), —C(O)N($R^AR^B$), —N($R^C$)C(O)N($R^C$)—($C_2$-$C_6$alkylene)-$NR^AR^B$, —N($R^C$)C(O)N($R^C$)—($C_3$-$C_7$cycloalkylene)-$NR^AR^B$, —N($R^C$)S(O)$_2$—($C_1$-$C_6$alkylene)-$NR^AR^B$, —N($R^C$)S(O)$_2$—($C_3$-$C_7$cycloalkylene)-$NR^AR^B$, —S(O)$_2$N($R^C$)—($C_2$-$C_6$alkylene)-$NR^AR^B$, —S(O)$_2$N($R^C$)—($C_3$-$C_7$cycloalkylene)-$NR^AR^B$, —S(O)$_2$N($R^AR^B$), wherein any of such ($C_1$-$C_6$alkylene)-, —($C_2$-$C_6$alkylene)-, —($C_3$-

$C_7$cycloalkylene)- and —($C_3$-$C_7$heterocycloalkyl) portion in the above listed groups may be optionally substituted by one, two or three groups $R^{25}$ which are independently selected in the list consisting of:
$C_1$-$C_6$ alkyl, ($C_1$-$C_3$) haloalkyl, ($C_1$-$C_4$)hydroxyalkyl, $C_3$-$C_7$ cycloalkyl, hydroxyl and halo; wherein $R^A$ and $R^B$ are at each occurrence independently form together with the nitrogen atom to which they are attached a azetidine or a 4-11-membered saturated heterocyclic monocyclic or bicyclic ring system which is substituted by —$NR^{A'}R^{B'}$, —($C_1$-$C_5$alkylene)-$NR^{A'}R^{B'}$, —O—($C_1$-$C_5$alkyl)-$NR^{A'}R^{B'}$, —O—($C_3$-$C_7$cycloalkyl)-$NR^{A'}R^{B'}$, —N($R^C$)C(O)—($C_1$-$C_6$alkylene)-$NR^{A'}R^{B'}$, —N($R^{C'}$)C(O)—($C_3$-$C_7$cycloalkylene)-$NR^{A'}R^{B'}$, —C(O)N($R^{C'}$)—($C_2$-$C_6$alkylene)-$NR^{A'}R^{B'}$, —C(O)N($R^{C'}$)—($C_3$-$C_7$cycloalkylene)-$NR^{A'}R^{B'}$ and optionally by one or more group selected from —$OR^D$, —CN, halo, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^D$, —CN, —$NR^{A'}R^{B'}$ or halo; and which 6-11-membered saturated heterocyclic monocyclic or bicyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^D$, —CN, or halo;

or $R^{11}$ is linked to $X^4$ and is phenyl or 5- or 6-membered monocyclic heteroaryl, wherein such phenyl or 5- or 6-membered monocyclic heteroaryl is substituted by two or more group(s) selected from: —N($R^C$)($C_2$-$C_6$alkylene)-$NR^AR^B$, —N($R^C$)($C_3$-$C_7$cycloalkylene)-$NR^AR^B$, —($C_1$-$C_6$alkylene)-$NR^AR^B$, —($C_3$-$C_7$cycloalkylene)-$NR^AR^B$, —O—($C_3$-$C_7$cycloalkylene)-$NR^AR^B$, —S—($C_2$-$C_6$alkylene)-$NR^AR^B$, —S—($C_3$-$C_7$cycloalkylene)-$NR^AR^B$, —N($R^C$)C(O)—($C_1$-$C_6$alkylene)-$NR^AR^B$, —N($R^C$)C(O)—($C_3$-$C_7$cycloalkylene)-$NR^AR^B$, —C(O)N($R^C$)—($C_2$-$C_6$alkylene)-$NR^AR^B$, —C(O)N($R^C$)—($C_3$-$C_7$cycloalkylene)-$NR^AR^B$, —C(O)N($R^C$)—($C_2$-$C_6$alkylene)-$OR^D$, —C(O)N($R^C$)—($C_3$-$C_7$cycloalkylene)-$OR^D$, —N($R^C$)C(O)N($R^C$)—($C_2$-$C_6$alkylene)-$NR^AR^B$, —N($R^C$)C(O)N($R^C$)—($C_3$-$C_7$cycloalkylene)-$NR^AR^B$, —O—($C_3$-$C_7$cycloalkylene)-$OR^D$, —S—($C_3$-$C_7$cycloalkylene)-$OR^D$, —N($R^C$)S(O)$_2$—($C_1$-$C_6$alkylene)-$NR^AR^B$, —N($R^C$)S(O)$_2$—($C_3$-$C_7$cycloalkylene)-$NR^AR^B$, —S(O)$_2$N($R^C$)—($C_2$-$C_6$alkylene)-$NR^AR^B$, —S(O)$_2$N($R^C$)—($C_3$-$C_7$cycloalkylene)-$NR^AR^B$; and additionally optionally substituted by one or more group(s) selected from: $C_1$-$C_6$ alkyl, $C_3$-$C_6$ cycloalkyl, halo, —$OR^D$, —CN, $SO_2R^D$, —$CONR^AR^B$ wherein any of such $C_1$-$C_6$alkyl, $C_3$-$C_6$cycloalkyl, —($C_1$-$C_6$alkylene)-, —($C_2$-$C_6$alkylene)-, —($C_3$-$C_7$cycloalkylene)- and —($C_3$-$C_7$heterocycloalkyl) portion in the above listed groups may be optionally substituted by one, two or three groups $R^{25}$ which are independently selected in the group consisting of: $C_1$-$C_6$alkyl, ($C_1$-$C_3$) haloalkyl, ($C_1$-$C_4$)hydroxyalkyl, $C_3$-$C_7$cycloalkyl, hydroxyl, CN and halo;

wherein $R^A$ and $R^B$ are at each occurrence independently hydrogen, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^{D'}$, —CN, —$NR^{A'}R^{B'}$ or halo; alternatively, $R^A$ and $R^B$, may form together with the nitrogen atom to which they are attached a 4-11-membered saturated heterocyclic monocyclic or bicyclic ring system which is optionally substituted by one or more group —$OR^{D'}$, —CN, —$NR^{A'}R^{B'}$, halo, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^{D'}$, —CN or halo; and which 6-11-membered saturated heterocyclic monocyclic or bicyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^{D'}$, —CN, or halo; and/or $R^A$ and $R^B$ may be linked to one carbon atom of the —($C_1$-$C_6$alkylene)-, —($C_2$-$C_6$alkylene)- or —($C_3$-$C_7$cycloalkylene)-portion of the group linked to the nitrogen to which they are connected to form a saturated cycle of up to 6 ring atoms;

or

—$R^{18}$ is selected in the group consisting of aryl, heteroaryl, —($C_1$-$C_6$alkyl), —($C_3$-$C_7$cycloalkyl), —($C_3$-$C_7$heterocycloalkyl), ($C_5$-$C_7$heterocycloalkyl)-($C_1$-$C_6$alkyl) and ($C_5$-$C_7$heterocycloalkyl)-($C_3$-$C_6$ cycloalkyl), wherein any of such aryl, heteroaryl, —($C_1$-$C_6$alkyl), —($C_3$-$C_7$cycloalkyl), —($C_3$-$C_7$heterocycloalkyl), ($C_5$-$C_7$heterocycloalkyl)-($C_1$-$C_6$alkyl) and ($C_5$-$C_7$heterocycloalkyl)-($C_3$-$C_6$ cycloalkyl) is substituted by a group selected from $NR^HR^J$, —N($R^L$)($C_2$-$C_6$alkylene)-$NR^HR^J$, —N($R^L$)($C_3$-$C_7$cycloalkylene)-$NR^HR^J$, —($C_1$-$C_6$alkylene)-$NR^HR^J$, —($C_3$-$C_7$cycloalkylene)-$NR^HR^J$, —O—($C_2$-$C_6$alkylene)-$NR^HR^J$, —O—($C_3$-$C_7$cycloalkylene)-$NR^HR^J$, —S—($C_2$-$C_6$alkylene)-$NR^HR^J$, —S—($C_3$-$C_7$cycloalkylene)-$NR^HR^J$, —N($R^L$)C(O)—($C_1$-$C_6$alkylene)-$NR^HR^J$, —N($R^L$)C(O)—($C_3$-$C_7$cycloalkylene)-$NR^HR^J$, —C(O)N($R^L$)—($C_2$-$C_6$alkylene)-$NR^HR^J$, —C(O)N($R^L$)—($C_3$-$C_7$cycloalkylene)-$NR^HR^J$, —N($R^L$)C(O)N($R^HR^J$), —C(O)N($R^HR^J$), —N($R^L$)C(O)N($R^L$)—($C_2$-$C_6$alkylene)-$NR^HR^J$, —N($R^L$)C(O)N($R^L$)—($C_3$-$C_7$cycloalkylene)-$NR^HR^J$, —N($R^L$)S(O)$_2$—($C_1$-$C_6$alkylene)-$NR^HR^J$, —N($R^L$)S(O)$_2$—($C_3$-$C_7$cycloalkylene)-$NR^HR^J$, —S(O)$_2$N($R^L$)—($C_2$-$C_6$alkylene)-$NR^HR^J$, —S(O)$_2$N($R^L$)—($C_3$-$C_7$cycloalkylene)-$NR^HR^J$, and wherein any portion in the above listed groups may be optionally substituted by a group $C_1$-$C_6$ alkyl, $C_3$-$C_7$ cycloalkyl, —$OR^L$ or halo; and wherein $R^H$ and $R^J$ at each occurrence independently form together with the nitrogen atom to which they are attached an azetidine or a 4-11 membered saturated monocyclic or bicyclic heterocyclic ring system which is substituted by $NR^OR^P$ and optionally by one or more additional groups —$OR^M$, —CN, halo, $C_1$-$C_6$ alkyl or $C_3$-$C_7$ cycloalkyl, such $C_1$-$C_6$alkyl and $C_3$-$C_7$ cycloalkyl being optionally substituted by a group $C_1$-$C_3$ alkyl, $C_3$-$C_7$cycloalkyl, —$OR^M$, CN or halo; and which 6-11-membered saturated monocyclic or bicyclic heterocyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^M$, CN, or halo;

wherein $R^{A'}$, $R^{B'}$, $R^C$, $R^{C'}$, $R^D$, $R^{D'}$, $R^H$, $R^J$, $R^L$, $R^M$, $R^O$ and $R^P$ are as defined above.

In another aspect, the present invention provides pharmaceutical compositions comprising a compound of the present invention, together with one or more pharmaceutically acceptable carriers and/or excipients. Particularly preferred are compositions adapted for inhalation for pulmonary administration.

In another aspect, the present invention provides the use of a compound of the invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, bronchiectasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

Terminology

As used herein, the terms "halogen" or "halo" include fluorine, chlorine, bromine and iodine atoms.

As used herein, the term "$C_x$-$C_y$alkyl" wherein x and y are integers, refers to a straight or branched chain alkyl radical having from x to y carbon atoms. Thus when x is 1 and y is 6, for example, the term includes methyl, ethyl, n-propyl, iso-propyl, n-butyl, isobutyl, sec-butyl, t-butyl, n-pentyl, and n-hexyl.

As used herein, the term "$C_x$-$C_y$haloalkyl" refers to the above "$C_x$-$C_y$alkyl" group wherein one or more hydrogen atoms are replaced by one or more halogen atoms.

As used herein, the term "$C_x$-$C_y$hydroxyalkyl" refers to the above "$C_x$-$C_y$alkyl" group wherein one hydrogen atom is replaced by one hydroxyl group.

As used herein, the term "$C_x$-$C_y$alkylene" wherein x and y are integers, refers to a $C_x$-$C_y$alkyl radical having in total two unsatisfied valencies, such as a divalent methylene radical.

As used herein, the term "carbocyclic" refers to a mono-, bi- or tricyclic radical having up to 16 ring atoms, all of which are carbon, and includes aryl and cycloalkyl.

As used herein, the term "$C_z$-$C_k$cycloalkyl" wherein z and k are integers refers to a monocyclic saturated carbocyclic radical having from z to k carbon atoms and includes, for example, cyclopropyl, cyclobutyl, cyclopentyl, cyclohexyl, cycloheptyl and cyclooctyl. Comprised within the scope of the term "$C_z$-$C_k$cycloalkyl", are those radicals having two unsatisfied valencies on the same carbon atom which will link to any $C_x$-$C_y$alkyl, $C_x$-$C_y$alkylene $C_z$-$C_k$cycloalkyl $C_z$-$C_k$cycloalkylene, $C_z$-$C_k$heterocycloalkyl, $C_z$-$C_k$heterocycloalkyl$C_x$-$C_y$alkyl, $C_z$-$C_k$heterocycloalkyl$C_z$-$C_k$cycloalkyl or ($C_z$-$C_k$)heterocycloalkylcarbonyl group by replacement of two hydrogen atoms placed on the same carbon. In such circumstances, this radical forms a gem-disubstituted or Spiro system together with the $C_x$-$C_y$alkyl, $C_x$-$C_y$alkylene $C_z$-$C_k$cycloalkyl $C_z$-$C_k$cycloalkylene, $C_z$-$C_k$heterocycloalkyl, $C_z$-$C_k$heterocycloalkyl$C_x$-$C_y$alkyl, $C_z$-$C_k$heterocycloalkyl$C_z$-$C_k$cycloalkyl or ($C_z$-$C_k$)heterocycloalkylcarbonyl group it is linked to.

The term "$C_z$-$C_k$cycloalkylene radical" refers to a $C_z$-$C_k$cycloalkyl radical having two unsatisfied valencies on different cycle carbon atoms as follows:

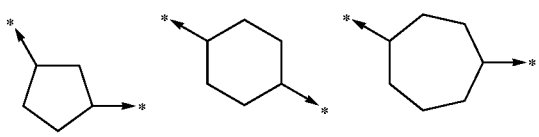

As used herein, the unqualified term "aryl" refers to a mono- or bi-cyclic carbocyclic aromatic radical, and includes radicals having two monocyclic carbocyclic aromatic rings which are directly linked by a covalent bond. Illustrative of such radicals are phenyl, biphenyl and naphthyl.

As used herein, the unqualified term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are fused through a common bond. Illustrative examples of 5,6-membered heteroaryl are: are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, and triazinyl. Illustrative examples of 8,10-membered heteroaryl are: benzothienyl, benzofuryl, benzimidazolyl, benzothiazolyl, benzisothiazolyl, benzoxazolyl, benzisoxazolyl, benzotriazolyl, indolyl and indazolyl.

As used herein, the unqualified term "heterocyclyl" or "heterocyclic" and relates to a saturated mono-, bi- or tricyclic non-aromatic radical containing one or more heteroatoms selected from S, N and O. In the case of bicyclic heterocyclic systems, included within the scope of the term are fused, Spiro and bridged bicyclic systems. In particular, the term "$C_z$-$C_k$heterocycloalkyl" refers to monocyclic ($C_z$-$C_k$) cycloalkyl groups, in which at least one ring carbon atom is replaced by a heteroatom (e.g. N, NH, S or O). Examples of ($C_z$-$C_k$)heterocycloalkyl include pyridonyl, pyrrolidinyl, thiazolidinyl, piperazinyl, piperidinyl, morpholinyl, and thiomorpholinyl.

By analogy, the term "$C_z$-$C_k$heterocycloalkylene", refers to a divalent $C_z$-$C_k$heterocycloalkyl radical, wherein $C_z$-$C_k$heterocycloalkyl is as above defined.

The term "$C_z$-$C_k$heterocycloalkyl$C_x$-$C_y$alkyl" refers to the above "$C_x$-$C_y$alkyl" group wherein one or more hydrogen atoms are replaced by one or more "$C_z$-$C_k$heterocycloalkyl" groups. Comprised within the scope of the term "$C_z$-$C_k$heterocycloalkyl$C_x$-$C_y$alkyl" are systems where two hydrogen atoms linked to the same carbon atom in "$C_x$-$C_y$alkyl" group are replaced by one "$C_z$-$C_k$heterocycloalkyl" group. Such radical thus form a gem-disubstituted "$C_z$-$C_k$heterocycloalkyl$C_x$-$C_y$alkyl" system, such as a 1,2-dimethyl-pyrrolidin-2-yl radical.

The term "$C_z$-$C_k$heterocycloalkyl$C_z$-$C_k$cycloalkyl" refers to the above "$C_z$-$C_k$cycloalkyl" group wherein one or more hydrogen atoms are replaced by one or more "$C_z$-$C_k$heterocycloalkyl" groups.

The expression "($C_z$-$C_k$)cycloalkylcarbonyl" refers to ($C_z$-$C_k$)cycloalkyl-CO— groups wherein the group "($C_z$-$C_k$)cycloalkyl" has the meaning above defined.

The expression "($C_z$-$C_k$)heterocycloalkylcarbonyl" refers to ($C_z$-$C_k$)heterocycloalkyl-CO— groups wherein the group "($C_z$-$C_k$)heterocycloalkyl" has the meaning above defined.

Compounds of the invention may exist in one or more geometrical, optical, enantiomeric, diastereomeric and tautomeric forms, including but not limited to cis- and trans-forms, E- and Z-forms, R-, S- and meso-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis). Throughout the specification the use of an asterisk "*" in the definition of a structural formula, indicates the point of attachment for the radical group to the rest of the molecule.

As used herein the term "salt" includes base addition, acid addition and ammonium salts. As briefly mentioned above compounds of the invention which are acidic can form salts, including pharmaceutically acceptable salts, with bases such as alkaline metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, formic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds (I) which have a basic nitrogen can also form quaternary ammonium salts with a pharmaceutically acceptable counter-ion such as ammonium, chloride, bromide, acetate, formate, p-toluenesulfonate, succinate, hemi-succinate, naphthalene-bis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002), which is incorporated herein by reference in its entirety.

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in several polymorphic forms and may be obtained in different crystal or co-crystal habits, and they are intended to be included within the meaning of the term "compounds of the invention".

The compounds may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, 3$^{rd}$ Edition, 2002, Taylor and Francis), which are incorporated herein by reference in their entireties.

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985), which is incorporated herein by reference in its entirety. Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

It is to be understood that all preferred groups or embodiments described herebelow for compounds of formula (I) may be combined among each other and apply as well to compounds of formula (Ia), (Ib), (Ic), (IA), (IB), (IC), (ID) or (IE) as below defined mutatis mutandis.

It is also to be understood that the proviso above described for compounds of formula (I) should be applied mutatis mutandis to all the preferred groups or embodiments described herebelow.

In one embodiment, compounds of formula (Ia) are provided, which are compounds of formula (I) as above defined wherein carbon stereogenic center on the cycloalkylene portion of ring A which is linked to group W and identified with number (1) herebelow, possess the absolute configuration herebelow represented:

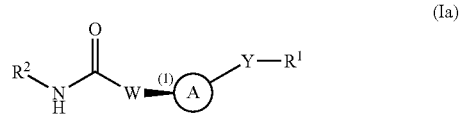

(Ia)

In another embodiment, compounds of formula (Ib) are provided, which are compounds of formula (I) as above defined wherein carbon stereogenic center on the cycloalkylene portion of ring A which are linked to group W and Y and identified, respectively, with numbers (1) and (2) herebelow, possess the absolute configuration herebelow represented:

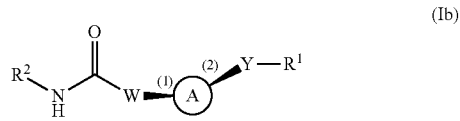

(Ib)

In a further embodiment, compound of formula (Ic) are provided, which are compounds of formula (I) as above defined wherein carbon stereogenic center on the cycloalkylene portion of ring A which are linked to group W and Y and identified, respectively, with numbers (1) and (2) herebelow, possess the absolute configuration herebelow represented:

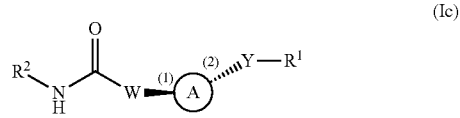

(Ic)

In one embodiment W is NH or O. In a further embodiment, W is NH.

In one embodiment Y is a group —S(O)$_p$—, a group —O(CR$^3$R$^4$)$_n$—, a group —(CR$^5$R$^6$)$_n$—, or a group —NR$^7$—; p is zero and n is 0, 1 or 2. In another embodiment, Y is a group —S(O)$_p$— or a group —O(CR$^3$R$^4$)$_n$ or; p is zero and n is 0 or 1.

In a further embodiment Y is a group —O(CR$^3$R$^4$)$_n$— and n is 0.

In one embodiment R$^3$, R$^4$, R$^5$ and R$^6$ are each independently —H, fluorine or C$_1$-C$_6$ alkyl. In another embodiment, R$^3$, R$^4$, R$^5$ and R$^6$ are —H.

In one embodiment $R^7$ is —H, $C_1$-$C_6$ alkyl, or $C_3$-$C_7$ cycloalkyl.

In one embodiment $R^7$ is —H.

In one embodiment A is a divalent cycloalkylene radical having 5, 6 or 7 ring atoms; said cycloalkylene ring being attached to W and Y, and optionally fused to a phenyl ring or to a monocyclic heteroaryl ring having 5 or 6 ring atoms, such phenyl or heteroaryl ring being optionally substituted by one or two groups $R^{24}$.

In a further embodiment, A is group selected in the group consisting of:

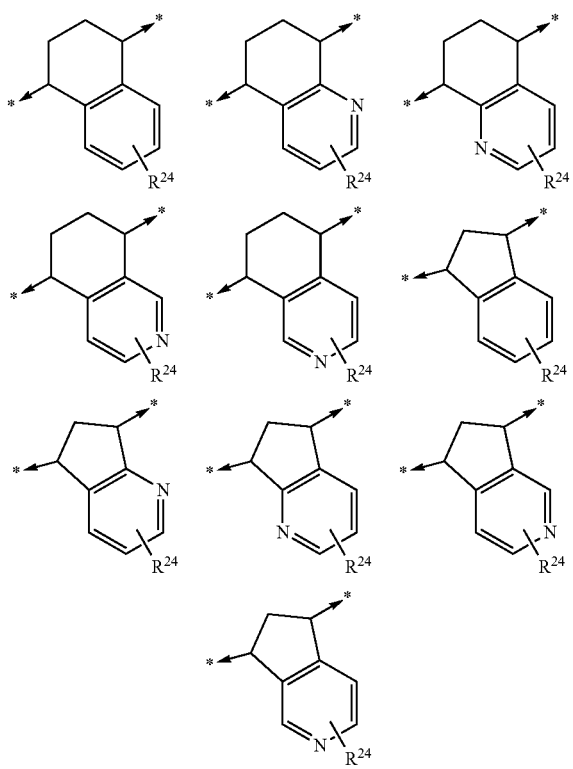

In a further embodiment, A is group

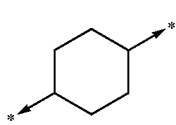

In a still further embodiment, A is group

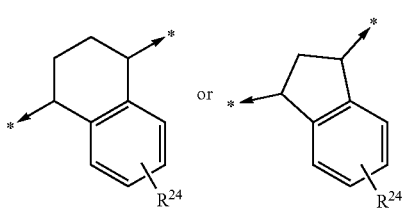

In an additional embodiment, A is group

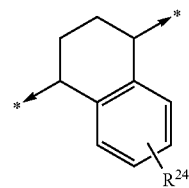

In one embodiment $R^{24}$ is not present or, if present, is independently selected from the group consisting of $C_1$-$C_2$ alkyl, —F, —Cl and —CN; in a further embodiment, $R^{24}$ is not present or, if present, is at each occurrence independently methyl or —F. In a further embodiment, $R^{24}$ is not present.

In a further embodiment, $R^1$ is a group of formula (IIa)

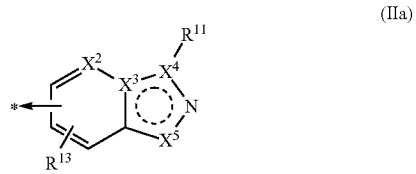

(IIa)

In one embodiment, the group (IIa) is a group of formula (IIaa) or (IIab) which is connected to the group Y through one of the carbons as below indicated

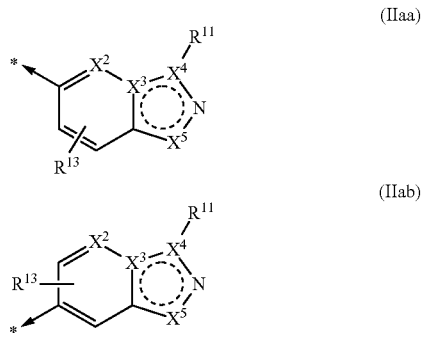

(IIaa)

(IIab)

In another embodiment, the group (IIa) is a group of formula (IIaa) as above defined which is connected to the group Y through the carbon adjacent to $X_2$

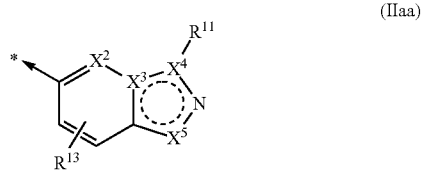

(IIaa)

In one embodiment, $X^4$ is a carbon atom.
In one embodiment, $X^5$ is a nitrogen atom.
In another embodiment, $X^4$ is a carbon atom, $X^5$ is a nitrogen atom, $X^3$ is a nitrogen atom and $X^2$ is nitrogen.
In another embodiment, $X^4$ is a carbon atom, $X^5$ is a nitrogen atom, $X^3$ is a nitrogen atom and $X^2$ is group —CH—.

In another embodiment, $X^4$ is a nitrogen atom, $X^5$ is a group —CH— atom, $X^3$ is a carbon atom and $X^2$ is group —CH—.

In one embodiment, $R^{13}$ is —H, $C_1$-$C_6$ alkyl or halo.

In a further embodiment, the group (IIa) is a group of formula (IIaa) as above defined which is connected to the group Y through the carbon adjacent to $X_2$

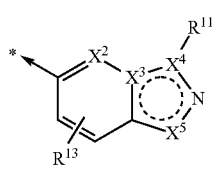

(IIaa)

and wherein $X^4$ is a carbon atom, $X^5$ is a nitrogen atom, $X^3$ is a nitrogen atom and $X^2$ is a group —CH—, and $R^{13}$ is —H.

In one embodiment $R^{11}$ is selected from a group consisting of —$NR^AR^B$, —$N(R^C)(C_2$-$C_6$alkylene)-$NR^AR^B$, —$N(R^C)$($C_3$-$C_7$cycloalkylene)-$NR^AR^B$, —($C_1$-$C_6$alkylene)-$NR^AR^B$, —($C_3$-$C_7$cycloalkylene)-$NR^AR^B$, —O—($C_2$-$C_6$alkylene)-$NR^AR^B$, —O—($C_3$-$C_7$cycloalkylene)-$NR^AR^B$, $OR^C$ and —($C_3$-$C_7$heterocycloalkyl), wherein any of such —($C_1$-$C_6$alkylene)- —($C_2$-$C_6$alkylene)-, —($C_3$-$C_7$cycloalkylene)- portion in the above listed groups may be optionally substituted by one, two or three groups $R^{25}$ which are independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo.

In one embodiment $R^{11}$ is a group

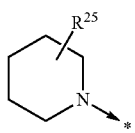

wherein $R^{25}$ is optionally present and represents one, two or three substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$.

In a further embodiment, $R^{11}$ is a group

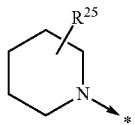

wherein $R^{25}$ represents one, two or three substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$.

In a further embodiment, $R^{11}$ is a group

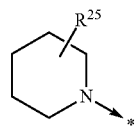

wherein $R^{25}$ represents one or two $C_1$-$C_6$ alkyl substituents; and wherein the asterisk represents the point of attachment for group $R^{11}$ to the rest of the molecule via $X^4$.

In a further embodiment, $R^{11}$ is a group

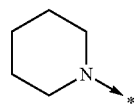

wherein the asterisk represents the point of attachment for group $R^{11}$ to the rest of the molecule via $X^4$.

In a further embodiment, $R^{11}$ is a group

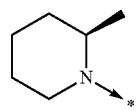

wherein the asterisk represents the point of attachment for group $R^{11}$ to the rest of the molecule via $X^4$.

In a still further embodiment, $R^{11}$ is a group

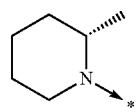

wherein the asterisk represents the point of attachment for group $R^{11}$ to the rest of the molecule via $X^4$.

In another embodiment $R^{11}$ is phenyl which is optionally substituted by one or more group(s) selected from halo, $C_1$-$C_6$ alkyl which is substituted by one or more group(s) —CN; —($C_1$-$C_6$alkylene)-$NR^AR^B$, wherein $R^A$ and $R^B$ may form together with the nitrogen atom to which they are attached a 4-11-membered saturated heterocyclic monocyclic ring system which is optionally substituted by one or more groups selected from —$OR^D$, —CN, —$NR^CR^D$, halo, $C_1$-$C_6$ alkyl or $C_3$-$C_7$ cycloalkyl; and which 6-11-membered saturated heterocyclic monocyclic ring optionally contains a further heteroatom which is oxygen or nitrogen, said nitrogen atom optionally substituted by $C_1$-$C_6$ alkyl or $C_3$-$C_6$ cycloalkyl.

In one embodiment $R^{25}$ is one, two or three groups independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo.

In another embodiment $R^A$ and $R^B$ form together with the nitrogen atom to which they are attached an azetidine or a 4-11-membered saturated heterocyclic monocyclic or bicyclic ring system which is optionally substituted by one or more groups independently selected from —$OR^D$, —CN, —$NR^{A'}R^{B'}$, halo, $C_1$-$C_6$ alkyl, —($C_3$-$C_7$)cycloalkyl-$NR^{A'}R^{B'}$, —(C$_1$-C$_5$ alkylene)-NR$^{A'}$R$^{B'}$, —O—(C$_1$-C$_5$alkylene)-NR$^{A'}$R$^{B'}$ and —O—(C$_3$-C$_7$cycloalkyl)-NR$^{A'}$R$^{B'}$, —N(R$^C$)C(O)—(C$_1$-C$_6$alkylene)-NR$^{A'}$R$^{B'}$, —N(R$^{C'}$)C(O)—(C$_3$-C$_7$cycloalkylene)-NR$^{A'}$R$^{B'}$, —C(O)N(R$^{C'}$)—(C$_2$-C$_6$alkylene)-NR$^{A'}$R$^{B'}$, —C(O)N(R$^{C'}$)—(C$_3$-C$_7$cycloalkylene)-NR$^{A'}$R$^{B'}$ such C$_1$-C$_6$ alkyl, C$_2$-C$_5$ alkyl and C$_3$-C$_7$ cycloalkyl portions being optionally substituted by a group C$_1$-C$_3$ alkyl, C$_3$-C$_7$cycloalkyl, —OR$^D$, —CN, —NR$^{A'}$R$^{B'}$ or halo; and which 6-11-membered saturated heterocyclic monocyclic or bicyclic ring optionally contains a further heteroatom which is oxygen or nitrogen, said nitrogen atom optionally substituted by C$_1$-C$_6$ alkyl or C$_3$-C$_6$ cycloalkyl, wherein any of such C$_1$-C$_6$ alkyl or C$_3$-C$_6$ cycloalkyl may be optionally substituted by a group C$_1$-C$_6$ alkyl, C$_3$-C$_7$ cycloalkyl, —OR$^D$, —CN, or halo; or R$^A$ and R$^B$ may be linked to one carbon atom of the —(C$_1$-C$_6$alkylene)- or —(C$_3$-C$_7$cycloalkylene)-portion of the group linked to the nitrogen to which they are connected to form a saturated cycle of up to 6 ring atoms.

In another embodiment R$^A$ and R$^B$ form together with the nitrogen atom to which they are attached an azetidine or a 4-11-membered saturated heterocyclic monocyclic ring system which is optionally substituted by one or more groups independently selected from C$_1$-C$_6$ alkyl, —(C$_1$-C$_5$ alkylene)-NR$^{A'}$R$^{B'}$ and —O—(C$_1$-C$_5$ alkylene)-NR$^{A'}$R$^{B'}$ such C$_1$-C$_6$ alkyl being optionally substituted by a group C$_1$-C$_3$ alkyl or halo.

In another embodiment R$^A$ and R$^B$ form together with the nitrogen atom to which they are attached a 4-11-membered saturated heterocyclic monocyclic ring system which is substituted by —(C$_1$-C$_5$ alkylene)-NR$^{A'}$R$^{B'}$, wherein R$^{A'}$ and R$^{B'}$ are independently —H or C$_1$-C$_6$ alkyl optionally substituted by a group C$_1$-C$_3$ alkyl.

In one embodiment R$^{17}$ is a group of general formula (IV)

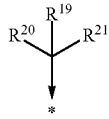

(IV)

wherein R$^{19}$ is selected in a group consisting of —H, —CH$_3$, —CN and OH; R$^{20}$ is selected in the group consisting of: —H, —F, —CH$_3$, —C$_2$H$_5$ and —CH$_2$OH; R$^{21}$ is —H, —CH$_3$ or —C$_2$H$_5$.

In one embodiment R$^{19}$ is —H, R$^{20}$ and R$^{21}$ are —CH$_3$.
In one embodiment R$^{19}$ and R$^{20}$ are H and R$^{21}$ is —CH$_3$.
In one embodiment R$^{19}$, R$^{20}$ and R$^{21}$ are —H.
In one embodiment R$^{19}$, R$^{20}$ and R$^{21}$ are —CH$_3$.

In one embodiment R$^{18}$ is absent or is selected in the group consisting of aryl, heteroaryl and —(C$_1$-C$_6$alkyl) wherein any of such aryl, heteroaryl and —(C$_1$-C$_6$alkyl) may be optionally substituted by one or more group(s) selected from —OH, —C$_1$-C$_6$alkyl, C$_3$-C$_6$cycloalkyl, —O—(C$_1$-C$_6$alkyl), —O—(C$_3$-C$_6$cycloalkyl), —NR$^H$R$^J$, —N(R$^L$)(C$_2$-C$_6$alkylene)-NR$^H$R$^J$, —N(R$^L$)(C$_3$-C$_7$cycloalkylene)-NR$^H$R$^J$, —(C$_1$-C$_6$alkylene)-NR$^H$R$^J$, —(C$_3$-C$_7$cycloalkylene)-NR$^H$R$^J$, —O—(C$_2$-C$_6$alkylene)-NR$^H$R$^J$, —O—(C$_3$-C$_7$cycloalkylene)-NR$^H$R$^J$, OR$^L$, wherein any of such C$_1$-C$_6$alkyl, C$_3$-C$_6$cycloalkyl, —(C$_1$-C$_6$alkylene)-, —(C$_2$-C$_6$alkylene)- and —(C$_3$-C$_7$cycloalkylene)-portion in the above listed groups may be optionally substituted by a group C$_1$-C$_6$ alkyl, C$_3$-C$_7$ cycloalkyl, —OR$^L$ or halo.

In one embodiment R$^{18}$ is aryl optionally substituted by one or more group(s) selected from —C$_1$-C$_6$alkyl, —(C$_1$-C$_6$alkylene)-NR$^H$R$^J$, —O—(C$_2$-C$_6$alkylene)-NR$^H$R$^J$ wherein any of such C$_1$-C$_6$alkyl, —(C$_1$-C$_6$alkylene)- and —(C$_2$-C$_6$alkylene)-portion in the above listed groups may be optionally substituted by a group C$_1$-C$_6$ alkyl, C$_3$-C$_7$ cycloalkyl, —OR$^L$ or halo.

In one embodiment R$^H$ and R$^J$ are at each occurrence independently C$_1$-C$_6$ alkyl or C$_3$-C$_6$ cycloalkyl, such C$_1$-C$_6$ alkyl or C$_3$-C$_6$ cycloalkyl being optionally substituted by a group C$_1$-C$_3$ alkyl, —OR$^M$, —CN or halo; alternatively, R$^H$ and R$^J$ may form together with the nitrogen atom to which they are attached an azetidine or a 4-11 membered saturated monocyclic or bicyclic heterocyclic ring system which is optionally substituted by one or more groups —OR$^M$, —CN, halo, NR$^O$R$^P$, C$_1$-C$_6$ alkyl or C$_3$-C$_7$ cycloalkyl, such C$_1$-C$_6$ alkyl and C$_3$-C$_7$ cycloalkyl being optionally substituted by a group C$_1$-C$_3$ alkyl, C$_3$-C$_7$cycloalkyl, —OR$^M$, —CN or halo; and which 6-11-membered saturated monocyclic or bicyclic heterocyclic ring optionally contains a further heteroatom which is oxygen or nitrogen, said nitrogen atom optionally substituted by C$_1$-C$_6$ alkyl or C$_3$-C$_6$ cycloalkyl, wherein any of such C$_1$-C$_6$ alkyl or C$_3$-C$_6$ cycloalkyl may be optionally substituted by a group C$_1$-C$_6$ alkyl, C$_3$-C$_7$ cycloalkyl, —OR$^M$, —CN, or halo.

In another embodiment R$^H$ and R$^J$ may form together with the nitrogen atom to which they are attached an azetidine or a 4-11 membered saturated monocyclic heterocyclic ring system which is optionally substituted by one or more groups —OR$^M$, NR$^O$R$^P$ or C$_1$-C$_6$ alkyl wherein such C$_1$-C$_6$ alkyl is optionally substituted by a group C$_1$-C$_3$ alkyl, —OR$^M$ or halo; and which 6-11-membered saturated monocyclic heterocyclic ring optionally contains a further heteroatom which is oxygen or nitrogen, said nitrogen atom optionally substituted by C$_1$-C$_6$ alkyl or C$_3$-C$_6$ cycloalkyl, wherein any of such C$_1$-C$_6$ alkyl or C$_3$-C$_6$ cycloalkyl may be optionally substituted by a group C$_1$-C$_6$ alkyl, C$_3$-C$_7$ cycloalkyl, —OR$^M$, —CN or halo.

In one embodiment R$^L$ is independently —H, C$_1$-C$_6$ alkyl or C$_3$-C$_6$ cycloalkyl, such C$_1$-C$_6$ alkyl or C$_3$-C$_6$ cycloalkyl being optionally substituted by a group C$_1$-C$_3$ alkyl, —OR$^M$, —CN or halo.

In one embodiment R$^M$ is independently —H, C$_1$-C$_6$ alkyl or C$_3$-C$_6$ cycloalkyl, such C$_1$-C$_6$ alkyl or C$_3$-C$_6$ cycloalkyl being optionally substituted by a group hydroxyl, —CN or halo.

In one embodiment R$^O$ and R$^P$ are each independently C$_1$-C$_6$ alkyl or C$_1$-C$_6$ cycloalkyl, optionally substituted by a group C$_1$-C$_3$ alkyl or —OR$^Q$; alternatively, R$^O$ and R$^P$ may form together with the nitrogen atom to which they are attached a 4-8-membered saturated monocyclic heterocyclic ring system which is optionally substituted by one or more groups —OR$^Q$, —CN, halo, C$_1$-C$_6$ alkyl or C$_3$-C$_7$ cycloalkyl, and which 6-8-membered saturated monocyclic heterocyclic ring optionally contains a further heteroatom which is oxygen or nitrogen, said nitrogen atom optionally substituted by C$_1$-C$_6$ alkyl or C$_3$-C$_6$ cycloalkyl.

In another embodiment R$^O$ and R$^P$ are each independently C$_1$-C$_6$ alkyl or C$_1$-C$_6$ cycloalkyl, optionally substituted by a group C$_1$-C$_3$ alkyl.

In one embodiment R$^Q$ is —H, —CH$_3$ or —C$_2$H$_5$.

In one embodiment z$^1$=—CH—, z$^2$=C, z$^3$ is O or N and z$^4$ is N.

In an additional embodiment $R^2$ is a radical of formula (IIIa)

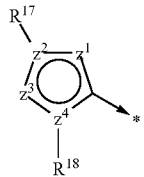
(IIIa)

wherein $z^1$=—CH—, $z^2$=C, $z^3$ is O, $z^4$ is N, $R^{18}$ is absent, and $R^{17}$ is a group of general formula (IV)

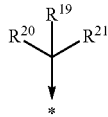
(IV)

wherein $R^{19}$, $R^{20}$ and $R^{21}$ are —CH$_3$.

In a further embodiment, $R^2$ is a radical of formula (IIIa)

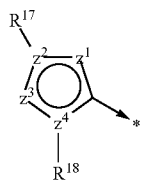
(IIIa)

wherein $z^1$=—CH—, $z^2$=C, $z^3$ and $z^4$ are N and $R^{17}$ is a group of general formula (IV)

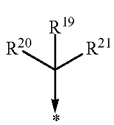
(IV)

wherein $R^{19}$ is —H, $R^{20}$ and $R^{21}$ are —CH$_3$.

In another embodiment, $R^2$ is a radical of formula (IIIa)

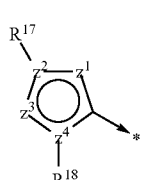
(IIIa)

wherein $z^1$=—CH—, $z^2$=C, $z^3$ and $z^4$ are N and $R^{17}$ is a group of general formula (IV)

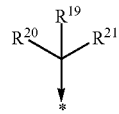
(IV)

$R^{19}$ and $R^{20}$ are H and $R^{21}$ is —CH$_3$.

In a further embodiment $R^2$ is a radical of formula (IIIa)

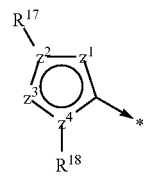
(IIIa)

wherein $z^1$=—CH—, $z^2$=C, $z^3$ and $z^4$ are N and $R^{17}$ is a group of general formula (IV)

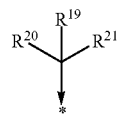
(IV)

wherein $R^{19}$, $R^{20}$ and $R^{21}$ are —H.

In an additional embodiment $R^2$ is a radical of formula (IIIa)

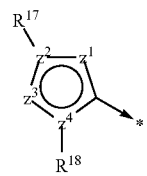
(IIIa)

wherein $z^1$=—CH—, $z^2$=C, $z^3$ and $z^4$ are N and $R^{17}$ is a group of general formula (IV)

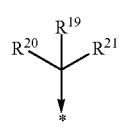
(IV)

wherein $R^{19}$, $R^{20}$ and $R^{21}$ are —CH$_3$ and $R^{18}$ is absent or is selected from —(C$_1$-C$_6$alkyl), —(C$_1$-C$_6$alkylene)-NR$^H$R$^J$, —O—(C$_2$-C$_6$alkylene)-NR$^H$R$^J$ or aryl, wherein any portion in the above listed groups may be optionally substituted by a group C$_1$-C$_6$ alkyl, C$_3$-C$_7$ cycloalkyl, —OR$^L$ or halo.

In another embodiment $R^2$ is a radical of formula (IIIa)

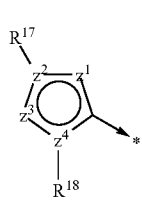

(IIIa)

wherein $z^1$=—CH—, $z^2$=C, $z^3$ and $z^4$ are N and $R^{17}$ is a group of general formula (IV)

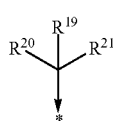

(IV)

wherein $R^{19}$ is —H, $R^{20}$ and $R^{21}$ are —CH$_3$ and $R^{18}$ is heteroaryl substituted by a —(C$_1$-C$_6$alkylene)-NR$^H$R$^J$, wherein $R^H$ and $R^J$ are independently C$_1$-C$_6$ alkyl optionally substituted by a group C$_1$-C$_3$ alkyl, —OR$^M$, —CN or halo; alternatively, $R^H$ and $R^J$ may form together with the nitrogen atom to which they are attached a 4-11 membered saturated monocyclic heterocyclic ring system which is optionally substituted by one or more groups —OR$^M$, halo, NR$^O$R$^P$, C$_1$-C$_6$ alkyl or C$_3$-C$_7$ cycloalkyl; and which 6-11-membered saturated monocyclic heterocyclic ring optionally contains a further heteroatom which is oxygen or nitrogen, said nitrogen atom optionally substituted by C$_1$-C$_6$ alkyl optionally substituted by a group C$_1$-C$_6$ alkyl, C$_3$-C$_7$ cycloalkyl, —CN, or halo.

In another embodiment $R^2$ is a radical of formula (IIIa)

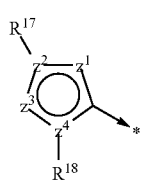

(IIIa)

wherein $z^1$=—CH—, $z^2$=C, $z^3$ and $z^4$ are N and $R^{17}$ is a group of general formula (IV)

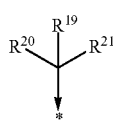

(IV)

wherein $R^{19}$ and $R^{20}$ are —H, and $R^{21}$ is —CH$_3$ and $R^{18}$ is heteroaryl substituted by a —(C$_1$-C$_6$alkylene)-NR$^H$R$^J$, wherein $R^H$ and $R^J$ are independently C$_1$-C$_6$ alkyl optionally substituted by a group C$_1$-C$_3$ alkyl, —CN or halo.

In another embodiment $R^2$ is a radical of formula (IIIa)

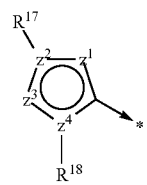

(IIIa)

wherein $z^1$=—CH—, $z^2$=C, $z^3$ and $z^4$ are N and $R^{17}$ is a group of general formula (IV)

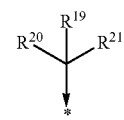

(IV)

wherein $R^{19}$, $R^{20}$ and $R^{21}$ are —CH$_3$ and $R^{18}$ is aryl or heteroaryl optionally substituted by a group selected from —(C$_1$-C$_6$alkyl), —O—(C$_1$-C$_6$alkylene)-NR$^H$R$^J$ or —(C$_1$-C$_6$alkylene)-NR$^H$R$^J$ and wherein A is a group

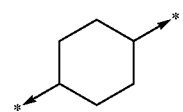

In another embodiment $R^2$ is a radical of formula (IIIa)

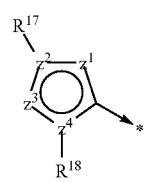

(IIIa)

wherein $z^1$=—CH—, $z^2$=C, $z^3$ and $z^4$ are N and $R^{17}$ is a group of general formula (IV)

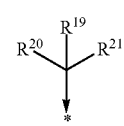

(IV)

wherein $R^{19}$, $R^{20}$ and $R^{21}$ are —CH$_3$ and $R^{18}$ is aryl optionally substituted by —(C$_1$-C$_6$alkyl), —(C$_2$-C$_6$alkylene)-NR$^H$R$^J$ or —O—(C$_2$-C$_6$alkylene)-NR$^H$R$^J$.

In another embodiment $R^2$ is a radical of formula (IIIa)

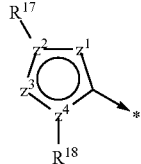
(IIIa)

wherein $z^1$=—CH—, $z^2$=C, $z^3$ and $z^4$ are N and $R^{17}$ is a group of general formula (IV)

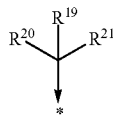
(IV)

wherein $R^{19}$, $R^{20}$ and $R^{21}$ are H and $R^{18}$ is phenyl optionally substituted by a —O—($C_2$-$C_6$alkylene)-$NR^HR^J$, wherein $R^H$ and $R^J$ are independently $C_1$-$C_6$ alkyl optionally substituted by a group $C_1$-$C_3$ alkyl, —CN or halo.

In another embodiment $R^2$ is a radical of formula (IIIa)

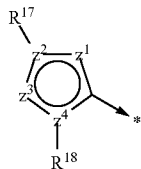
(IIIa)

wherein $z^1$=—CH—, $z^2$=C, $z^3$ and $z^4$ are N and $R^{17}$ is a group of general formula (IV)

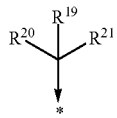
(IV)

wherein $R^{19}$, $R^{20}$ and $R^{21}$ are H and $R^{18}$ is phenyl optionally substituted by —O—($C_2$-$C_6$alkylene)-$NR^HR^J$, wherein $R^H$ and $R^J$ are independently $C_1$-$C_6$ alkyl.

In one embodiment, compounds of formula (IA) are provided wherein W is NH, Y is a group —O($CR^3R^4$)$_n$— and n is 0, A is group

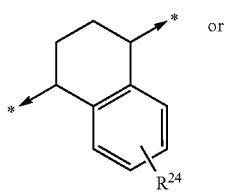

wherein $R^1$ is a group of formula (IIaa) as above defined which is connected to the group Y through the carbon adjacent to $X^2$

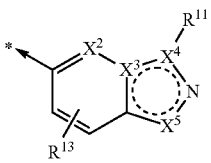
(IIaa)

and wherein $X^4$ is a carbon atom, $X^5$ is a nitrogen atom, $X^3$ is a nitrogen atom and $X^2$ is a group —CH—, and $R^{13}$ is —H; wherein $R^{11}$ is a group:

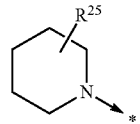

wherein $R^{25}$ represents one, two or three substituents independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$;

wherein $R^2$ is a radical of formula (IIIa)

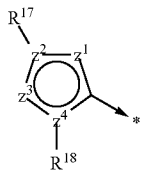
(IIIa)

wherein $z^1$=—CH—, $z^2$=C, $z^3$ and $z^4$ are N and $R^{17}$ is a group of general formula (IV)

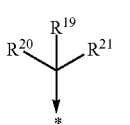
(IV)

wherein $R^{19}$, $R^{20}$ and $R^{21}$ are —$CH_3$ and wherein $R^{18}$ is phenyl optionally substituted by a group selected from $C_1$-$C_6$ alkyl, —($C_2$-$C_6$alkylene)-$NR^HR^J$ and —O—($C_2$-$C_6$alkylene)-$NR^HR^J$, wherein $R^H$ and $R^J$ are independently $C_1$-$C_6$ alkyl optionally substituted by a group $C_1$-$C_3$ alkyl, —CN or halo.

In one embodiment, compounds of formula (IB) are provided wherein W is NH, Y is a group —O($CR^3R^4$)$_n$— and n is 0, A is group

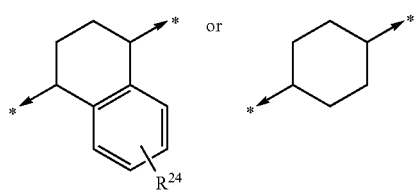

wherein $R^1$ is a group of formula (IIaa) as above defined which is connected to the group Y through the carbon adjacent to $X^2$

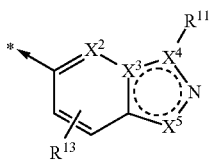

(IIaa)

wherein $X^4$ is a carbon atom, $X^5$ is a nitrogen atom, $X^3$ is a nitrogen atom and $X^2$ is a group —CH—, and $R^{13}$ is —H; wherein $R^{11}$ is a group —$NR^A R^B$, wherein $R^A$ and $R^B$ form together with the nitrogen atom to which they are attached a 4-11-membered saturated heterocyclic monocyclic ring system which is substituted by —($C_1$-$C_5$ alkylene)-$NR^{A'}R^{B'}$, wherein $R^{A'}$ and $R^{B'}$ are independently —H or $C_1$-$C_6$ alkyl optionally substituted by a group $C_1$-$C_3$ alkyl, $C_3$-$C_7$cycloalkyl, —$OR^{D'}$, —CN or halo; or $R^{11}$ is a group

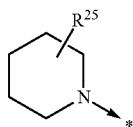

wherein $R^{25}$ represents one or two substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; wherein $R^2$ is a radical of formula (Ma)

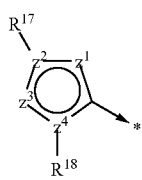

(IIIa)

wherein $z^1$=—CH—, $z^2$=C, $z^3$ and $z^4$ are N and $R^{17}$ is a group of general formula (IV)

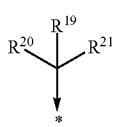

(IV)

wherein $R^{19}$, $R^{20}$ and 21 are —$CH_3$ and wherein $R^{18}$ is heteroaryl optionally substituted by a group selected from $C_1$-$C_6$ alkyl, —($C_2$-$C_6$alkylene)-$NR^H R^J$ and —O—($C_2$-$C_6$alkylene)-$NR^H R^J$, wherein $R^H$ and $R^J$ form together with the nitrogen atom to which they are attached an azetidine or a 4-11 membered saturated monocyclic heterocyclic ring system which is optionally substituted by one or more groups —$OR^M$, —CN, halo, $NR^O R^P$, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, wherein $R^O$ and $R^P$ are each independently $C_1$-$C_6$ alkyl.

In one embodiment, compounds of formula (IC) are provided wherein W is NH, Y is a group —$O(CR^3R^4)_n$— and n is 0, A is group:

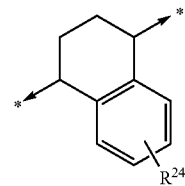

$R^{11}$ is a group:

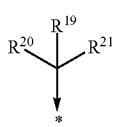

wherein $R^{25}$ is optionally present and represents one or two substituents independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; $R^2$ is a radical of formula (Ma)

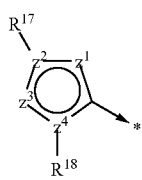

(IIIa)

wherein $z^1$=—CH—, $z^2$=C, $z^3$ and $z^4$ are N and $R^{17}$ is a group of general formula (IV)

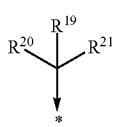

(IV)

wherein $R^{19}$, $R^{20}$ and $R^{21}$ are H and $R^{18}$ is phenyl optionally substituted by —O—($C_1$-$C_6$alkylene)-$NR^H R^J$, wherein $R^H$ and $R^J$ are $C_1$-$C_6$ alkyl.

In one embodiment, compounds of formula (ID) are provided wherein W is NH, Y is a group —$O(CR^3R^4)_n$— and n is 0, A is group

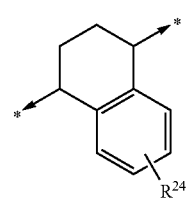

$R^1$ is a group of formula (IIaa) as above defined which is connected to the group Y through the carbon adjacent to $X_2$

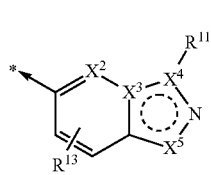

(IIaa)

wherein $X^4$ is a carbon atom, $X^5$ is a nitrogen atom, $X^3$ is a nitrogen atom and $X^2$ is a group —CH—, and $R^{13}$ is —H; wherein $R^{11}$ is a group:

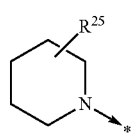

wherein $R^{25}$ is optionally present and represents one two or three substituents independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; wherein $R^2$ is a radical of formula (IIIa):

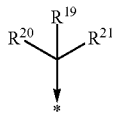

(IIIa)

wherein $z^1$=—CH—, $z^2$=C, $z^3$ and $z^4$ are N and $R^{17}$ is a group of general formula (IV)

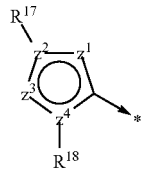

(IV)

wherein $R^{19}$ is —H, $R^{20}$ and $R^{21}$ are —CH$_3$ and $R^{18}$ is heteroaryl substituted by a —(C$_1$-C$_6$alkylene)-NR$^H$R$^J$, wherein R$^H$ and R$^J$ are independently C$_1$-C$_6$ alkyl optionally substituted by a group C$_1$-C$_3$ alkyl, —OR$^M$, —CN or halo; alternatively, R$^H$ and R$^J$ may form together with the nitrogen atom to which they are attached a 4-11 membered saturated monocyclic heterocyclic ring system which is optionally substituted by one or more groups —OR$^M$, halo, NR$^O$R$^P$, C$_1$-C$_6$ alkyl or C$_3$-C$_7$ cycloalkyl; and which 6-11-membered saturated monocyclic heterocyclic ring optionally contains a further heteroatom which is oxygen or nitrogen, said nitrogen atom optionally substituted by C$_1$-C$_6$ alkyl optionally substituted by a group C$_1$-C$_6$ alkyl, C$_3$-C$_7$ cycloalkyl, —CN or halo.

In one embodiment, compounds of formula (IE) are provided wherein W is NH, Y is a group —O(CR$^3$R$^4$)$_n$— and n is 0, A is group

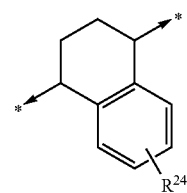

$R^1$ is a group of formula (IIaa) as above defined which is connected to the group Y through the carbon adjacent to $X_2$

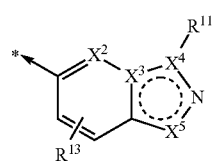

(IIaa)

wherein $X^4$ is a carbon atom, $X^5$ is a nitrogen atom, $X^3$ is a nitrogen atom and $X^2$ is a group —CH—, and $R^{13}$ is —H; wherein $R^{11}$ is a group:

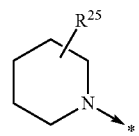

wherein $R^{25}$ is optionally present and represents one two or three substituents independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; wherein $R^2$ is a radical of formula (IIIa)

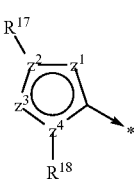

(IIIa)

wherein $z^1$=—CH—, $z^2$=C, $z^3$ and $z^4$ are N and $R^{17}$ is a group of general formula (IV)

(IV)

wherein $R^{19}$ and $R^{20}$ are H and $R^{21}$ is —CH$_3$ and $R^{18}$ is heteroaryl substituted by a —(C$_1$-C$_6$alkylene)-NR$^H$R$^J$, wherein R$^H$ and R$^J$ are independently C$_1$-C$_6$ alkyl optionally substituted by a group C$_1$-C$_3$ alkyl, —CN or halo.

In one embodiment, compounds of formula (IF) are provided wherein W is NH, Y is a group —O(CR$^3$R$^4$)$_n$— and n is 0, A is group

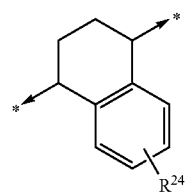

wherein $R^1$ is a group of formula (IIaa) as above defined which is connected to the group Y through the carbon adjacent to $X^2$

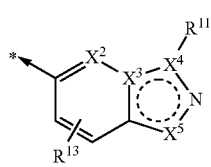

(IIaa)

wherein $X^4$ is a carbon atom, $X^5$ is a nitrogen atom, $X^3$ is a nitrogen atom and $X^2$ is a group —CH—, and $R^{13}$ is —H; wherein $R^{11}$ is a group —$NR^AR^B$, wherein $R^A$ and $R^B$ form together with the nitrogen atom to which they are attached a 4-11-membered saturated heterocyclic monocyclic ring system which is substituted by —$(C_1$-$C_5$alkylene)-$NR^{A'}R^{B'}$, wherein $R^{A'}$ and $R^{B'}$ are independently —H or $C_1$-$C_6$ alkyl optionally substituted by a group $C_1$-$C_3$ alkyl, $C_3$-$C_7$cycloalkyl, —$OR^{D'}$, —CN or halo; wherein $R^2$ is a radical of formula (IIIa)

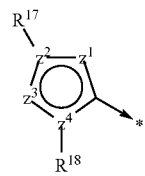

(IIIa)

wherein $z^1$=—CH—, $z^2$=C, $z^3$ and $z^4$ are N and $R^{17}$ is a group of general formula (IV)

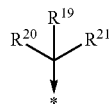

(IV)

wherein $R^{19}$, $R^{20}$ and $R^{21}$ are —$CH_3$ and wherein $R^{18}$ is —$C_1$-$C_6$alkyl, optionally substituted by $C_1$-$C_6$ alkyl, $C_3$-$C_7$ cycloalkyl, —$OR^L$ or halo.

In one embodiment, compounds of formula (IG) are provided wherein W is NH, Y is a group —$O(CR^3R^4)_n$— and n is 0, A is group

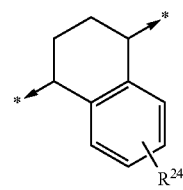

wherein $R^1$ is a group of formula (IIaa) as above defined which is connected to the group Y through the carbon adjacent to $X^2$

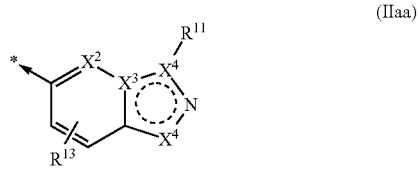

(IIaa)

wherein $X^4$ is a carbon atom, $X^5$ is a nitrogen atom, $X^3$ is a nitrogen atom and $X^2$ is a group —CH—, and $R^{13}$ is —H; wherein $R^{11}$ is phenyl which is optionally substituted by one or more group(s) selected from halo, $C_1$-$C_6$ alkyl, wherein such $C_1$-$C_6$ alkyl is optionally substituted by —$(C_1$-$C_6$alkylene)-$NR^AR^B$, wherein $R^A$ and $R^B$ may form together with the nitrogen atom to which they are attached a 4-11-membered saturated heterocyclic monocyclic ring system which is optionally substituted by one or more groups selected from —$OR^D$, —CN, —$NR^CR^D$, halo, $C_1$-$C_6$ alkyl or $C_3$-$C_7$ cycloalkyl; and which 6-11-membered saturated heterocyclic monocyclic ring optionally contains a further heteroatom which is oxygen or nitrogen, said nitrogen atom optionally substituted by $C_1$-$C_6$ alkyl or $C_3$-$C_6$ cycloalkyl; wherein $R^2$ is a radical of formula (IIIa)

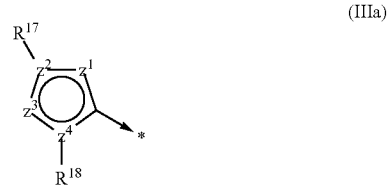

(IIIa)

wherein $z^1$=—CH—, $z^2$=C, $z^3$ is O, $z^4$ is N, $R^{18}$ is absent, and $R^{17}$ is a group of general formula (IV)

(IV)

wherein $R^{19}$, $R^{20}$ and $R^{21}$ are —$CH_3$ and $R^{18}$ is —($C_1$-$C_6$alkyl).

In one embodiment, compounds of formula (IH) are provided wherein W is NH, Y is a group —$O(CR^3R^4)_n$— and n is 0, A is group:

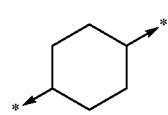

wherein $R^1$ is a group of formula (IIaa) as above defined which is connected to the group Y through the carbon adjacent to $X^2$ (IIaa)

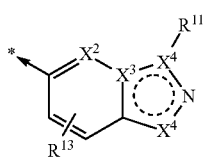

wherein $X^4$ is a carbon atom, $X^5$ is a nitrogen atom, $X^3$ is a nitrogen atom and $X^2$ is a group —CH—, and $R^{13}$ is —H; wherein $R^{11}$ is a group

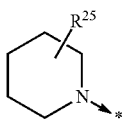

wherein $R^{25}$ represents one or two substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; wherein $R^2$ is a radical of formula (IIIa)

(IIIa)

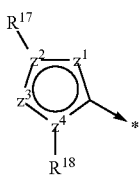

wherein $z^1$=—CH—, $z^2$=C, $z^3$ and $z^4$ are N and $R^{17}$ is a group of general formula (IV)

(IV)

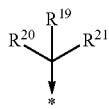

wherein $R^{19}$, $R^{20}$ and $R^{21}$ are —$CH_3$ and wherein $R^{18}$ is aryl or heteroaryl optionally substituted by a group selected from $C_1$-$C_6$ alkyl, —($C_2$-$C_6$alkylene)-$NR^HR^J$ and —O—($C_2$-$C_6$alkylene)-$NR^HR^J$, wherein $R^H$ and $R^J$ are independently $C_1$-$C_6$ alkyl or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN or halo.

In one embodiment, compounds of formula (IL) are provided wherein W is NH, Y is a group —O($CR^3R^4$)$_n$— and n is 0, A is group

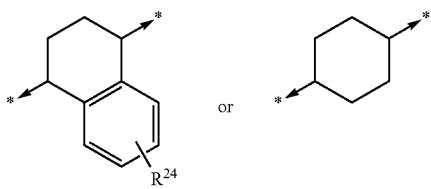

$R^{11}$ is a group:

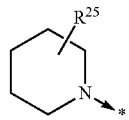

wherein $R^{25}$ is optionally present and represents one or two substituents independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; $R^2$ is a radical of formula (IIIa)

(IIIa)

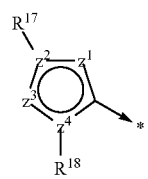

wherein $z^1$=—CH—, $z^2$=C, $z^3$ and $z^4$ are N and $R^{17}$ is a group of general formula (IV)

(IV)

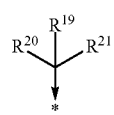

wherein $R^{19}$, $R^{20}$ and $R^{21}$ are $CH_3$ and $R^{18}$ is phenyl optionally substituted by a group selected from $C_1$-$C_6$ alkyl, —($C_2$-$C_6$alkylene)-$NR^HR^J$ and —O—($C_2$-$C_6$alkylene)-$NR^HR^J$, wherein $R^H$ and $R^J$ are $C_1$-$C_6$ alkyl or $R^H$ and $R^J$ form together with the nitrogen atom to which they are attached an azetidine or a 4-11 membered saturated monocyclic heterocyclic ring system which is optionally substituted by one or more groups halo or $NR^OR^P$, wherein $R^O$ and $R^P$ are each independently $C_1$-$C_6$ alkyl.

In one embodiment, a compound of formula (I) is selected from the group consisting of:

1-[1'-(2-Dimethylamino-ethyl)-3-isopropyl-1'H-[1,4']bipyrazolyl-5-yl]-3-{(1S,4R)-4-[3-((2S,6R)-2,6-dimethyl-piperidin-1-yl)-[1,2,4]triazolo[4,3a]pyridin-6-yloxy]-1,2,3,4-tetrahydro-naphthalen-1-yl}-urea formate salt;

1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-{3-isopropyl-1'-[2-(4-methyl-piperazin-1-yl)-ethyl]-1'H-[1,4']bipyrazolyl-5-yl}-urea formate salt;

1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-[3-isopropyl-1'-(2-pyrrolidin-1-yl-ethyl)-1'H-[1,4']bipyrazolyl-5-yl]-urea formate salt;

1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-[3-isopropyl-1'-(2-[1,4]oxazepan-4-yl-ethyl)-1'H-[1,4']bipyrazolyl-5-yl]-urea formate salt;

1-[1'-(2-Dimethylamino-ethyl)-3-isopropyl-1'H-[1,3']bipyrazolyl-5-yl]-3-{(1S,4R)-4-[3-((2S,6R)-2,6-dimethylpiperidin-1-yl)-[1,2,4]triazolo[4,3a]pyridin-6-yloxy]-1,2, 3,4-tetrahydro-naphthalen-1-yl}-urea formate salt;

1-[1'-(2-Dimethylamino-ethyl)-3-isopropyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[1'-(2-Dimethylamino-ethyl)-3-ethyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[1'-(2-Dimethylamino-ethyl)-3-ethyl-1'H-[1,4']bipyrazolyl-5-yl]-3-{(1S,4R)-4-[3-((2S,6R)-2,6-dimethyl-piperidin-1-yl)-[1,2,4]triazolo[4,3a]pyridin-6-yloxy]-1,2,3, 4-tetrahydro-naphthalen-1-yl}-urea formate salt;

1-{2-[3-(2-Dimethylamino-ethoxy)-phenyl]-5-methyl-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[1'-(2-Azetidin-1-yl-ethyl)-3-tert-butyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(3-dimethylamino-azetidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[3-(3-dimethylamino-azetidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-(5-tert-Butyl-2-methyl-2H-pyrazol-3-yl)-3-((1S,4R)-4-{3-[2,6-dichloro-4-(4-methyl-piperazin-1-ylmethyl)-phenyl]-[1,2,4]triazolo[4,3-a]pyridin-6-yloxy}-1,2,3,4-tetrahydro-naphthalen-1-yl)-urea formate salt;

1-(5-tert-Butyl-2-methyl-2H-pyrazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt;

1-(5-tert-Butyl-isoxazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea;

1-(3-tert-Butyl-1'-methyl-1'H-[1,4']bipyrazolyl-5-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3-{4-[3-((2S,6R)-2,6-dimethyl-piperidin-1-yl)-[1,2,4]triazolo[4,3-a]pyridin-6-yloxy]-cyclohexyl}-urea;

1-(5-tert-Butyl)-2-p-tolyl-2H-pyrazol-3-yl)-3-{4-[3-((S)-2-methyl-piperidin-1-yl)-[1,2,4]triazolo[4,3-a]pyridin-6-yloxy]-cyclohexyl}-urea;

1-{5-tert-Butyl-2-[3-(2-dimethylamino-ethoxy)-phenyl]-2H-pyrazol-3-yl}-3-{4-[3-((S)-2-methyl-piperidin-1-yl)-[1,2,4]triazolo[4,3-a]pyridin-6-yloxy]-cyclohexyl}-urea;

1-{5-(Cyano-dimethyl-methyl)-2-[3-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl}-urea;

1-{5-(Cyano-dimethyl-methyl)-2-[3-(2-dimethylamino-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-methyl-2H-pyrazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-[5-tert-Butyl-2-(2-hydroxy-ethyl)-2H-pyrazol-3-yl]-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-(3-tert-Butyl-1'-methyl-1'H-[1,4']bipyrazolyl-5-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-(5-tert-Butyl-isoxazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-(5-tert-Butyl-2-propyl-2H-pyrazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-[5-tert-Butyl-2-(2-methoxy-ethyl)-2H-pyrazol-3-yl]-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-(5-tert-Butyl-2-methyl-2H-pyrazol-3-yl)-3-{(1S,4R)-4-[3-((S)-3-{[(2-hydroxy-ethyl)-methyl-amino]-methy}-piperidin-1-yl)-[1,2,4]triazolo[4,3-a]pyridin-6-yloxy]-1,2, 3,4-tetrahydro-naphthalen-1-yl}-urea hydrogen chloride salt;

1-(5-tert-Butyl-2-methyl-2H-pyrazol-3-yl)-3-{(1S,4R)-4-[3-((S)-3-dimethylaminomethyl-piperidin-1-yl)-[1,2,4]triazolo[4,3-a]pyridin-6-yloxy]-1,2,3,4-tetrahydro-naphthalen-1-yl}-urea hydrogen chloride salt;

1-(5-tert-Butyl-2-methyl-2H-pyrazol-3-yl)-3-{(1S,4R)-4-[3-(4-{[(2-methoxy-ethyl)-methyl-amino]-methyl}-piperidin-1-yl)-[1,2,4]triazolo[4,3-a]pyridin-6-yloxy]-1,2,3, 4-tetrahydro-naphthalen-1-yl}-urea;

1-(5-tert-Butyl-2-methyl-2H-pyrazol-3-yl)-3-{(1S,4R)-4-[3-(4-{[(2-hydroxy-ethyl)-methyl-amino]-methyl}-piperidin-1-yl)-[1,2,4]triazolo[4,3-a]pyridin-6-yloxy]-1,2,3, 4-tetrahydro-naphthalen-1-yl}-urea hydrogen chloride salt;

1-(5-tert-Butyl-2-methyl-2H-pyrazol-3-yl)-3-{(1S,4R)-4-[3-(4-[1,4]oxazepan-4-ylmethyl-piperidin-1-yl)-[1,2,4]triazolo[4,3-a]pyridin-6-yloxy]-1,2,3,4-tetrahydro-naphthalen-1-yl}-urea hydrogen chloride salt;

1-(5-tert-Butyl-2-methyl-2H-pyrazol-3-yl)-3-{(1S,4R)-4-{3-[4-(4-methyl-piperazin-1-ylmethyl)-piperidin-1-yl]-[1,2,4]triazolo[4,3-a]pyridin-6-yloxy}-1,2,3,4-tetrahydro-naphthalen-1-yl}-urea hydrogen chloride salt;

1-(5-tert-Butyl-2-methyl-2H-pyrazol-3-yl)-3-{(1S,4R)-4-[3-((R)-3-{[(2-hydroxy-ethyl)-methyl-amino]-methyl}-piperidin-1-yl)-[1,2,4]triazolo[4,3-a]pyridin-6-yloxy]-1, 2,3,4-tetrahydro-naphthalen-1-yl}-urea hydrogen chloride salt;

1-[5-tert-Butyl-2-(2-methoxy-ethyl)-2H-pyrazol-3-yl]-3-{(1S,4R)-4-[3-(4-dimethylaminomethyl-piperidin-1-yl)-[1,2,4]triazolo[4,3-a]pyridin-6-yloxy]-1,2,3,4-tetrahydronaphthalen-1-yl}-urea;

1-(5-tert-Butyl-2-ethyl-2H-pyrazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt;

N-[5-tert-Butyl-3-(3-{(1S,4R)-4-[3-(4-dimethylaminom-ethyl-piperidin-1-yl)-[1,2,4]triazolo[4,3-a]pyridin-6-yloxy]-1,2,3,4-tetrahydro-naphthalen-1-yl}-ureido)-2-methoxyphenyl]methanesulfonamide hydrogen chloride salt;

1-(5-tert-Butyl-2-methyl-2H-pyrazol-3-yl)-3-{(1S,4R)-4-[3-((2S,4S)-4-dimethylamino-1-methyl-pyrrolidin-2-yl)-[1,2,4]triazolo[4,3-a]pyridin-6-yloxy]-1,2,3,4-tetrahydro-naphthalen-1-yl}-urea hydrochloride salt;

1-(5-tert-Butyl-2-methyl-2H-pyrazol-3-yl)-3-{(1S,4R)-4-[3-(1,4-dimethyl-1,4,9-triaza-spiro[5.5]undec-9-yl)-[1,2,4]triazolo[4,3-a]pyridin-6-yloxy]-1,2,3,4-tetrahydro-naphthalen-1-yl}-urea hydrochloride salt and pharmaceutically acceptable salts thereof.

Utility.

As mentioned above the compounds of the invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

The present invention provides the use of the compounds of the invention for the prevention and/or treatment of any disease or condition which benefit from inhibition of the p38 enzyme.

In a further aspect the present invention provides the use of compounds of the invention for the preparation of a medicament for the prevention and/or treatment of any disease or condition which benefit from inhibition of the p38 enzyme.

Moreover the present invention provides a method for prevention and/or treatment of any disease which benefit from inhibition of the p38 enzyme, said method comprises administering to a patient in need of such treatment a therapeutically effective amount of a compound of the invention.

Compositions

As mentioned above, the compounds with which the invention is concerned are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases. For the purpose of the invention, inhaled administration is preferred.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or coloring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, a preservative and a buffering agent can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler), for metered aerosols, in particular in the case of powder inhalers, a number of technical solutions are available (e.g. Diskhaler®, Rotadisk®, Turbohaler® or the inhalers for example as described EP-A-0505321, which is incorporated herein by reference in its entirety). Additionally, compounds of the invention may be delivered in multi-chamber devices thus allowing for delivery of combination agents.

Combinations.

Other compounds may be combined with compounds with which the invention is concerned for the prevention and treatment of inflammatory diseases, in particular respiratory diseases. Thus, the present invention is also concerned with pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199, vilanterol, olodaterol and abediterol; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, formoterol/beclometasone dipropionate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028, EP-101; (5) dual pharmacology M3-anticholinergic/β2-adrenoreceptor agonists such as GSK961081, AZD2115 and LAS190792; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723, or selective histamine-4 (H4) receptor antagonists, such as ZPL3893787; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonoclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO2005/026124, WO2003/053930 and WO06/082412, which are incorporated herein by reference in their entireties; (20) A2b antagonists such as those described in WO2002/42298; (21) modulators of chemokine receptor function, for example antagonists of CCR3 and CCR8; (22) compounds which modulate the action of other prostanoid receptors, for example a thromboxane A2 antagonist; DP1 antagonists such as MK-0524, CRTH2 antagonists such as ODC9101 and OC000459 and AZD1981 and mixed DP1/CRTH2 antagonists such as AMG 009 and AMG853; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176; (26) CXCR2 or IL-8 antagonists such as SCH 527123 or GSK 656933; (27) IL-R signalling modulators such as kineret and ACZ 885; (28) MCP-1 antagonists such as ABN-912.

The invention is also directed to a kit comprising the pharmaceutical compositions of compounds of the invention alone or in combination with or in admixture with one or more pharmaceutically acceptable carriers and/or excipients and a device which may be a single- or multi-dose dry powder inhaler, a metered dose inhaler or a nebulizer.

Methods of Synthesis.

In one aspect of the present invention, a process for the preparation of compounds of the invention is provided, according to general synthetic routes described in this section. In the following reaction schemes, unless otherwise indicated, the groups mentioned assume the same meaning as those reported for compounds of formula (I).

The skilled person may introduce, where appropriate, suitable variations to the conditions specifically described in the experimentals in order to adapt the synthetic routes to the provision of further compounds of the invention. Such variations may include, but are not limited to, use of appropriate starting materials to generate different compounds, changes in the solvent and temperature of reactions, replacements of reactives with analogous chemical role, introduction or removal of protection/deprotection stages of functional groups sensitive to reaction conditions and reagents, as well as introduction or removal of specific synthetic steps oriented to further functionalisation of the chemical scaffold.

Processes which can be used and are described and reported in Examples and Schemes, should not be viewed as limiting the scope of the synthetic methods available for the preparation of the compounds of the invention.

The process described is particularly advantageous as it is susceptible of being properly modulated, through any proper variant known to the skilled person, so as to obtained any of the desired compounds of the invention. Such variants are comprised within the scope of the present invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art [see, for a general reference, T. W. Green; Protective Groups in Organic Synthesis (Wiley, N.Y. 1981), which is incorporated herein by reference in its entirety].

Likewise, selective protection and deprotection of any of the said groups, for instance including carbonyl, hydroxyl or amino groups, may be accomplished according to very well known methods commonly employed in organic synthetic chemistry.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

For example compounds of the invention of formula (I) may be prepared according to the route illustrated in Scheme 1.

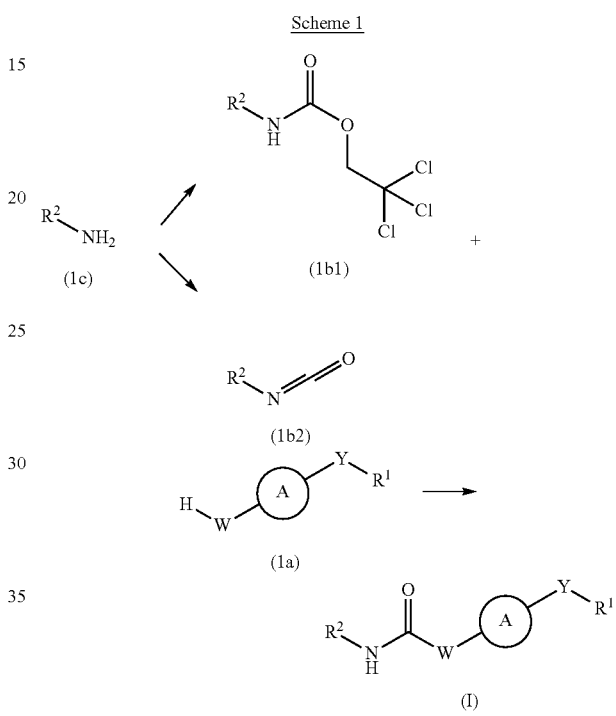

Compounds of general formula (I) may be prepared from compounds of general formula (1a) by reaction with a compound of general formula (1b1) or (1b2) wherein $R^2$ is as defined in general formula (I), in a suitable solvent such as dimethyl sulfoxide, 1,4-dioxane, N,N-dimethylformamide or acetonitrile, in the presence of a base such as diisopropylethylamine at a range of temperatures, preferably between room temperature and 100° C.

Compounds of general formula (1b1) and (1b2) are either known in the literature or may be prepared from amines of general formula (1c) according to known literature procedures (e.g. see for reference WO2006009741, EP1609789, which are incorporated herein by reference in their entireties).

Compounds of general formula (1c) are either known in the literature or may be synthesised by one skilled in the art by adapting appropriate literature methods (e.g. WO2010077836, WO2006009741, WO2008125014, J. Med Chem., 2007, 50, 4016, Bulletin des Societes Chimiques Belges, 1987, 96, 675-709, Organic & Biomolecular Chemistry, 2006, 4, 4158-4164, which are incorporated herein by reference in their entireties).

Compounds of general formula (1ca), i.e. compounds of formula (1c) wherein $R^2$ is a group of formula (Mb) and $R^{17}$, $R^{18}$, $z^1$, $z^2$, $z^3$ and $z^4$ are as defined above can be prepared from compounds of formula (1e),

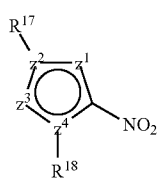

(1e)

using a suitable reducing agent such as tin (II) chloride, iron, or hydrogen gas with a suitable catalyst such as palladium on carbon, in a suitable solvent such as methanol, ethanol or acetic acid, at a range of temperatures, preferably between room temperature and 100° C.

Compounds of general formula (1e) are known in the literature or may be prepared by those skilled in the art using literature methods (e.g. WO2008034008, WO20110189167, WO2010068258, which are incorporated herein by reference in their entireties).

Alternatively, compounds of general formula (1 ca) as above defined can be prepared from compounds of formula (1f), wherein $R^{17}$, $R^{18}$ $z^1$, $z^2$, $z^3$ and $z^4$ are as defined above and wherein PG is a suitable compatible protecting group known to those skilled in the art, such as benzyl, benzyl carbamate or tert-butyl carbamate,

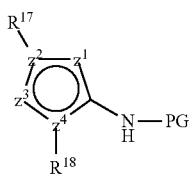

(1f)

using suitable deprotection conditions such as hydrochloric acid, trifluoroacetic acid, or hydrogen catalysed by for example palladium on carbon, in a suitable solvent such as dichloromethane, methanol, ethanol or acetic acid, at a range of temperatures, preferably between 0° C. and 100° C.

Compounds of general formula (1f) can be prepared by reaction of compounds of formula (1g), wherein $R^{17}$, $R^{18}$, $z^1$, $z^2$, $z^3$ and $z^4$ are as defined above

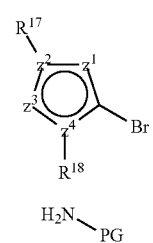

(1g)

(1h)

with compounds of formula (1h) as above reported wherein PG is a suitable protecting group known to those skilled in the art, such as benzyl, benzyl carbamate or tert-butyl carbamate, using suitable conditions such as in the presence of a base such as potassium carbonate or diisopropylethyl amine or under Buchwald conditions (with a catalyst such as Pd (OAc)$_2$, a ligand such as 2,2'-bis(diphenylphosphino)-1,1'-binaphthyl and base such as sodium tert-butoxide), in a suitable solvent such as toluene or tetrahydrofuran, at a range of temperatures, preferably between room temperature and 150° C.

Compounds of general formula (1g) and (1h) are known in the literature or may be prepared by those skilled in the art by adapting appropriate literature methods (e.g. WO2011042389, Chemistry-A European Journal, 2011, 17, 6606-6609, S6606/1-S6606/38, which are incorporated herein by reference in their entireties).

Compounds of general formula (1a) may be prepared according to the route illustrated in Scheme 2.

Scheme 2

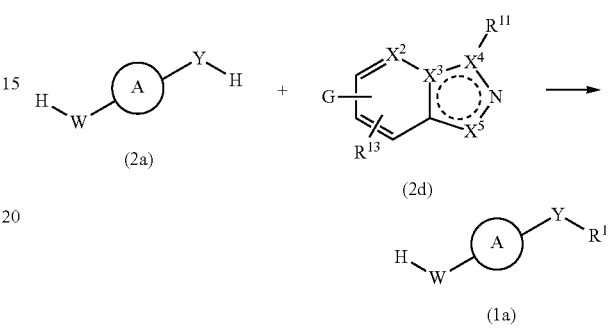

Compounds of general formula (1a) may be prepared from compounds of general formula (2a) by reaction with a compound of general formula (2d). Wherein G is a suitable chemical group known to those skilled in the art selected such that it can facilitate a suitable coupling reaction such as nucleophilic displacement or metal catalysed cross coupling. For example in cases such that when Y is —O—, —S— or —NR$^7$—, examples of G may include halogen or a suitable leaving group such as mesylate or triflate either directly linked or attached via a group —(CR$^3$R$^4$)—, Examples of the coupling conditions used may include using a base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between room temperature and 150° C. For example in cases such that when Y is —O— and G is —OH or —SH a method to perform this coupling may involve Mitsunobu conditions (diethylazodicarboxylate/triphenylphosphine) in a suitable solvent such as tetrahydrofuran or 1,4-dioxane at a range of temperatures preferably between −10° C. and 100° C. For example in cases such as when Y is —O—, —S— or —NR$^7$— and G is a group such as halogen, triflate or boronic acid/ester a method to perform this coupling may be under metal (for example palladium or copper) catalysed coupling conditions in the presence of a suitable ligand such as Xantphos or 1,10-phenanthroline in the presence of a base such as caesium carbonate in a suitable solvent such as tetrahydrofuran, 1,4-dioxane or N,N-dimethylformamide at a range of temperatures preferably between −10° C. and 150° C. For example in cases such as when Y is —O— and G is a group such as —COOMe, —COOH, isocyanate, —OCOCl or —NHCOOCH$_2$CCl$_3$ examples of conditions to perform this coupling may involve the use of a base such as sodium hydride or triethylamine or a coupling reagent such as HATU in a suitable solvent such as dichloromethane, tetrahydrofuran, 1,4-dioxane or N,N-dimethylformamide at a range of temperatures preferably between −10° C. and 150° C.

Compounds of formula (2da), i.e. compounds of formula (2a) wherein X$^4$═C may be prepared according to the routes described in Scheme 3 herebelow:

Scheme 3

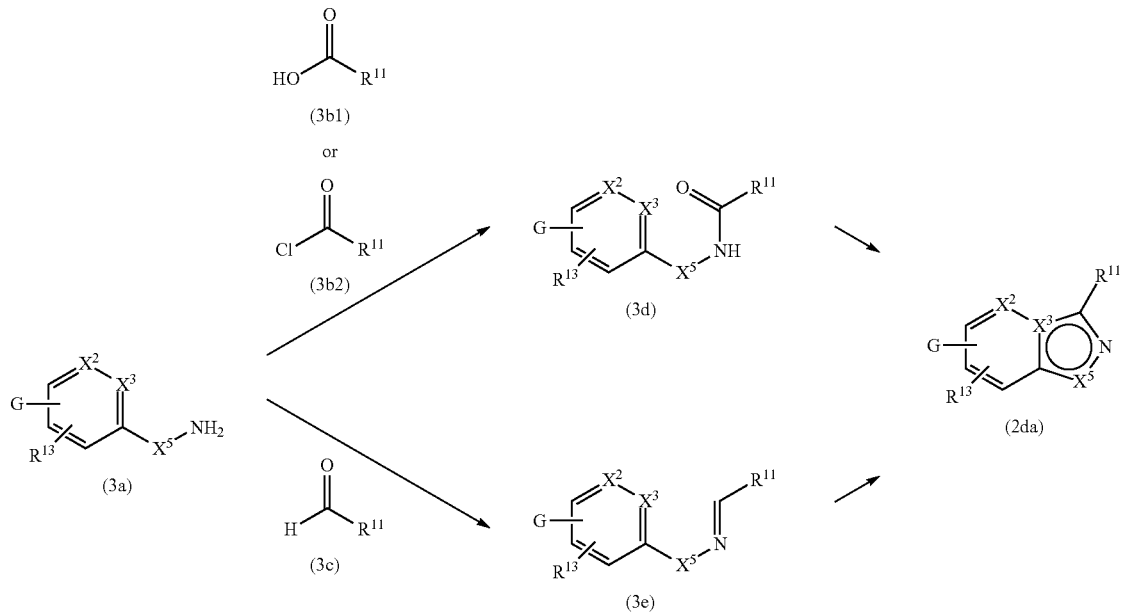

Compounds of general formula (2da) as above defined may be prepared from compounds of general formula (3e) using a suitable oxidant such as chloramine T, lead tetracetate or phenyl iodine(III) diacetate, in a suitable solvent such as dichloromethane or ethanol at a range of temperatures, preferably between room temperature and 100° C.

Compounds of general formula (3e) may be prepared from compounds of general formula (3a) by reaction with an aldehyde of general formula (3c) above reported, in a suitable solvent such as ethanol or tetrahydrofuran at a range of temperatures, preferably between room temperature and 80° C.

Compounds of formula (3c) are commercially available, known in the literature or may be prepared using literature methods by those skilled in the art.

Alternatively, compounds of formula (2da) may be prepared from compounds of formula (3d) using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene or NMP, at a range of temperatures, preferably between room temperature and 150° C.

Compounds of formula (3d) may be prepared from compounds of formula (3a) by reaction with a compound of general formula (3b1) using a suitable acylating/dehydrating agent such as triphenylphosphine/trichloroacetonitrile in the presence of a base such as diisopropylethylamine, in a suitable solvent such as dichloromethane or acetonitrile, at a range of temperatures, preferably between room temperature and 150° C.

Or by reaction with a compound of general formula (3b2) in the presence of a base such as diisopropylethylamine, in a suitable solvent such as dichloromethane or THF at a range of temperatures preferably between −10° C. and the boiling point of the solvent.

Compounds of formulae (3b1) and (3b2) are commercially available, known in the literature or may be prepared by literature methods by those skilled in the art. Alternatively, compounds of formula (2da) as above defined may be prepared according to the route in Scheme 4:

Scheme 4

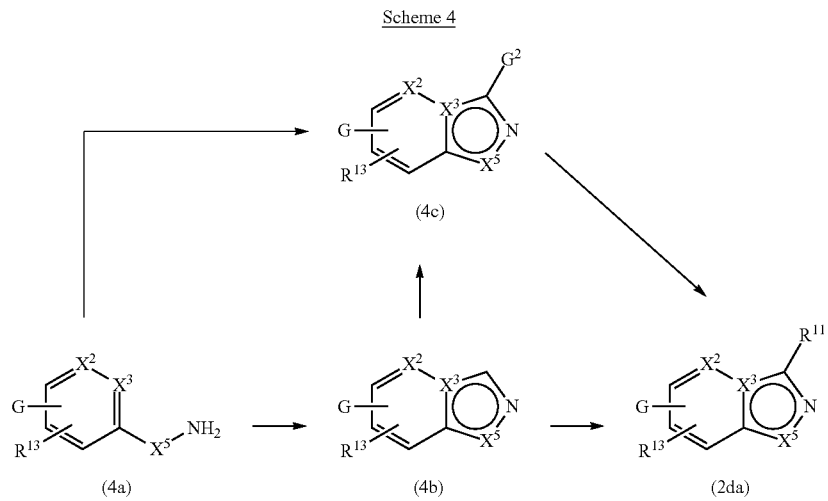

Compounds of general formula (2da) may be prepared from compounds of general formula (4c) wherein $G^2$ may represent groups such as halogen, —CHO, —COOH, —COOEt and $SO_2Cl$.

For example, compounds of general formula (2da) may be prepared from compounds of general formula (4c), wherein $G^2$ represents halogen, using methods such as a metal (for example palladium) catalysed coupling with a suitable $R^{11}G^5$ derivative wherein $G^5$ is a group such as boronate acid/ester or stannane in a suitable solvent such as tetrahydrofuran or 1,4-dioxane at a range of temperatures preferably between ambient temperature and 150° C. An alternative method may involve displacement of said halogen with a suitable group $R^{11}H$ (such as that containing an —NH, —OH or —SH group) in the presence of a base such as sodium hydride, potassium tert-butoxide or N,N-diethylisopropylamine in a suitable solvent such as N,N-Dimethylformamide, toluene, 1,4-dioxane or acetonitrile at a range of temperatures, preferably between room temperature and 150° C.

The group $G^2$ may be also transformed from groups such as halogen to groups such as —CHO, —COOH, —COOEt and $SO_2Cl$ by means of metal insertion methods known to those skilled in the art such as palladium catalysis, Grignard formation or lithium halogen exchange.

Compounds of general formula (4c) wherein $G^2$ is a group such as —COOEt, may be synthesised from compounds of general formula (4a) by reaction with a compound such as diethyloxalate in the presence of an acid such as acetic acid at a range of temperatures, preferably between room temperature and 120° C.

Compounds of general formula (4c) wherein $G^2$ is a group such as bromine or chlorine, may be synthesised from compounds of general formula (4b) by reaction with a compound such as N-chlorosuccinimide or N-bromosuccinimide in a solvent such as chloroform at a range of temperatures, preferably between −10° C. and room temperature.

Compounds of general formula (4b) may be synthesised from compounds of general formula (4a) by reaction with a compound such as diethoxymethylacetate at a range of temperatures, preferably between room temperature and 100° C.

Compounds of general formula (2db), i.e. compounds of formula (2d) wherein $X_4$ is nitrogen, may be prepared from compounds of general formula (4b) wherein $X^4$=NH, by reaction with a suitable alkylating agent $R^{11}$ in the presence of a base such as caesium carbonate in a suitable solvent such as N,N-dimethylformamide at a range of temperatures, preferably between room temperature and 150° C.

Alternatively, compounds of general formula (1aa), i.e. compounds of formula (1a) wherein $X^4$ is CH may be prepared according to the route illustrated in Scheme 5.

Scheme 5

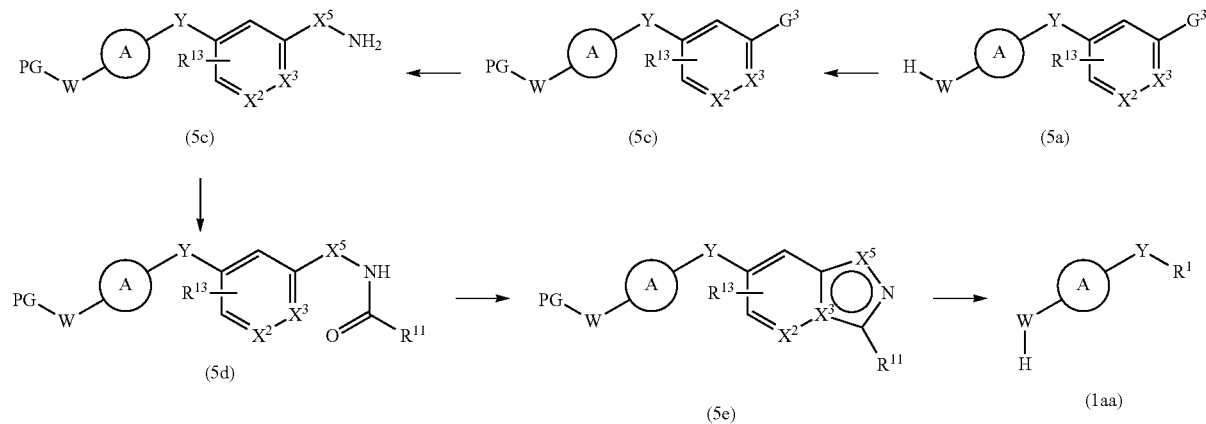

Compounds of general formula (2da) wherein $R^{11}$ is a group such as —$CH_2$—$NR^AR^B$, —C(O)N($R^C$)—($C_2$-$C_6$alkylene)-$NR^AR^B$, —C(O)N($R^C$)—($C_3$-$C_7$cycloalkylene)-$NR^AR^B$, —C(O)N($R^C$)—($C_2$-$C_6$alkylene)-$OR^D$, —C(O)N($R^C$)—($C_3$-$C_7$cycloalkylene)-$OR^D$, —C(O)N($R^A$)S(O)$_2$N($R^C$)—($C_2$-$C_6$alkylene)-$NR^AR^B$, —S(O)$_2$N($R^C$)—($C_3$-$C_7$cycloalkylene)-$NR^AR^B$, —S(O)$_2$N($R^C$)—($C_2$-$C_6$alkylene)-$OR^D$ or —S(O)$_2$N($R^C$)—($C_3$-$C_7$cycloalkylene)-$OR^D$ may be prepared from compounds of general formula (4c), wherein $G^2$ represents —CHO, —COOH, —COOEt and —$SO_2Cl$, by reaction with a suitable amine such as $HNR^AR^B$ etc using methods such as reductive amination (using a reagent such as sodium triacetoxyborohydride) or amide/sulphonamide formation in the presence of suitable reagents such as HATU with a base such as N,N-diethylisopropylamine or trimethylaluminium in a suitable solvent such as dichloromethane, N,N-dimethylformamide, toluene, 1,4-dioxane or acetonitrile at a range of temperatures, preferably between room temperature and 150° C.

Compounds of general formula (1aa) may be prepared from compounds of general formula (5e) wherein PG is a suitable protecting group known in the art such as Boc by using the appropriate deprotection conditions such as trifluoroacetic acid in a solvent such as dichloromethane at a range of temperatures, preferably between −10° C. and room temperature.

Compounds of general formula (5e) may be prepared from compounds of general formula (5d) using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene or NMP, at a range of temperatures, preferably between room temperature and 120° C.

Compounds of general formula (5d) may be prepared from compounds of general formula (5c) by reaction with a compound of general formula (3b1) as above defined using a suitable acylating/dehydrating agent such as triphenylphosphine/trichloroacetonitrile in the presence of a base such as diisopropylethylamine, in a suitable solvent such as dichloromethane or acetonitrile, at a range of temperatures, preferably between room temperature and 150° C., or by reaction with a compound of general formula (3b2) as above defined in the presence of a base such as diisopropylethylamine, in a suitable solvent such as dichloromethane or THF at a range of temperatures preferably between −10° C. and the boiling point of the solvent.

Compounds of general formula (5c) may be prepared from compounds of general formula (5b) wherein $G^3$ is a suitable leaving group such as halogen, by reaction with a reagent such as hydrazine monohydrate in a suitable solvent such as ethanol at a range of temperatures preferably between room temperature and 100° C.

Compounds of general formula (5b) may be prepared from compounds of general formula (5a) by reaction with a suitable protecting group reagent known in the art such as Boc anhydride in the presence of a base such as triethylamine in a suitable solvent such as dichloromethane or tetrahydrofuran at a range of temperatures preferably between room temperature and 100° C.

Compounds of general formula (5a) can be synthesised by the methods described above for the synthesis of (1a).

Compounds of general formula (2aa), i.e. compounds of formula (2a) wherein Y=O, W=NH and PG is a suitable protective group such as trifluoroacetate may be prepared according to the route illustrated in scheme 6:

or RuCl[S,S-Tsdpen(p-cymene)]. Compound (2a) is drawn with no defined stereocentres but any combination can be obtained as illustrated in Scheme 2.

Compounds of formula (6a) can be prepared from compounds of formula (6d)

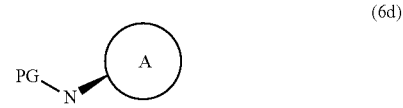

(6d)

using a suitable oxidant such as potassium permanganate and magnesium sulfate in a suitable solvent methanol/water at a range of temperatures preferably between room temperature and the boiling point of the solvent. It will be recognised that compounds of formula (6d) may be homochiral as illustrated or be the opposite enantiomer or racemic.

Compounds of formula (6d) can be prepared from compounds of formula (6e) where PG is a suitable protecting group such as trifluoroacetate or tert-butyl carbonate:

(6e)

Scheme 6

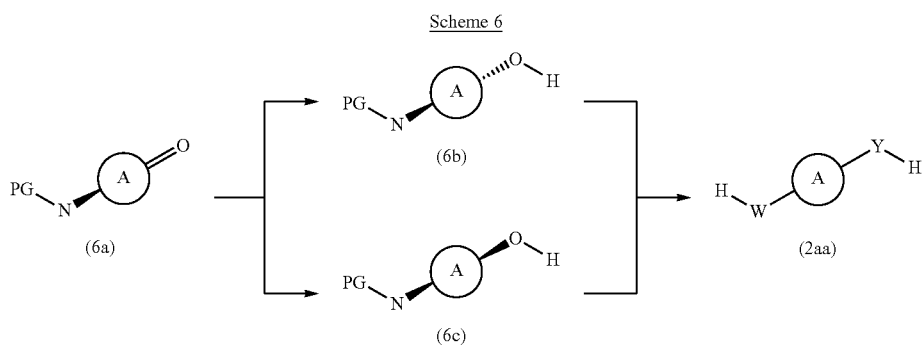

Compounds of general formula (2aa) may be prepared from compounds of general formula (6b) and (6c) by removal of the protecting group PG using methods known in the art such as aqueous sodium hydroxide in a solvent such as methanol at a range of temperatures preferably between room temperature and 100° C.

Compounds of general formula (6b), wherein PG is a protecting group, preferably trifluoroacetamide, and the group —OH is placed on the cycloalkylene portion of ring A may be prepared from compounds of general formula (6a) by using a chiral reductive method such as using formic acid and RuCl [S,S-Tsdpen(p-cymene)] in the presence of a base such as triethylamine in a solvent such as N,N-dimethylformamide at a range of temperatures preferably between room temperature and 150° C. It will be recognised that compounds of formula (6a) may be homochiral as illustrated or be the opposite enantiomer or racemic.

It will be realized by those skilled in the art that any combination of stereocenters in (2aa) can be prepared using both enantiomers of (6a) and using RuCl[R,R-Tsdpen(p-cymene)]

using ethyl trifluoroacetate or di-tert-butyl dicarbonate in the presence of base such as triethylamine or diisopropylethylamine in a solvent such as methanol or dichloromethane at a range of temperatures preferably between 0° C. and the boiling point of the solvent. It will be recognised that compounds of formula (6e) may be homochiral as illustrated or be the opposite enantiomer or racemic.

Compounds of formula (6e) are known in the literature and may be prepared by those skilled in the art by adapting literature methods (e.g. for S-(+)-1-amino-1,2,3,4-tetrahydronaphthalene, see Journal of the Chemical Society, Perkin Transactions 1: 1985, 2039-44; for (S)-(+)-8-amino-5,6,7,8-tetrahydroquinoline, see Journal of Organic Chemistry, 2007, 72, 669-671; and for 1-aminoindan see Tetrahedron Letters, 2011, 52, 1310-1312, all of which are incorporated herein by reference in their entireties).

Compounds of general formula (2ab), i.e. compounds of formula (2a) wherein Y=$NR^7$ and W=NH, may be prepared according to the route illustrated in scheme 7:

Scheme 7

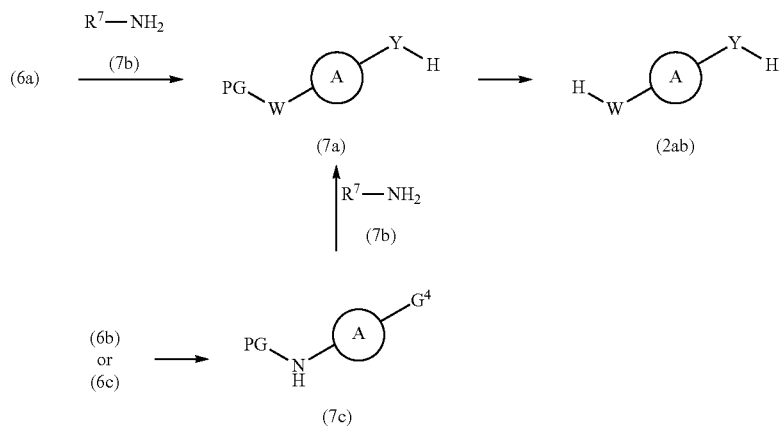

Compounds of general formula (2ab) may be prepared from compounds of general formula (7a) by removal of the protecting group PG using methods known in the art such as aqueous sodium hydroxide in a solvent such as methanol or trifluoroacetic acid in dichloromethane at a range of temperatures preferably between room temperature and 100° C.

Compounds of formula (7a) may be prepared from compounds of general formula (6a) and amines (7b) by reaction under reductive amination conditions, using a reducing agent such as sodium triacetoxyborohydride and a solvent such as 1,2-dichloroethane at a range of temperatures preferably between room temperature and 100° C.

Compounds for formula (7b) are known in the literature and may be prepared by those skilled in the art using literature procedures. Compounds of formula (6a) can be prepared as described above.

Alternatively, compounds of formula (7a) may be prepared from compounds of general formula (7c) wherein $G^4$ is a suitable chemical group known to those skilled in the art selected such that it can facilitate a reaction such as a nucleophilic substitution. For example G is a suitable leaving group such as halogen or mesylate which can react with a suitable amine (7b) in the presence of a suitable base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between room temperature and 150° C.

Compounds of formula (7c) can be prepared from compounds of formulae (6b) or (6c) using halogenating conditions such as carbon tetrabromide and triphenylphosphine in dichloromethane or activation conditions such as methane sulfonyl chloride in dichloromethane in the presence of base such as diisopropylamine.

Alternatively, compounds of general formula (Id), i.e. compounds of formula (I) wherein Y=S and W=NH may be prepared according to the route illustrated in scheme 8:

Scheme 8

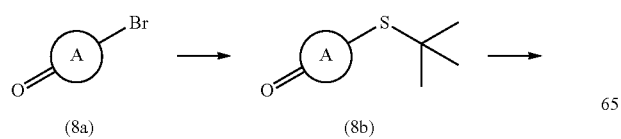

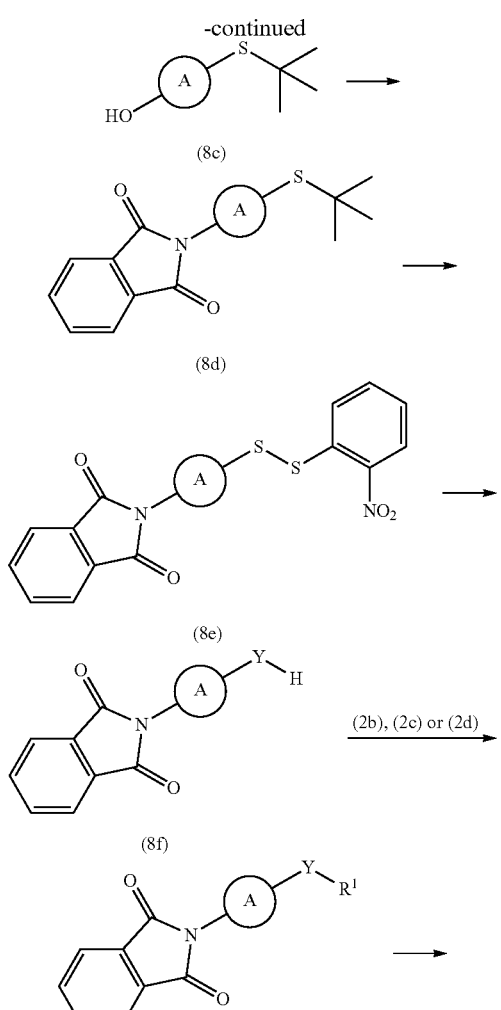

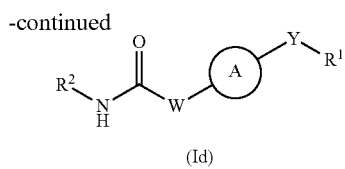

(Id)

Compounds of general formula (Id) may be prepared from compounds of general formula (1ab), i.e. compounds of formula (1a) wherein Y=S and W=NH: using compounds of formula (1b1) or (1b2) in a suitable solvent such as dimethyl sulfoxide, 1,4-dioxane, N,N-dimethylformamide or acetonitrile, in the presence of a base such as diisopropylethylamine at a range of temperatures, preferably between room temperature and 100° C.

Compounds of formula (1 ab) as above defined may be prepared from compounds of formula (8g) using deprotection conditions such as hydrazine in methanol at a range of temperatures preferably between room temperature and the boiling point of the solvent.

Compounds of formula (8g) wherein Y=S, can be prepared from compounds of formula (8f) by reaction with compounds of formulae (2b), (2c) or (2d). Examples of the coupling conditions used may include using a base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between room temperature and 150° C. Alternative methods to perform this coupling may involve Mitsunobu conditions (diethylazodicarboxylate/triphenylphosphine) or metal (for example palladium) catalysed coupling conditions in a suitable solvent such as tetrahydrofuran or 1,4-dioxane at a range of temperatures preferably between −10° C. and 150° C. and starting from the appropriate derivative of formula (2b), (2c), or (2d).

Compounds of formula (8f) can be prepared from compounds of formula (8e) using dithiothreitol, monopotassium phosphate, potassium carbonate in a solvent such as methanol in the presence of acetic acid at a range of temperatures preferably between room temperature and the boiling point of the solvent.

Compounds of formula (8e) can be prepared from compounds of formula (8d) using 2-nitrobenzenesulfenyl chloride in acetic acid at a range of temperatures preferably between room temperature and 100° C.

Compounds of formula (8d) can be prepared from compounds of formula (8c) using phthalimide, triphenylphosphine and diisopropyl azodicarboxylate in a solvent such as tetrahydrofuran at a range of temperature preferably between 0° C. and the boiling point of the solvent.

Compounds of formula (8c) can be prepared from compounds of formula (8b) using a reducing agent such as sodium borohydride in a solvent such as methanol at a range of temperatures preferably between 0° C. and the boiling point of the solvent.

Compounds of formula (8b) can be prepared from compounds of formula (8a) using tert-butanethiol in the presence of a base such as diisopropylethylamine in a solvent such as tetrahydrofuran at a range of temperatures preferably between 0° C. and the boiling point of the solvent.

Compounds of formula (8a) are known in the literature and can be prepared by those skilled in the art using literature methods (e.g. 3-bromo-indan-1-one see WO 2010108058).

Alternatively, compounds of general formula (1ab), i.e. compounds of formula (1a) wherein Y=CH$_2$, W=NH and PG is a suitable protective group such as trifluoroacetate may be prepared according to the route illustrated in scheme 9:

Scheme 9

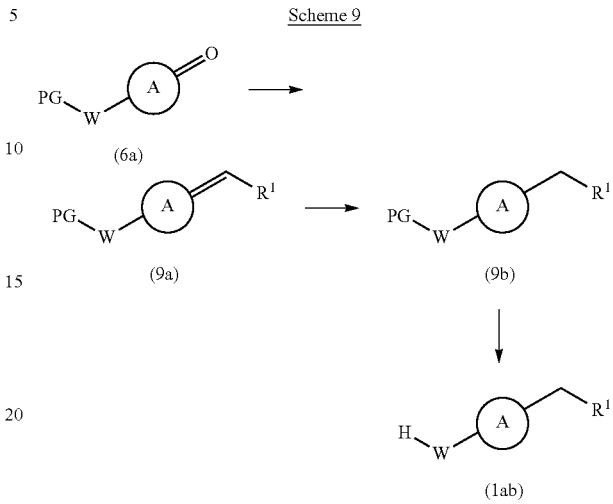

Compounds of general formula (1ab) may be prepared from compounds of general formula (9b) by removal of the protecting group PG using methods known in the art such as aqueous sodium hydroxide in a solvent such as methanol at a range of temperatures preferably between room temperature and 100° C.

Compounds of formula (9b) may be prepared from compounds of general formula (9a) by reaction with a suitable reduction agent for example hydrogen gas in the presence of a suitable catalyst such as palladium on activated charcoal in a suitable solvent such as ethanol at a range of temperatures between room temperature and 70° C. and pressures between atmospheric and 4 Barr.

Compounds of formula (9a) may be prepared from compounds of general formula (6a) by means of a reaction such as a Wittig (or one of the closely related variants such as the Horner-Wadsworth-Emmons) with a suitable substrate such as R$^1$—CH$_2$—P(O)(OMe)$_2$ in the presence of a suitable base such as sodium hydride in a suitable solvent such as tetrahydrofuran at a range of temperatures preferably between −10° C. and 100° C.

Compounds such as R$^1$—CH$_2$—P(O)(OMe)$_2$ may be synthesised from compounds of the general formula R$^1$—CH$_2$—Hal wherein Hal represents a halogen such as —Br or —Cl by reaction with a compound such as trimethylphosphite at a range of temperatures preferably between 0° C. and 100° C.

Compounds such as R$^1$—CH$_2$—Hal may be synthesised from compounds of formula R$^1$—CH$_3$ by means of a reaction such as a radial halogenation using a reagent such as N-bromosuccinimide in the presence of a catalyst such as AIBN in a suitable solvent such as carbon tetrachloride at a range of temperatures preferably between 0° C. and 80° C. Compounds such as R$^1$—CH$_2$—Hal may also be synthesised from compounds formula R$^1$—CH$_2$—OH by means of using halogenating conditions such as carbon tetrabromide and triphenylphosphine in dichloromethane or activation conditions such as methane sulfonyl chloride in dichloromethane in the presence of base such as diisopropylamine.

Compounds such as R$^1$—CH$_3$ and R$^1$—CH$_2$—OH may be prepared by methods outlined above for compounds (2b), (2c) and (2d).

Compounds of the invention of formula (1ac), i.e. compounds of formula (1a) where Y=(CR$^5$R$^6$)$_n$ and W=NH, may be prepared according to the route illustrated in Scheme 10.

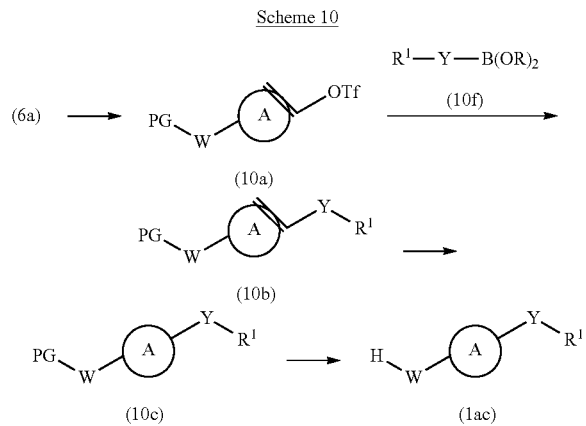

Scheme 10

Compounds of formula (1ac) may be prepared from compounds of formula (10c) wherein PG is a suitable protecting group known to those skilled in the art, such as trifluoroacetamide, tert-butyl carbamate and benzyl carbamate by using suitable deprotection conditions such as, sodium hydroxide in methanol, trifluoroacetic acid in dichloromethane or hydrogen gas catalysed by for example palladium on carbon in ethanol, at a range of temperatures, preferably between 0° C. and 100° C.

Compounds of formula (10c) may be prepared from compounds of formula (10b) wherein PG is a suitable protecting group known to those skilled in the art, such as trifluoroacetamide, tert-butyl carbamate and benzyl carbamate by using hydrogen gas in the presence of a catalyst such as palladium on carbon, in a suitable solvent such as methanol or ethanol, in the presence or absence of an acid such as HCl, at a range of temperatures, preferably between 0° C. and 100° C.

Compounds of formula (10b) may be prepared from compounds of formula (10a) and (10f) by a reaction such as a cross-coupling using a suitable catalyst such as tetrakis(triphenylphosphine)palladium (0) or palladium acetate, and a base such as diisopropylethylamine, sodium tert-butoxide or caesium carbonate in a suitable solvent such as NMP, toluene or DMF, at a range of temperatures, preferably between 0° C. and 100° C. Alternatively (10b) may be prepared by adapting literature procedures (e.g. those reported in WO2009022633, which is incorporated herein by reference in its entirety).

Compounds of formula (10f) are known in the literature or may be prepared by those skilled in the art by adapting literature procedures (e.g. WO2008063287, which is incorporated herein by reference in its entirety).

Compounds of formula (10a) may be prepared from compounds of formula (6a) using a triflating agent such as triflic anhydride, in the presence of a suitable base such as pyridine or 2,6-bis(tert-butyl)-4-methylpyridine, in a solvent such as dichloromethane or chloroform at a range of temperatures, preferably between 0° C. and boiling point of the solvent. Alternatively (10a) may be prepared by adapting literature procedures (e.g those described in WO2009022633, which is incorporated herein by reference in its entirety).

Other features of the invention will become apparent in the course of the following descriptions of exemplary embodiments which are given for illustration of the invention and are not intended to be limiting thereof.

EXAMPLES

Abbreviations used in the experimental section:
AcOH=acetic acid;
aq.=aqueous;
DCM=dichloromethane;
DIAD=Diisopropyl azodicarboxylate;
DIPEA=diisopropylethylamine;
DMAP=N,N-dimethylaminopyridine;
DMF=N,N-dimethylformamide;
DMSO=dimethyl sulfoxide;
EDC=1-ethyl-3-(3'-dimethylaminopropyl)carbodiimide Hydrochloride;
EtOAc=ethyl acetate;
EtOH=ethanol;
Et$_2$O=diethyl ether;
Et$_3$N=triethylamine;
EtNiPr$_2$=diisopropylethylamine;
FCC=flash column chromatography;
h=hour;
HATU=2-(7-aza-1H-benzotriazole-1-yl)-1,1,3,3-tetramethyluronium hexafluorophosphate;
HOBt=1-hydroxy-benzotriazole;
HPLC=high performance liquid chromatography;
IMS=Industrial Methylated Spirits;
LCMS=liquid chromatography mass spectrometry;
NaOH=sodium hydroxide;
MeCN=acetonitrile;
MeOH=Methanol;
min=minutes;
NH$_3$=ammonia;
NMR=nuclear magnetic resonance;
RT=room temperature;
Rt=retention time;
at.=saturated;
SCX-2=strong cation exchange chromatography;
TFA=trifluoroacetic acid;
THF=Tetrahydrofuran;
H$_2$O=water;
Xantphos=4,5-Bis(diphenylphosphino)-9,9-dimethylxanthene;
X-Select=Waters X-select HPLC column;
IPA=propan-2-ol;
LDA=lithium diisopropylamide;
MDAP=mass-directed auto-purification;
Ph$_3$P=triphenylphosphine;
TBAF=tetrabutylammonium fluoride.

In the procedures that follow, after each starting material, reference to an Intermediate/Example number is usually provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The nomenclature of structures was assigned using Autonom 2000 Name software from MDL Inc. When the nomenclature of structures could not be assigned using Autonom, ACD/Name software utility part of the ACD/Labs Release 12.00 Product Version 12.5 (Build 45133, 16 Dec. 2010) was used. Stereochemical assignments of compounds are based on comparisons with data reported in WO2008/043019, which is incorporated herein by reference in its entirety, for key intermediates. All reactions were carried out under anhydrous conditions and an atmosphere of nitrogen or argon unless specified otherwise. Unless otherwise stated all transformations were carried at ambient temperature (room temperature).

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane ($\delta$=0 ppm). J values are given in Hz through-out. NMR spectra were assigned using DataChord Spectrum Analyst Version 4.0.b21 or SpinWorks version 3.

Where products were purified by flash column chromatography (FCC), 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP 1 purification system. All solvents and commercial reagents were used as received.

Compounds purified by preparative HPLC were purified using a C18-reverse-phase column (100×22.5 mm i.d Genesis column with 7 µm particle size), or a Phenyl-Hexyl column (250×21.2 mm i.d. Gemini column with 5 µm particle size), UV detection between 220-254 nm, flow 5-20 mL/min), eluting with gradients from 100-0 to 0-100% water/acetonitrile (containing 0.1% TFA or 0.1% formic acid) or water/MeOH (containing 0.1% TFA or 0.1% formic acid), or a C18-reverse-phase column (19×250 mm, XBridge OBD, with 5 µm particle size), eluting with gradients from 100-0 to 0-100% water/acetonitrile (containing 0.1% $NH_4OH$); or a ChiralPak IC column (10×250 mm i.d., with 5 µm particle size), unless otherwise indicated. Fractions containing the required product (identified by LCMS analysis) were pooled, the organic solvent removed by evaporation, and the remaining aqueous residue lyophilised, to give the final product. Products purified by preparative HPLC were isolated as free base, formate or TFA salts, unless otherwise stated.

The Liquid Chromatography Mass Spectroscopy (LCMS) and HPLC systems used are:

Method 1.

Waters Platform LC Quadrupole mass spectrometer with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µl, split to MS with in-line HP1100 DAD detector). MS ionization method—Electrospray (positive and negative ion).

Method 2.

Waters ZMD quadrupole mass spectrometer with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µL split to MS with in-line Waters 996 DAD detector). MS ionization method—Electrospray (positive and negative ion).

Method 3.

Waters ZMD quadrupole mass spectrometer with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µL split to MS with in-line HP1100 DAD detector). MS ionization method—Electrospray (positive and negative ion).

Method 4.

VG Platform II quadrupole spectrometer with a C18-reverse-phase column (30×4.6 mm Phenomenex Luna 3 µm particle size, elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 µl/min split to the ESI source with inline HP1050 DAD detector). MS ionization method—Electrospray (positive and negative ion).

Method 5.

Waters micromass ZQ2000 quadrupole mass spectrometer with an Acquity BEH C18 1.7 um 100×2.1 mm, Acquity BEH Shield RP18 1.7 um 100×2.1 mm or Acquity HSST3 1.8 um 100×2.1 mm, maintained at 40° C. Elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 6.

Phenomenex Gemini C18-reverse-phase column (250×21.20 mm 5 μm particle size), elution with A: water+0.1% formic acid; B: CH$_3$CN+0.1% formic acid. Gradient—90% A/10% B to 2% A/98% B over 20 min—flow rate 18 mL/min. Detection—In-line UV detector set at 254 nM wavelength.

Method 7.

Agilent 1260 infinity purification system. Column: XSELECT CSH Prep C18 OBD, particle size 5 μm, 30×150 mm, RT. Elution with A: water+0.1% formic acid; B: CH$_3$CN+0.1% formic acid. Gradient—90% A/10% B to 2% A/95% B over 22 min—flow rate 60 mL/mina Detection—In-line Agilent 6100 series single Quadrupole LC/MS.

Method 8.

Agilent 1260 infinity purification system. Column: XBridge Prep C18 OBD, particle size 5 μm, 30×150 mm, RT. Elution with A: water+0.1% ammonia; B: CH$_3$CN+0.1% ammonia. Gradient—90% A/10% B to 2% A/95% B over 22 min—flow rate 60 mL/min. Detection—In-line Agilent 6100 series single Quadrupole LC/MS.

Intermediate 1.
(1R,4S)-4-Amino-1,2,3,4-tetrahydro-naphthalen-1-ol

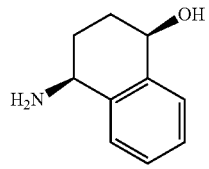

a. 2,2,2-Trifluoro-N—(S)-1,2,3,4-tetrahydro-naphthalen-1-yl-acetamide (Intermediate 1a)

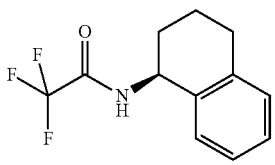 [SMILES: O=C(N[C@H]1CCCc2ccccc21)C(F)(F)F]

To a mechanically stirred solution of (S)-(+)-(1,2,3,4-tetrahydro-naphthalen-1-yl)amine (CAS: 23357-52-0, 175 g, 1.19 mol) and triethylamine (250 mL, 1.79 mol) in MeOH (1.75 L), ethyl trifluoroacetate (170 mL, 1.43 mol) was added dropwise at a rate to maintain the internal temperature below 30° C. (ca. over 20 min). The resulting solution was stirred at RT overnight. The mixture was concentrated in vacuo to give a solid. This was partitioned between DCM (1 L) and water (1 L). The layers were separated and the aqueous layer was extracted with DCM (2×600 mL). The combined organic layers were washed with brine, dried (Na$_2$SO$_4$), filtered and concentrated in vacuo to yield Intermediate 1a (289.4 g, 100%). $^1$H NMR (400 MHz, CDCl$_3$): 1.80-1.95 (3H, m), 2.05-2.15 (1H, m), 2.75-2.90 (2H, m), 5.18-5.25 (1H, q, J=5.0 Hz), 6.38-6.48 (1H, br s), 7.12-7.16 (1H, m), 7.20-7.26 (3H, m).

b. 2,2,2-Trifluoro-N-((S)-4-oxo-1,2,3,4-tetrahydro-naphthalen-1-yl)-acetamide (Intermediate 1b)

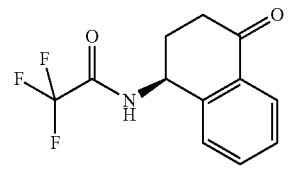 [SMILES: O=C1CC[C@H](NC(=O)C(F)(F)F)c2ccccc21]

A 20 L flask was charged with Intermediate 1a (288 g, 1.19 mol) and acetone (7 L). Magnesium sulfate monohydrate (328 g, 2.37 mol) in water (3 L) was added and the mixture stirred mechanically, and cooled to internal temperature ~1.5° C. Potassium permanganate (562.1 g, 3.56 mol) was then added in 7 equal portions (i.e. 80.3 g) every 15 min for 105 min. Water (0.5 L) was added and the resulting mixture was stirred at RT for 17 h. The mixture was cooled to 15° C. and a solution of sodium thiosulfate pentahydrate (883 g, 3.56 mol) in water (3 L) was added dropwise over 1 h, whilst maintaining internal temperature below 18° C. The resulting slurry was stirred for 1 h and the mixture left to stand at RT overnight. Solid had settled at the bottom of the flask and the solution was decanted and then concentrated to leave a residue. The remaining solid was treated with ethyl acetate (7 L) and water (2 L) and the mixture was filtered through Celite. The filtrate was combined with the residue isolated above. The mixture was separated and the aqueous layer extracted with ethyl acetate (2×1 L). The organics were combined and drying agent (Na$_2$SO$_4$) and decolorizing charcoal were added. The mixture was filtered through Celite and concentrated to dryness in vacuo to yield Intermediate 1b (260 g, 85%). $^1$H NMR (400 MHz, CDCl$_3$): 2.20-2.30 (1H, dddd, J=13.3, 10.0, 8.8, 4.5 Hz), 2.43-2.52 (1H, dddd, J=13.3, 7.2, 4.6, 4.6 Hz), 2.67-2.77 (1H, ddd, J=17.4, 10.1, 4.6 Hz), 2.78-2.88 (1H, ddd, J=17.4, 7.1, 4.6 Hz), 5.39-5.47 (1H, td, J=8.5, 4.5 Hz), 7.32-7.37 (1H, d, J=7.7 Hz), 7.44-7.49 (1H, t, J=7.6 Hz), 7.59-7.64 (1H, td, J=7.6, 1.4 Hz), 8.03-8.07 (1H, dd, J=7.7, 1.4 Hz).

c. 2,2,2-Trifluoro-N-((1S,4R)-4-hydroxy-1,2,3,4-tetrahydro-naphthalen-1-yl)-acetamide (Intermediate 1c)

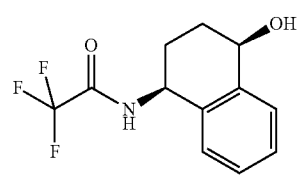 [SMILES: O=C(N[C@H]1CC[C@@H](O)c2ccccc21)C(F)(F)F]

A solution of Intermediate 1b (161 g, 624 mmol) in DMF (2 L) was vacuum degassed with argon. [N-[(1R,2R)-2-(Amino-κN)-1,2-diphenylethyl]-4-methylbenzenesulfonamidato-κN]chloro[(1,2,3,4,5,6-η)-1-methyl-4-(1-methylethyl)benzene]-ruthenium (CAS: 192139-92-7, 9.95 g, 15.6 mmol) was then added. Formic acid (57.5 g, 1.25 mol) was added slowly to ice cold triethylamine (126 g, 1.25 mol) with stirring, this was then added to the DMF solution. The resulting reaction mixture was heated to 50° C. (internal temperature) for 41 h with stirring. LCMS analysis of the reaction indicated it was incomplete, therefore a solution of formic acid (14.4 g, 313 mmol) was added slowly to ice cold triethylamine (31.6 g, 312 mmol), this was then added to the reaction mixture. Heating was continued for an additional 22 h. After cooling, the mixture was concentrated in vacuo to give an orange residue. The residue was diluted with ethyl acetate (1.5 L) and the solution washed with brine (2×0.5 L). The organics were dried (Na$_2$SO$_4$), filtered and concentrated in vacuo. Purification by column chromatography (Silica, 3 Kg, 0-50% ethyl acetate in cyclohexane) gave Intermediate 1c (118 g, 73%). 97.5 d.e.% determination by LCMS Rt 3.37 min, M-H 258 (93.7%, desired); Rt 3.25 min, M-H 258 (1.2%, trans isomer). $^1$H NMR (400 MHz, CDCl$_3$): 1.88-1.92 (1H, d, J=4.8 Hz), 1.98-2.18 (4H, m), 4.80-4.88 (1H, m), 5.165-5.24 (1H, m), 6.70-6.80 (1H, br s), 7.25-7.30 (1H, m), 7.30-7.40 (2H, m), 7.45-7.50 (1H, m).

d. (1R,4S)-4-Amino-1,2,3,4-tetrahydro-naphthalen-1-ol (Intermediate 1)

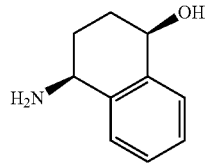

To a stirred solution of Intermediate 1c (117 g, 451 mmol) in methanol (0.7 L), 6N aqueous sodium hydroxide solution (190 mL, 1.14 mol) was added and stirred at RT for 20 h. The mixture was concentrated in vacuo and the residue was diluted with ethyl acetate (1 L) and water (0.5 L). Concentrated HCl solution (95 mL, 1.14 mol) was added slowly with stirring. Additional HCl was used to adjust the pH of the aqueous layer to pH=2. The mixture was then separated and the organic layer was extracted with HCl solution (2M aqueous, 3×500 mL). The combined aqueous layers were basified to pH~12, by addition of concentrated aqueous NH$_4$OH solution, and then extracted in to ethyl acetate (5×750 mL). The combined organic extracts were washed with brine (200 mL), dried (Na$_2$SO$_4$), filtered and concentrated in vacuo to give a solid (50.8 g). This material was recrystallized (cyclohexane/ethyl acetate[2:1], 350 mL) to provide Intermediate 1. (44.4 g, 60%). $^1$H NMR (400 MHz, d$_6$-DMSO): 1.66-1.90 (4H, m), 3.71-3.77 (1H, t, J=5.4 Hz), 4.46-4.54 (1H, t, J=5.4 Hz), 7.14-7.22 (2H, m), 7.32-7.38 (1H, m), 7.40-7.46 (1H, m).

Intermediate 2. (1S,4R)-4-[3-((S)-2-Methyl-piperidin-1-yl)-[1,2,4]triazolo[4,3-a]pyridin-6-yloxy]-1,2,3,4-tetrahydro-naphthalen-1-ylamine

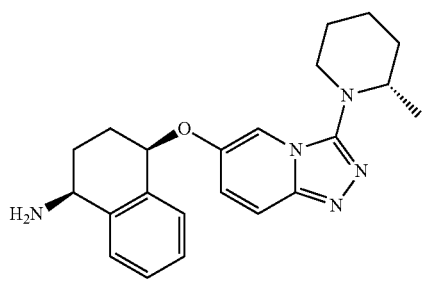 [SMILES: C[C@H]1CCCCN1c1nnc2ccc(O[C@@H]3CC[C@H](N)c4ccccc43)cn12]

a. (R)-Hydroxy-phenyl-acetate(S)-2-methyl-piperidinium (Intermediate 2a)

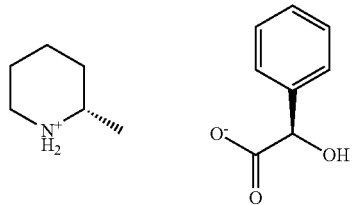

2-Methylpiperidine (99.7 g, 1.0 mol) [CAS 109-05-7] was dissolved in MeOH (100 mL) in a 2L Florentine flask and cooled in an ice bath. (R)-(−)-mandelic acid (152.9 g, 1.0 mol) [CAS 611-71-2] was then added and the reagents stirred with gentle heating until a homogenous solution resulted. The solution was left to cool, and Et$_2$O (900 mL) was added. The flask walls were scratched to aid crystallisation, and then stored in a fridge for 18 h. The resulting crystals were then filtered off, and washed with cold Et$_2$O. The product was recrystallized again from MeOH (100 mL) and Et$_2$O (500 mL) and left in a fridge for 48 h. The crystals were filtered off, washed with Et$_2$O and dried in a vacuum oven at 50° C. overnight to afford Intermediate 2a (66.97 g, 53%) as colourless crystals. $^1$H NMR (300 MHz, d$_6$-DMSO-d$_6$): 1.12 (3H, d, J=6.5 Hz), 1.20-1.57 (3H, m), 1.58-1.74 (3H, m), 2.72 (1H, dt, J=3.2, 12.4 Hz), 2.88-3.02 (1H, m), 3.06-3.18 (1H, m), 4.51 (1H, s), 7.11-7.19 (1H, m), 7.19-7.29 (2H, m), 7.33-7.42 (2H, m).

Diastereomeric purity was measured using Marfey's method; compound 2 (1 mg, 3.68 μmol) was dissolved in EtOAc (1 mL) and H$_2$O (1 mL) and Marfeys reagent was added (N$_\alpha$-(2,4-Dinitro-5-fluorophenyl)-L-alaninamide, FDAA [CAS 95713-52-3], 1 mg, 3.68 μmol) followed by saturated NaHCO$_3$ solution (50 μL) and heated to 50° C. for 1 hour. The mixture was then diluted with H$_2$O (1 mL) and subjected to analytical HPLC (Waters X-Select C18, 2.5 μm, 4.6×50 mm, 32-34% CH$_3$CN/H$_2$O (+0.1% formic acid), 16 min gradient, 1 mL/min, 340 nm). Rt 10.82 min, >99% d.e.

Racemic 2-methylpiperidine was also subjected to Marfey's method; HPLC: Rt 10.75 min (50%), 11.581 min (50%).

b. (S)-2-Methyl-piperidine-1-carbonyl chloride (Intermediate 2b)

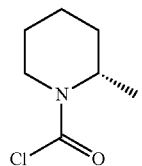

Intermediate 2a (12.0 g, 47.75 mmol) was treated with aqueous NaOH solution (1N; 96 mL, 96 mmol) and extracted into DCM (2×75 mL). This solution of (S)-2-methyl piperidine was transferred to a 3-necked RB flask, stirred under an inert atmosphere and cooled in an ice-bath before pyridine (11.6 mL, 143.72 mmol) was added followed by triphosgene (14.17 g, 47.75 mmol) during 30 min at <10° C. The cooling bath was removed after 30 min and the mixture stirred at RT for a further 3.5 hours. Reaction was quenched by very careful addition of aqueous HCl (1N, 300 mL) at 0-5° C. After 30 min the phases were separated and the aqueous layer extracted with DCM (2×100 mL). Combined DCM extracts were washed with brine, dried (MgSO$_4$), passed through a phase separation cartridge and concentrated in vacuo to give Intermediate 2b (8.6 g, >100% still containing some DCM). $^1$H NMR (300 MHz, CDCl$_3$): 1.25 (3H, d, J 6.8), 1.40-1.80 (6H, m), 3.0 (1H, br), 4.12-4.21 (1H, m), 4.56-4.67 (1H, m).

c. (S)-2-Methyl-piperidine-1-carboxylic acid N'-(5-fluoro-pyridin-2-yl)-hydrazide (Intermediate 2c)

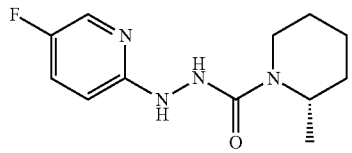 [SMILES: C[C@H]1CCCCN1C(=O)NNc1ccc(F)cn1]

A stirred solution of Intermediate 2b (17.20 g, assumed to be 95.49 mmol) and (5-fluoro-pyridin-2-yl)-hydrazine (12.14 g, 95.51 mmol) in DCM (300 mL) at RT was treated with DIPEA (34 mL, 195.18 mmol) during 5 min. This mixture was continued to be stirred at RT for 4 days before being added to water (500 mL) and phases separated. The aqueous layer was further extracted into DCM (4×100 mL), combined extracts washed with brine, dried (MgSO$_4$), passed through a phase separation cartridge and concentrated in vacuo to give a residual solid. This product was treated with Et$_2$O-pentane and the resultant solids filtered off and dried to give Intermediate 2c (18.74 g, 77%). LCMS (Method 3) Rt 2.26 min, m/z 253 [MH$^+$]. $^1$H NMR (300 MHz, CDCl$_3$): 1.23 (3H, d, J 6.9), 1.40-1.74 (6H, m), 2.97 (1H, td, J 13.1, 3.0), 3.82-3.91 (1H, m), 4.27-4.38 (1H, m), 6.54 (1H, s), 6.78 (1H, ddd, J 9.1, 3.7, 0.6), 7.30 (1H, ddd, J 9.1, 7.8, 2.9), 8.00 (1H, d, J 2.6).

d. 6-Fluoro-3-((S)-2-methyl-piperidin-1-yl)-[1,2,4]triazolo[4,3-α]pyridine (Intermediate 2d)

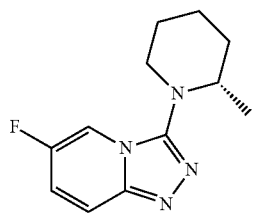 [SMILES: C[C@H]1CCCCN1c1nnc2ccc(F)cn12]

To a stirred solution of Intermediate 2c (14.70 g, 58.27 mmol), Ph$_3$P (30.56 g, 116.51 mmol) and Et$_3$N (33 mL, 236.76 mmol) in THF (300 mL) at RT was added hexachloroethane (27.60 g, 116.58 mmol) during 10 min before then heating at 60° C. overnight. The cooled mixture was filtered and concentrated in vacuo to give a residual oil which was dissolved in DCM (200 mL) and extracted into dilute HCl (2M) until most product had been removed from the DCM phase by LCMS. These aqueous extracts were treated with solid NaOH (with cooling) to achieve ~pH9 and extracted into DCM. Combined DCM extracts were washed with brine, dried (MgSO$_4$), passed through a phase separation cartridge and concentrated in vacuo to give Intermediate 2d (11.30 g, 82%). LCMS (Method 3) Rt 2.99 min, m/z 235 [MH$^+$]. $^1$H NMR (300 MHz, d$_6$-d$_6$-DMSO): 0.89 (3H, d, J 6.3), 1.40-1.88 (6H, m), 2.85-2.96 (1H, m), 3.18 (1H, dt, J 12.0, 4.5), 3.28-3.35 (1H, m), 7.42 (1H, ddd, J 10.0, 8.0, 2.3), 7.76 (1H, ddd, J 10.0, 4.9, 0.9), 8.31-8.35 (1H, m).

e. (1S,4R)-4-[3-((S)-2-Methyl-piperidin-1-yl)-[1,2,4]triazolo[4,3-a]pyridin-6-yloxy]-1,2,3,4-tetrahydro-naphthalen-1-ylamine (Intermediate 2)

Sodium hydride (60% dispersion in oil, 12 g, 300 mmol) was suspended in DMF (800 mL) and cooled to 0° C. using an ice bath. (24.45 g, 150 mmol) was then added in small portions under N$_2$ and the resulting opaque brown suspension was stirred at RT for 45 min (CARE: gas evolution). A solution of Intermediate 2d (35.1 g, 150 mmol) in dry DMF (200 mL) was added and the solution stirred at RT for 18 h. The solution was concentrated in vacuo, the residue was poured into a mixture of brine/1N aqueous NaOH/H$_2$O (1:1:1; 200 mL); the product was extracted using mixture of EtOAc and Me-THF (300 mL×5). The organic extracts were combined, washed with a small amount of brine, dried over MgSO$_4$ and concentrated under reduced pressure. The product was purified by FCC, eluting with 0-20% [2M NH$_3$ in MeOH] in DCM, to provide the title compound (27.1 g, 48%) as a pale brown foam. LCMS (Method 3): Rt 2.29 min, m/z 378 [MH$^+$].

Intermediate 3. (1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-ylamine

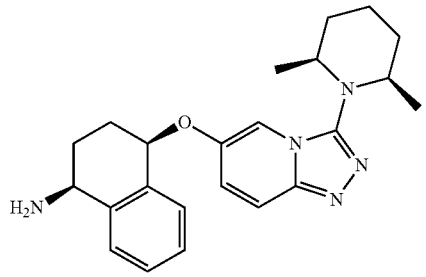 [SMILES: C[C@@H]1CCC[C@H](C)N1c1nnc2ccc(O[C@@H]3CC[C@H](N)c4ccccc43)cn12]

a. (2S,6R)-2,6-Dimethyl-piperidine-1-carbonyl chloride (Intermediate 3a)

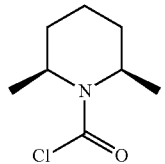

To a solution of triphosgene (20.8 g, 70.0 mmol) in DCM (400 mL) at 5° C. was added pyridine (16.2 mL, 200 mmol) dropwise over 10 min, maintaining the temperature below 10° C. The solution was then stirred between 5-10° C. for 1 h, then cis-2,6-dimethyl piperidine (CAS: 766-17-6, 27.0 mL, 200 mmol) was added dropwise over 10 min and the resulting red solution stirred at RT for 4 days (reaction complete within <4 h). The solution was cooled to 3° C., then a pre-cooled (3°

C.) 1M aqueous HCl solution (400 mL) was added and the mixture stirred at 5° C. for 30 min. The mixture was separated and the aqueous layer was extracted with DCM (200 mL), then the combined organic extracts passed through a hydrophobic fit and concentrated under vacuum affording Intermediate 3a as a red oil (31.5 g, 90%). $^1$H NMR (300 MHz, CDCl$_3$): 1.30 (6H, d, J=7.09 Hz), 1.49-1.87 (6H, m), 4.46-4.56 (2H, m).

b. (2S,6R)-2,6-Dimethyl-piperidine-1-carboxylic acid N'-(5-fluoro-pyridin-2-yl)-hydrazide (Intermediate 3b)

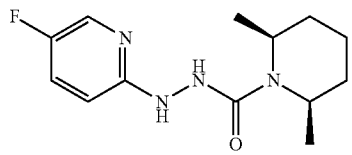 [SMILES: C[C@@H]1CCC[C@H](C)N1C(=O)NNc1ccc(F)cn1]

A solution of (5-fluoro-pyridine-2-yl)-hydrazine (21.7 g, 171 mmol), Intermediate 3a (31.5 g, 180 mmol) and DIPEA (44.7 mmol, 256 mmol) in DCM (350 mL) was stirred at RT for 4 days. Water (350 mL) was added, then the aqueous layer extracted with DCM (100 mL). The combined organic extracts were passed through a hydrophobic fit and concentrated under vacuum to leave a solid. Trituration with diethyl ether/pentane (1:4, 150 mL), and drying under vacuum at 50° C., gave Intermediate 3b (31.7 g, 70%, ~90% purity). LCMS: Rt 2.58 min, m/z 289 [MH$^+$]. $^1$H NMR (300 MHz, CDCl$_3$): 1.29 (6H, d, J=7.0 Hz), 1.45-1.89 (6H, m), 4.26 (2H, apparent quin, J=6.5 Hz), 6.53 (1H, s), 6.65 (1H, br s), 6.77 (1H, dd, J=9.0, 3.6 Hz), 7.29-7.28 (1H, ddd, J=9.0, 8.0, 3.0), 8.02 (1H, d, J=2.9 Hz).

c. 3-((2S,6R)-2,6-Dimethyl-piperidine-1-yl)-6-fluoro-[1,2,4]triazolo[4,3-a]pyridine (Intermediate 3c)

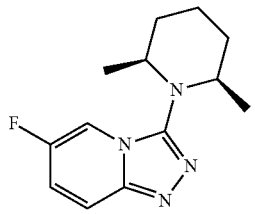 [SMILES: C[C@@H]1CCC[C@H](C)N1c1nnc2ccc(F)cn12]

To a suspension of Intermediate 3b (27.4 g, 102.9 mmol) and pyridine (25 mL, 309.1 mmol) in toluene (250 mL) at 50° C. was added POCl$_3$ (11.0 mL, 118 mmol) in 3 portions at 30 s intervals. (CARE: exotherm to 70° C.). The brown suspension was stirred at 50° C. for 1 h, then cooled to RT. Water (100 mL) and sat. aqueous NaHCO$_3$ solution (100 mL) were added (CARE: gas evolution) and the mixture stirred at RT for 30 min. The aqueous was extracted with EtOAc (2×250 mL), then the combined organics washed with brine (250 mL), dried (Na$_2$SO$_4$), filtered and concentrated in vacuo to leave a brown oil (26.3 g, overweight). The oil was redissolved in MeOH (150 mL) then charcoal (6 g) was added and the mixture swirled for 30 min. The suspension was filtered through Celite and the filtercake washed with MeOH (25 mL). The filtrate was concentrated in vacuo to leave a red oil. this was azeotroped with pentane (25 mL) (24.0 g). The solid was slurried in diethyl ether/pentane (1:1, 40 mL), filtered and dried in vacuo to leave Intermediate 3c (20.6 g, 81%). The mother liquor was concentrated in vacuo, the residue dissolved in hot cyclohexane (50° C., 30 mL), then cooled to RT and allowed to stand for over the weekend. The mixture was filtered, the solid washed with cyclohexane (5 mL) then dried in vacuo at 45° C. to leave additional Intermediate 3c (1.8 g, 6%). LCMS: Rt 3.30 min, m/z 249 [MH$^+$]. $^1$H NMR (300 MHz, CDCl$_3$): 0.68 (6H, d, J=6.2 Hz), 1.36-1.49 (2H, m), 1.52-1.68 (1H, m), 1.75-1.90 (3H, m), 3.29-3.40 (2H, m), 7.16 (1H, ddd, J=10.0, 7.6, 2.3 Hz), 7.67 (1H, dd, J=10.0, 4.7 Hz), 8.03 (1H, t, J=2.7 Hz).

d. (1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-ylamine (Intermediate 3)

To a solution of Intermediate 1 (6.59 g, 40.4 mmol) in dry DMF (80 mL) under N$_2$ was added sodium hydride (60% dispersion in oil, 3.20 g, 80.0 mmol) and the resulting opaque brown solution was stirred at RT for 45 min (CARE: gas evolution). A solution of Intermediate 3c (9.93 g, 40.0 mmol) in dry DMF (20 mL) was added and the solution stirred at RT for 24 h. The reaction was carefully quenched with saturated NH$_4$Cl (CARE: gas evolution) solution and H$_2$O. The brown mixture was stirred for 30 min. The mixture was concentrated in vacuo and dissolved in MeOH (125 mL), charcoal was added to the solution and the mixture was stirred at RT for 1 h, and then filtered through Celite. The solution was evaporated under reduced pressure to afford a residue, which was suspended in H$_2$O (100 mL) and extracted with EtOAc (3×100 mL). The combined organic extracts were washed with brine (75 mL), dried over Na$_2$SO$_4$, filtered and concentrated in vacuo to leave a brown foam (14.6 g, 93%). The foam was triturated with pentane (2×75 mL) using sonication and stirring, the solution was decanted and the solid was left to dry under vacuum and at RT affording a solid (14.2 g, 90%). LCMS (Method 3): Rt 2.32 min, m/z 392 [Mf1$^+$].

Intermediate A. Methanesulfonic acid 2-[5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-3-isopropyl-[1,4']bipyrazolyl-1'-yl]-ethyl ester

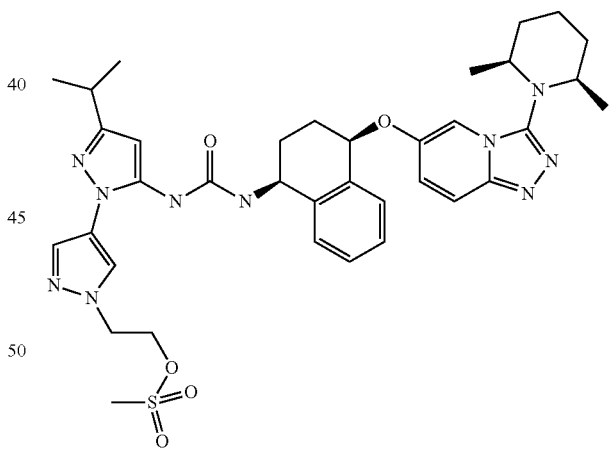

a. 2-(4-Iodo-pyrazol-1-yl)-ethanol (Intermediate Aa)

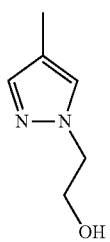

A solution of 4-iodopyrazole (14.3 g, 73.9 mmol) and ethylene carbonate (6.83g, 77.6 mmol) in DMF (50 mL) was stirred at 125° C. for 24 h. The cooled solution was concentrated under vacuum to leave a brown oil. The residue was purified by FCC using 30-70% EtOAc in DCM to give the title compound (9.36 g, 53%). LCMS (Method 3): Rt 2.24 min, m/z 239 [MH⁺].

b. 2-(5-Amino-3-isopropyl-[1,4']bipyrazolyl-1'-yl)-ethanol (Intermediate Ab)

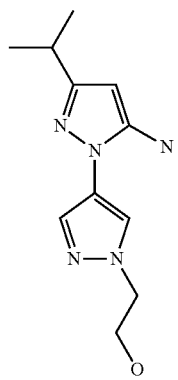 [SMILES: CC(C)c1cc(N)n(-c2cnn(CCO)c2)n1]

A mixture of 5-isopropyl-2H-pyrazol-3-ylamine (550 mg, 4.4 mmol), Intermediate Aa (1.0 g, 4.2 mmol), copper (I) iodide (40 mg, 0.21 mmol), (1S,2S)—N.N'-dimethyl cyclohexane-1,2-diamine (119 mg, 0.84 mmol) and potassium carbonate (1.22 g, 8.8 mmol) in Xylene (5 mL) was de-gassed and flushed with argon (3×). The reaction mixture was heated at 110° C. for 18 h. The mixture was poured onto a SCX-2 and eluted with MeOH and 2M NH3 in MeOH. The basic fractions were evaporated under reduced pressure to afford a brown gum. The residue obtained was purified by FCC, using 0-10% MeOH in DCM to afford the title compound (0.25 g, 25%). LCMS (Method 3): Rt 1.43 min, m/z 236 [MH₊].

c. [1'-(2-Hydroxy-ethyl)-3-isopropyl-1'H-[1,4']bipyrazolyl-5-yl]-carbamic acid 2,2,2-trichloro-ethyl ester (Intermediate Ac)

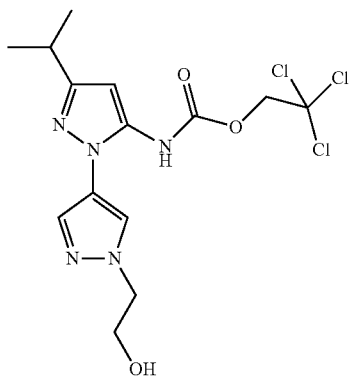 [SMILES: CC(C)c1cc(NC(=O)OCC(Cl)(Cl)Cl)n(-c2cnn(CCO)c2)n1]

A solution of Intermediate Ab (250 mg, 1.06 mmol) in EtOAc (3 mL) was treated with aqueous NaOH (1M, 1.9 mmol), followed by 2,2,2-trichloroethyl chloroformate (154 μL, 1.16 mmol) and the reaction mixture was stirred at RT for 1 h. The mixture was partitioned between EtOAc (10 mL) and water (10 mL). The layers were separated and the aqueous layer was extracted with a further 10 mL EtOAc. The combined organic layers were dried (Na₂SO₄), filtered and concentrated in vacuo. The residue was purified by FCC, using 0-40% EtOAc in DCM to afford the title compound as a colorless oil (300 mg, 70%). LCMS (Method 3): Rt 3.42 min, m/z 410, 412 [MH⁺].

d. 1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-[1'-(2-hydroxy-ethyl)-3-isopropyl-1'H-[1,4']bipyrazolyl-5-yl]-urea. (Intermediate Ad)

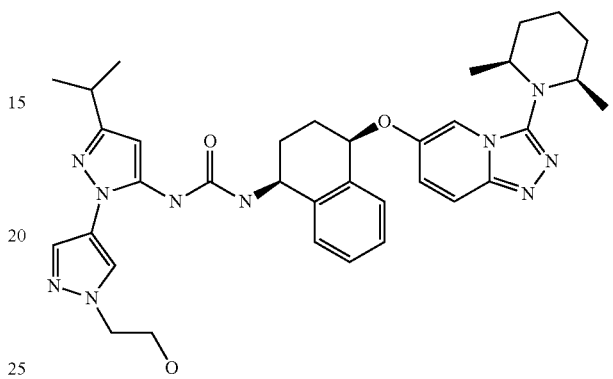

A mixture of Intermediate 3 (286 mg, 0.730 mmol), Intermediate Ac (300 mg, 0.730 mmol) and DIPEA (183 μL, 1.09 mmol) in dioxane (3 mL) was stirred at 70° C. O/N. The reaction mixture was poured on a SCX-2 cartridge eluting with MeOH and 2M NH3 in MeOH. The basic fractions were concentrated in vacuo and the resultant residue was purified by FCC eluting with 0-100% MeOH in DCM to afford the title compound (375 mg, 80%). LCMS (Method 3): Rt 3.47 min, m/z 653 [MH⁺].

e. Methanesulfonic acid 2-[5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-3-isopropyl-[1,4']bipyrazolyl-1'-yl]-ethyl ester (Intermediate A)

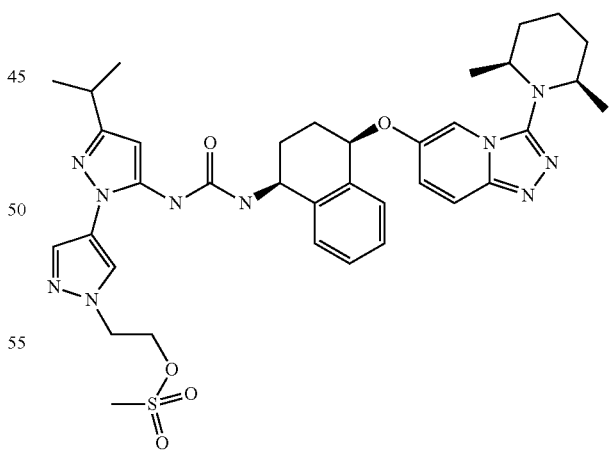

A mixture of Intermediate Ad (375 mg, 0.575 mmol), methanesulfonyl chloride (182 μL, 1.72 mmol) and DIPEA (383 μL, 2.3 mmol) in DCM (5 mL) was stirred at RT for 60 min. The reaction mixture was partitioned between DCM and water. The organic layer was washed with brine, separated through a phase separating cartridge and concentrated in vacuo to afford the title compound (400 mg, 95%). LCMS (Method 3): Rt 3.68 min, m/z 731 [MH⁺].

Intermediate B. Methanesulfonic acid 2-[3-isopropyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester

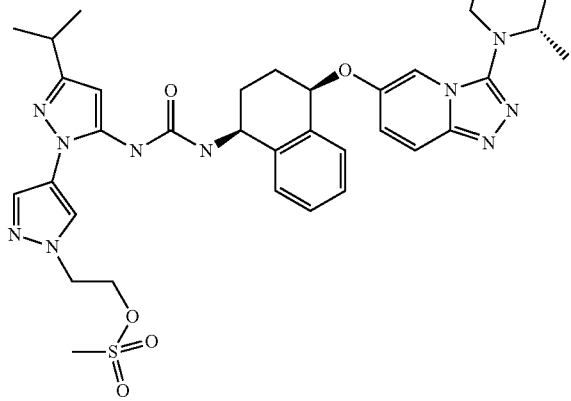

a. 1-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-3-[1'-(2-hydroxy-ethyl)-3-isopropyl-1'H-[1,4']bipyrazolyl-5-yl]-urea.
(Intermediate Ba)

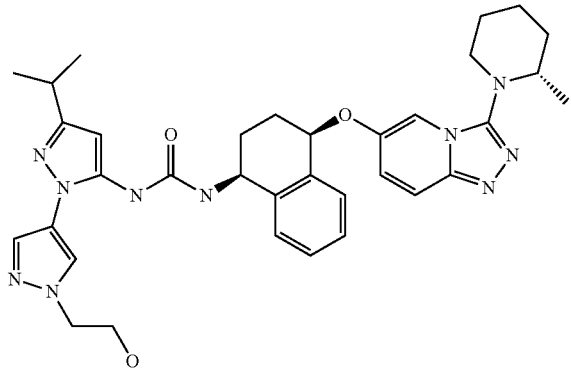 [SMILES: CC(C)c1cc(NC(=O)N[C@H]2CC[C@@H](Oc3ccc4nnc(N5CCCC[C@@H]5C)n4c3)c3ccccc32)n(-c2cnn(CCO)c2)n1]

The title compound was prepared starting from Intermediate 2 (150 mg, 0.397 mmol), and Intermediate Ac (163 mg, 0.397 mmol) by using an analogous procedure to that described for Intermediate A step d. LCMS (Method 3): Rt 3.21 min, m/z=639 [MH$^+$].

b. Methanesulfonic acid 2-[5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-3-isopropyl-[1,4']bipyrazolyl-1'-yl]-ethyl ester (Intermediate B)

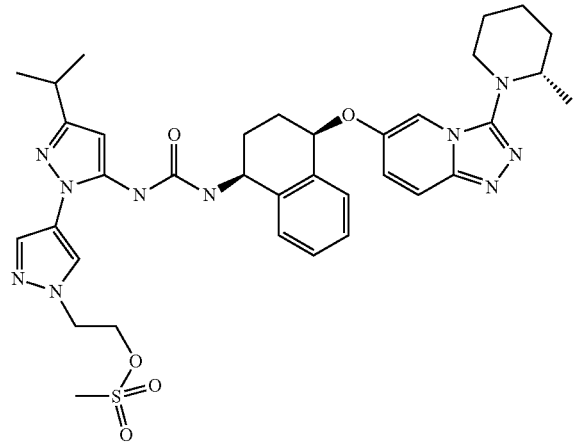 [SMILES: CC(C)c1cc(NC(=O)N[C@H]2CC[C@@H](Oc3ccc4nnc(N5CCCC[C@@H]5C)n4c3)c3ccccc32)n(-c2cnn(CCOS(C)(=O)=O)c2)n1]

The title compound was prepared starting from Intermediate Ba (217 mg, 0.340 mmol) by using an analogous procedure to that described for Intermediate A step d. LCMS (Method 3): Rt 3.40 min, m/z=717 [MH$^+$].

Intermediate C. Methanesulfonic acid 2-[5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-3-ethyl-[1,4']bipyrazolyl-1'-yl]-ethyl ester

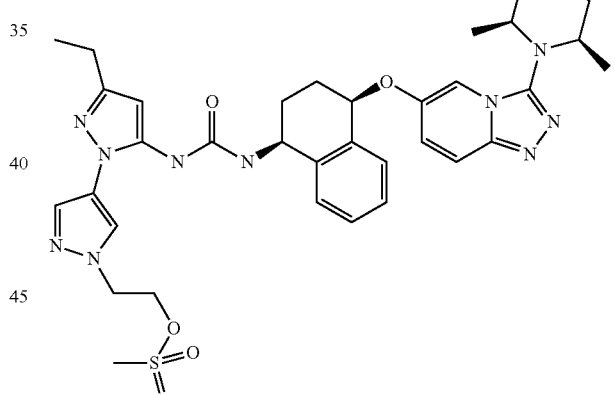

a. 2-(5-Amino-3-ethyl-[1,4']bipyrazolyl-1'-yl)-etha (Intermediate Ca)

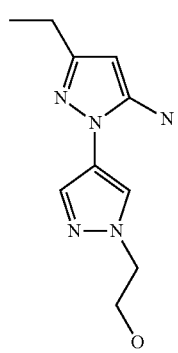 [SMILES: CCc1cc(N)n(-c2cnn(CCO)c2)n1]

The title compound was prepared starting from Intermediate Aa (1 g, 8.99 mmol) by using an analogous procedure to that described for Intermediate A step b. LCMS (Method 3): Rt 0.41 min, m/z=222 [MH⁺].

b. [1'-(2-Hydroxy-ethyl)-3-ethyl-1'H-[1,4']bipyrazolyl-5-yl]-carbamic acid 2,2,2-trichloro-ethyl ester (Intermediate Cb)

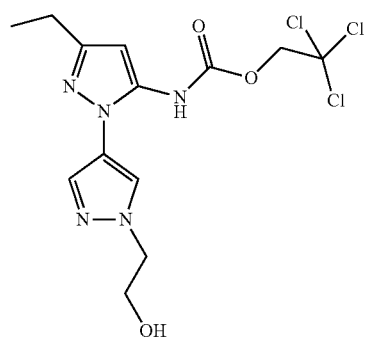 [SMILES: CCc1cc(NC(=O)OCC(Cl)(Cl)Cl)n(-c2cnn(CCO)c2)n1]

The title compound was prepared starting from Intermediate Ca (653 mg, 2.95 mmol) by using an analogous procedure to that described for Intermediate A step c. LCMS (Method 3): Rt 3.22 min, m/z=396, 398 [MH⁺].

c. 1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-[1'-(2-hydroxy-ethyl)-3-ethyl-1'H-[1,4']bipyrazolyl-5-yl]-urea. (Intermediate Cc)

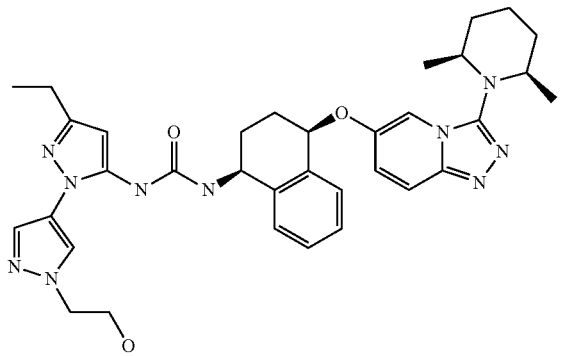 [SMILES: CCc1cc(NC(=O)N[C@H]2CC[C@@H](Oc3ccc4nnc(N5[C@H](C)CCC[C@@H]5C)n4c3)c3ccccc32)n(-c2cnn(CCO)c2)n1]

The title compound was prepared starting from Intermediate 3 (900 mg, 2.27 mmol), and Intermediate Cb (889 mg, 2.27 mmol) by using an analogous procedure to that described for Intermediate A step d. LCMS (Method 3): Rt 3.30 min, m/z=639 [MH⁺].

d. Methanesulfonic acid 2-[5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-3-ethyl-[1,4']bipyrazolyl-1'-yl]ethyl ester (Intermediate C)

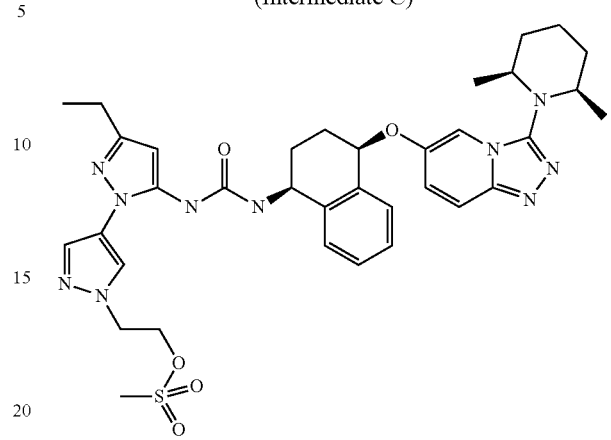

The title compound was prepared starting from Intermediate Cc (200 mg, 0.31 mmol) by using an analogous procedure to that described for Intermediate A step e. LCMS (Method 3): Rt 3.48 min, m/z=717 [MH⁺].

Intermediate D. Methanesulfonic acid 2-[3-ethyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester

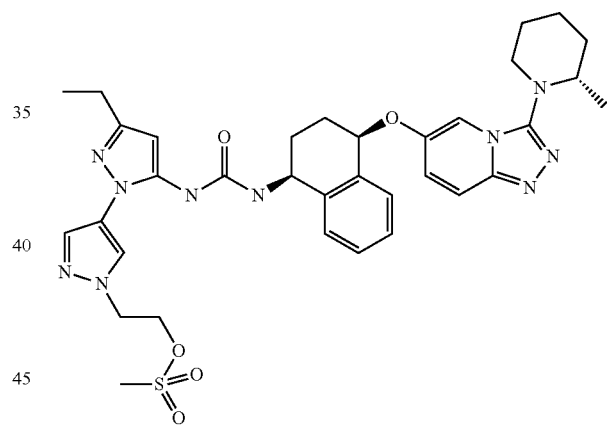

a. 1-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-3-[1'-(2-hydroxy-ethyl)-3-ethyl-1'H-[1,4']bipyrazolyl-5-yl]-urea. (Intermediate Da)

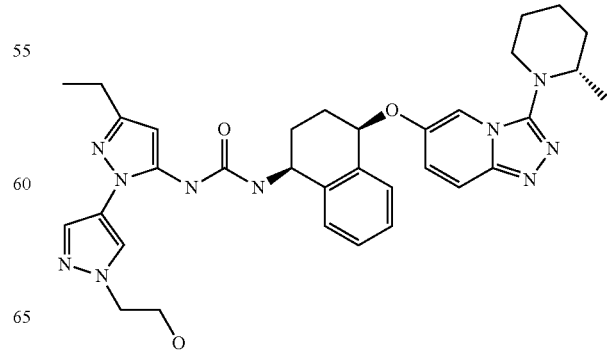

The title compound was prepared starting from Intermediate 2 (150 mg, 0.397 mmol), and Intermediate Cb (157 mg, 0.397 mmol) by using an analogous procedure to that described for Intermediate A step d. LCMS (Method 3): Rt 3.10 min, m/z=625 [MH+].

b. Methanesulfonic acid 2-[5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-3-ethyl-[1,4]bipyrazolyl-1'-yl]-ethyl ester (Intermediate D)

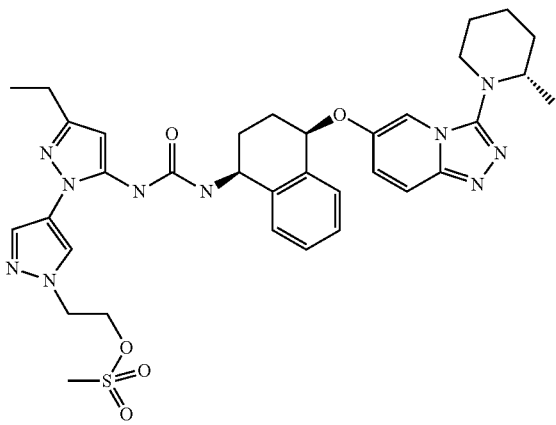 [SMILES: CCc1cc(NC(=O)N[C@H]2CC[C@@H](Oc3ccc4nnc(N5CCCC[C@@H]5C)n4c3)c3ccccc32)n(-c2cnn(CCOS(C)(=O)=O)c2)n1]

The title compound was prepared starting from Intermediate Da (140 mg, 0.224 mmol) by using an analogous procedure to that described for Intermediate A step e. LCMS (Method 3): Rt 3.27 min, m/z=703 [MH+].

Intermediate E. Methanesulfonic acid 2-{3-[3-methyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-phenoxy}-ethyl ester

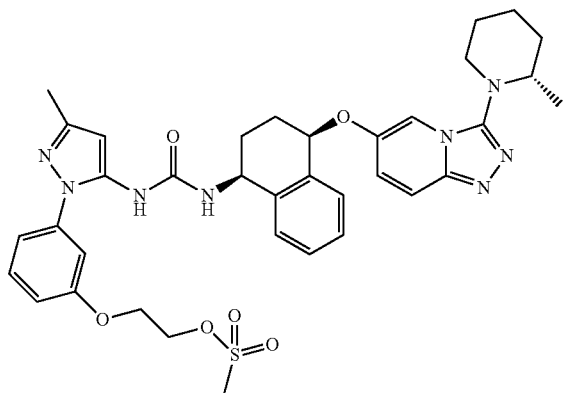 [SMILES: Cc1cc(NC(=O)N[C@H]2CC[C@@H](Oc3ccc4nnc(N5CCCC[C@@H]5C)n4c3)c3ccccc32)n(-c2cccc(OCCOS(C)(=O)=O)c2)n1]

a. 3-(5-Amino-3-methyl-pyrazol-1-yl)-phenol (Intermediate Ea)

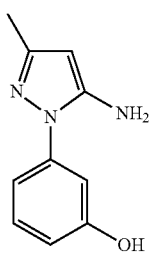

The title compound was prepared starting from 5-methyl-2H-amino pyrazol (500 mg, 5.1 mmol) and 3-iodo-phenol (1.25 g, 5.7 mmol) by using an analogous procedure to that described for Intermediate A step b. LCMS (Method 3): Rt 0.99 min, m/z=190 [MH+].

b. 5-methyl-2-{3-[2-(tetrahydro-pyran-2-yloxy)-ethoxy]-phenyl}-2H-pyrazol-3-ylamine (Intermediate Eb)

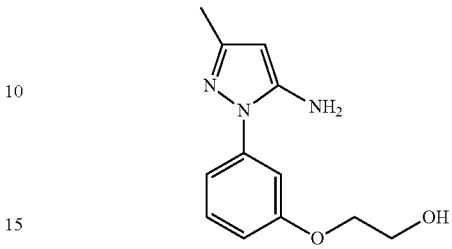

DIAD (629 µL, 3.98 mmol) was added slowly to a solution of Intermediate Ea (378 mg, 1.99 mmol), 2-(tetrahydro-pyran-2-yloxy)-ethanol (270 µL, 2.98 mmol) and triphenylphosphine (1.04 g, 3.98 mmol) in THF (15.0 mL) and stirred for 1 h. The reaction mixture was poured on a SCX-2 cartridge eluting with MeOH and 2M NH3 in MeOH. The basic fractions were concentrated in vacuo and the resultant residue was purified by FCC eluting with 0-60% EtOAc in DCM to afford the title compound (280 mg, 60%) as a pale yellow gum. $^1$H NMR (300 MHz, CDCl$_3$): 2.05 (3H, s), 3.71 (2H, q, J=5.09 Hz), 4.01 (2H, t, J=5.09 Hz), 4.86 (1H, t, J=5.875 Hz), 5.23 (2H, br s), 5.30 (1H, s), 6.79-685 (1H, m), 7.08-7.15 (2H, m), 7.27-7.36 (1H, m).

c. (5-tert-Butyl-2-{3-[2-(tetrahydro-pyran-2-yloxy)-ethoxy]-phenyl}-2H-pyrazol-3-yl)-carbamic acid 2,2,2-trichloro-ethyl ester (Intermediate Ec)

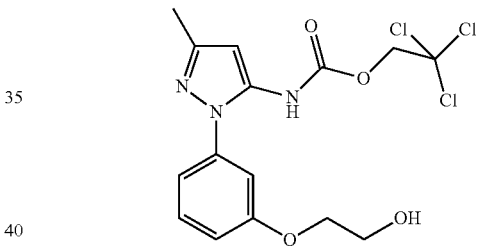

The title compound was prepared starting from 2,2,2-trichloroethylchloroformate and Intermediate Eb by using an analogous procedure to that described for Example A step c. LCMS (Method 3): Rt 3.41, m/z 408, 410 [MH+].

d. 1-{2-[3-(2-Hydroxy-ethoxy)-phenyl]-5-methyl-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate Ed)

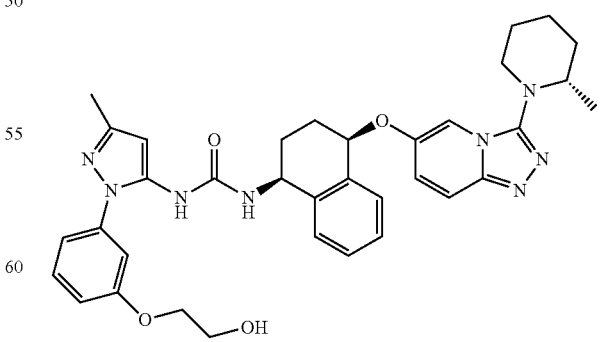

The title compound was prepared starting from Intermediate Ec and Intermediate 2 by using an analogous procedure to that described for Intermediate A step d. LCMS (Method 3): Rt 3.22 min, m/z=637 [MH+].

e. Methanesulfonic acid 2-{3-[3-methyl-5-(3-{(1S, 4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-phenoxy}-ethyl ester (Intermediate E)

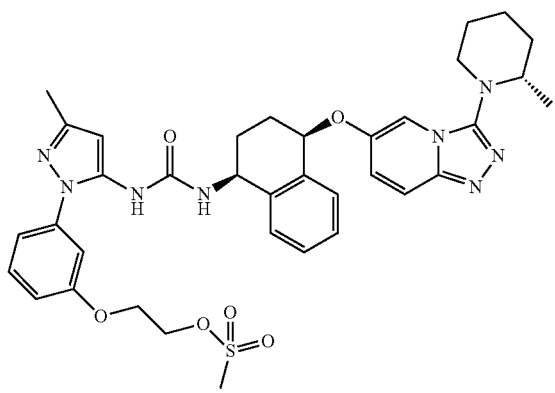 [SMILES: Cc1cc(NC(=O)N[C@H]2CC[C@@H](Oc3ccc4nnc(N5CCCC[C@@H]5C)n4c3)c3ccccc32)n(-c2cccc(OCCOS(C)(=O)=O)c2)n1]

The title compound was prepared starting from Intermediate 4b and Intermediate 1g by using an analogous procedure to that described for Intermediate A step e. LCMS (Method 3): Rt 3.98 min, m/z=715 [MH⁺].

Intermediate F. Methanesulfonic acid 2-[5-(3-{(1S, 4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-3-isopropyl-[1,4']bipyrazolyl-1'-yl]-ethyl ester

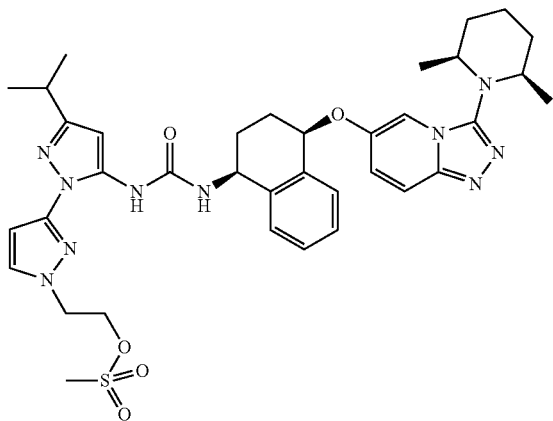 [SMILES: CC(C)c1cc(NC(=O)N[C@H]2CC[C@@H](Oc3ccc4nnc(N5[C@H](C)CCC[C@@H]5C)n4c3)c3ccccc32)n(-c2ccn(CCOS(C)(=O)=O)n2)n1]

a. 2-(3-Iodo-pyrazol-1-yl)-ethanol (Intermediate Fa)

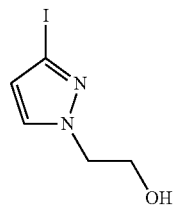

A solution of 3-iodo-1H-pyrazole (500 mg, 2.6 mmol) and ethylene carbonate (238 mg, 2.70 mmol) was formed in DMF (5 mL) and heated at 150° C. for 3 h. The mixture was allowed to cool then evaporated under vacuum to remove the solvent. Purification of the residue by FCC eluting with a gradient of 0-100% EtOAc in cyclohexane gave crude title compound (444 mg, 72%) as a brown oil. LCMS (Method 3): Rt 2.17 min, m/z 239 [MH⁺].

b. 2-(5-Amino-3-isopropyl-[1,3']bipyrazolyl-1'-yl)-ethanol (Intermediate Fb)

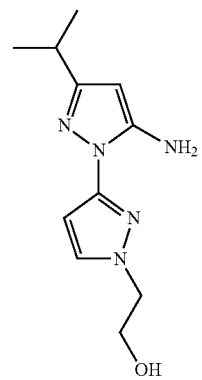 [SMILES: CC(C)c1cc(N)n(-c2ccn(CCO)n2)n1]

A mixture of 5-isopropyl-2H-pyrazol-3-ylamine (376 mg, 3.0 mmol), Intermediate Fa (650 mg, 2.73 mmol), copper (I) iodide (52 mg, 0.273 mmol), (1S,2S)—N,N'-dimethyl cyclohexane-1,2-diamine (78 mg, 0.546 mmol) and potassium carbonate (792 mg, 5.73 mmol) in Toluene (6 mL) was de-gassed and flushed with argon (3×). The reaction mixture was microwaved at 150° C. for 3 h. The mixture was poured onto a SCX-2 and eluted with MeOH and 2M NH3 in MeOH. The basic fractions were evaporated under reduced pressure to afford a brown gum. The residue obtained was purified by FCC, using 0-10% MeOH in DCM, to afford the title compound (0.28 g, 30%). LCMS (Method 3): Rt 1.92 min, m/z 236 [MH⁺].

c. [1'-(2-Hydroxy-ethyl)-3-isopropyl-1'H-[1,3']bipyrazolyl-5-yl]-carbamic acid 2,2,2-trichloro-ethyl ester (Intermediate Fc)

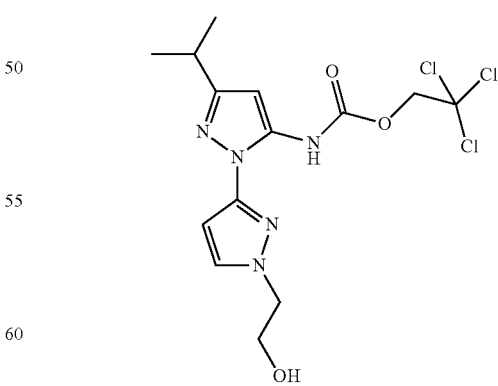

A solution of Intermediate Fb (272 mg, 1.16 mmol) in EtOAc (3 mL) was treated with aqueous NaOH (1M, 2.10 mmol), followed by 2,2,2-trichloroethyl chloroformate (167 µL, 1.21 mmol) and the reaction mixture was stirred at RT for 1 h. The mixture was partitioned between EtOAc (10 mL) and water (10 mL). The layers were separated and the aqueous layer was extracted with a further 10 mL EtOAc. The combined organic layers were dried (Na$_2$SO$_4$), filtered and concentrated in vacuo. The residue was purified by FCC, using 10-100% EtOAc in DCM, to afford the title compound as a colorless oil (124 mg, 40%). LCMS (Method 3): Rt 3.98 min, m/z 410, 412 [MH$^+$].

d. 1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-[1'-(2-hydroxy-ethyl)-3-isopropyl-1'H-[1,3']bipyrazolyl-5-yl]urea. (Intermediate Fd)

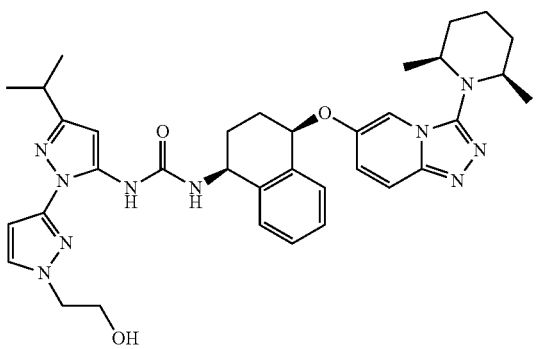 [SMILES: CC(C)c1cc(NC(=O)N[C@H]2CC[C@@H](Oc3ccc4nnc(N5[C@H](C)CCC[C@@H]5C)n4c3)c3ccccc32)n(-c2ccn(CCO)n2)n1]

A mixture of Intermediate 3 (119 mg, 0.303 mmol), Intermediate Fc (124.5 mg, 0.303 mmol) and DIPEA (76 µL, 0.454 mmol) in dioxane (2 mL) was stirred at 60° C. overnight. The reaction mixture was poured on a SCX-2 cartridge eluting with MeOH and 2M NH$_3$ in MeOH. The basic fractions were concentrated in vacuo and the resultant residue was purified by FCC, eluting with 0-20% MeOH in DCM, to afford the title compound (100 mg, 60%). LCMS (Method 3): Rt 3.70 min, m/z 653.4 [MH$^+$].

e. Methanesulfonic acid 2-[5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-3-isopropyl-[1,3']bipyrazolyl-1'-yl]ethyl ester (Intermediate F)

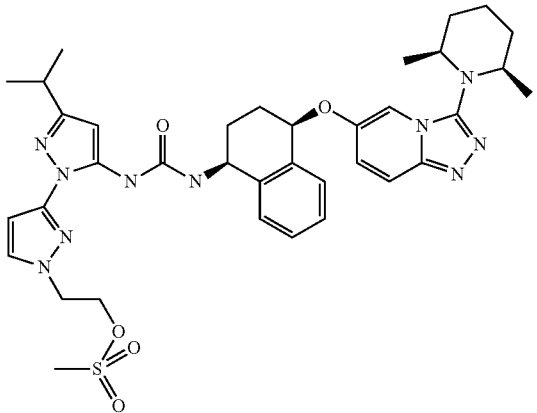 [SMILES: CC(C)c1cc(NC(=O)N[C@H]2CC[C@@H](Oc3ccc4nnc(N5[C@H](C)CCC[C@@H]5C)n4c3)c3ccccc32)n(-c2ccn(CCOS(C)(=O)=O)n2)n1]

A mixture of Intermediate Fd (100 mg, 0.153 mmol), methanesulfonyl chloride (32 µL, 0.46 mmol) and DIPEA (103 µL, 0.61 mmol) in DCM (5 mL) was stirred at RT for 60 min. The reaction mixture was partitioned between DCM and water. The organic layer was washed with brine, separated through a phase separating cartridge and concentrated in vacuo to afford the title compound (112 mg, quantitative). LCMS (Method 3): Rt 3.98 min, m/z 731 [MH$^+$].

Intermediate G. Methanesulfonic acid 2-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester

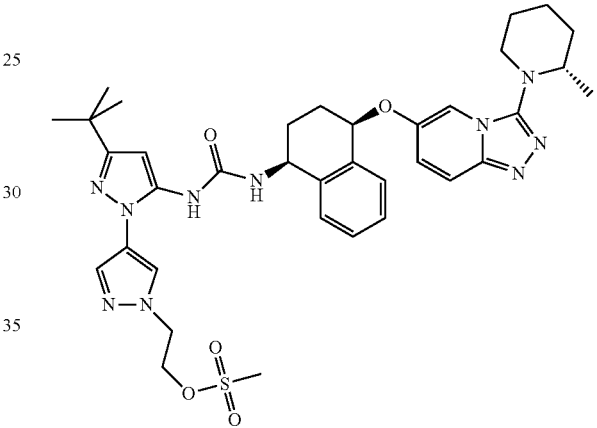

a. 2-(4-Iodo-pyrazol-1-yl)-ethanol (Intermediate Ga)

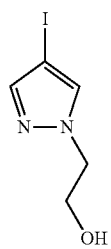

A solution of 4-iodopyrazole (14.3 g, 73.9 mmol) and ethylene carbonate (6.83 g, 77.6 mmol) in DMF (50 mL) was stirred at 125° C. for 24 h. The cooled solution was concentrated under vacuum to leave a brown oil. The residue was purified by FCC, using 30-70% EtOAc in DCM, to give the title compound (9.36 g, 53%). LCMS (Method 1): Rt 2.24 min, m/z 239 [MH$^+$].

b. 2-(5-Amino-3-tert-butyl-[1,4']bipyrazolyl-1'-yl)-ethanol (Intermediate Gb)

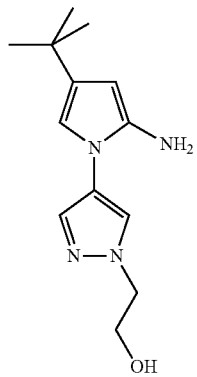 [SMILES: CC(C)(C)c1cc(N)n(-c2cnn(CCO)c2)c1]

A solution of Intermediate Ga (9.36 g, 39.3 mmol) in xylene (40 mL) was purged with argon for 30 min. In a separate flask, a mixture of 3-tert-butyl-1H-pyrazole-5-amine (5.75 g, 41.3 mmol), copper iodide (375 mg, 1.97 mmol), trans—N,N-dimethylcyclohexane-1,2-diamine (1.12 g, 7.87 mmol) and potassium carbonate (11.4 g, 82.6 mmol) was de-gassed and purged with argon three times. The xylene solution was then added, via cannula to the flask and the resultant brown solution was heated at reflux for 3 h. The cooled solution was diluted with EtOAc (40 mL) and washed with saturated aqueous ammonia solution/water (1:1, 40 mL). The aqueous layer was extracted with EtOAc (40 mL) and the combined organics were washed with water (40 mL) and brine (40 mL), dried (Na$_2$SO$_4$), filtered and concentrated in vacuo to afford a solid. This was purified by FCC, using 4-7.5% MeOH in DCM to afford the title compound (6.01 g, 61%). LCMS (Method 1): Rt 1.84 min, m/z 250 [MH$^+$].

b. [3-tert-Butyl-1'-(2-hydroxy-ethyl)-1'H-[1,4']bipyrazolyl-5-yl]-carbamic acid 2,2,2-trichloro-ethyl ester (Intermediate Gc)

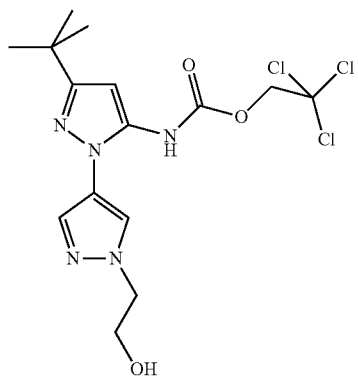 [SMILES: CC(C)(C)c1cc(NC(=O)OCC(Cl)(Cl)Cl)n(-c2cnn(CCO)c2)n1]

To a solution of Intermediate Gb (6.01 g, 24.1 mmol) and aqueous NaOH solution (36 mL, 36 mmol) in EtOAc (40 mL) was added 2,2,2-trichloroethyl chloroformate (4.15 mL, 30.1 mmol). The reaction mixture was stirred at RT for 16 h. The layers were separated and the aqueous layer was extracted with EtOAc (40 mL). The combined organics were washed with brine (40 mL), dried (Na$_2$SO$_4$), filtered and concentrated in vacuo to afford a brown gum. This was purified by FCC, using 2-7% MeOH in DCM to afford the title compound. LCMS (Method 1): Rt 3.61 min, m/z 424, 426 [MH+].

d. 1-[3-tert-Butyl-1'-(2-hydroxyethyl)1'H[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea. (Intermediate Gd)

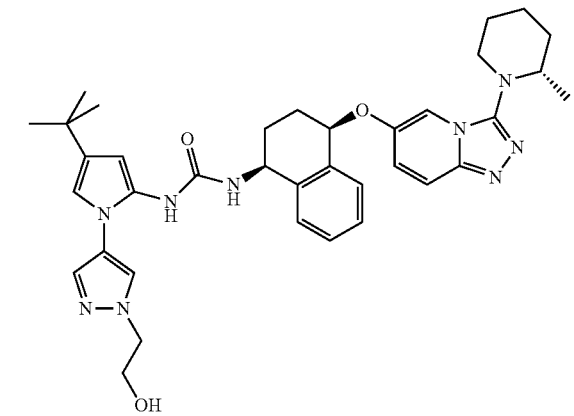 [SMILES: C[C@H]1CCCCN1c1nnc2ccc(O[C@@H]3CC[C@H](NC(=O)Nc4cc(C(C)(C)C)cn4-c4cnn(CCO)c4)c4ccccc43)cn12]

A mixture of Intermediate Gc (100 mg, 235 μmol), Intermediate 2 (89.0 mg, 235 μmol) and DIPEA (61.0 μL, 353 μmol) in dioxane (1.5 mL) was heated at 60° C. for 48 h. The mixture was cooled to RT, diluted with DCM (5 mL) and washed with water (5 mL) and brine (5 mL) The organic layer was passed through a phase separator and concentrated in vacuo. The residue was purified by FCC, using 0-10% [2M NH$_3$ in MeOH] in DCM, to afford the title compound (77 mg, 50%). LCMS (Method 1): Rt 3.32 min, m/z 653 [MH$^+$].

e. Methanesulfonic acid 2-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester. (Intermediate G)

A mixture of Intermediate Gd (75.0 mg, 115 μmol), methanesulfonyl chloride (11.6 μL, 149 μmol) and DIPEA (60.0

μL, 345 μmol) in DCM (1 mL) was stirred at RT for 30 min. The reaction mixture was partitioned between DCM (5 mL) and water (2×5 mL) The organic layer was washed with brine (5 mL), separated through a phase separating cartridge and concentrated in vacuo to afford the title compound (84 mg, 100%). LCMS (Method 1): Rt 3.54 min, m/z 731 [MH$^+$].

Intermediate H. Methanesulfonic acid 3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-benzyl ester

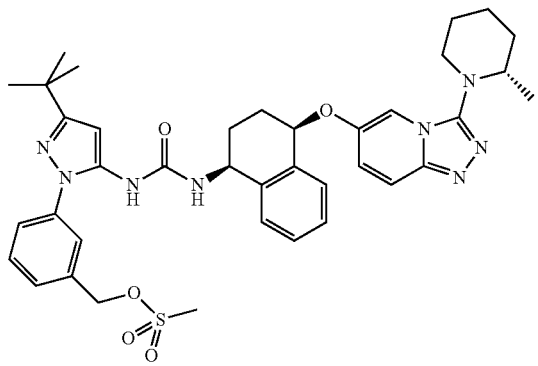 [SMILES: C[C@H]1CCCCN1c1nnc2ccc(O[C@@H]3CC[C@H](NC(=O)Nc4cc(C(C)(C)C)nn4-c4cccc(COS(C)(=O)=O)c4)c4ccccc43)cn12]

a. 5-tert-Butyl-2-(3-hydroxymethyl-phenyl)-2H-pyrazol-3-yl]-carbamic acid 2,2,2-trichloro-ethyl ester (Intermediate Ha)

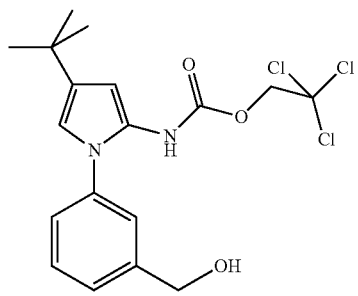 [SMILES: CC(C)(C)c1cc(NC(=O)OCC(Cl)(Cl)Cl)n(-c2cccc(CO)c2)c1]

To a bi-phasic mixture of [3-(5-Amino-3-tert-butyl-pyrazol-1-yl)-phenyl]methanol (US. 20080248548; 737 mg, 3.00 mmol) in EtOAc (22.5 mL) and 1N NaOH solution (8.11 mL, 8.11 mmol) at 0° C. was added 2,2,2-trichloroethyl chloroformate (0.45 mL, 3.30 mmol) and the mixture stirred for 1.25 h. The layers were separated and the organic layer was washed with brine, dried and concentrated in vacuo to give the title compound (1.26 g, 99%). LCMS (Method 1): Rt 4.00 min, m/z 420, 422 [MH$^+$].

b. 1-[5-tert-Butyl-2-(3-hydroxymethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate Hb)

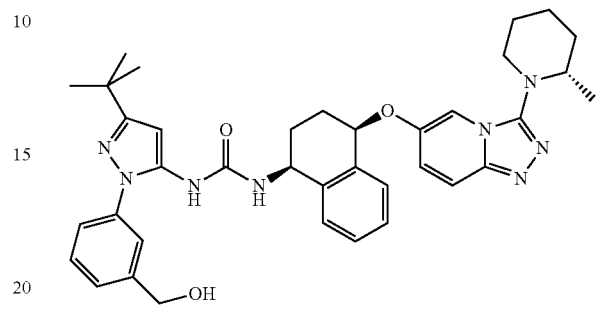

A mixture of Intermediate Ha (319 mg, 0.85 mmol), Intermediate 2 (335 mg, 0.85 mmol) and DIPEA (294 μL, 1.69 mmol) in dioxane (10 mL) was stirred at 80° C. for 18 h. After cooling, the reaction mixture was partitioned between water and DCM. The aqueous phase was extracted with EtOAc (×3) and the combined organic layers were washed with brine, dried (MgSO$_4$) and concentrated in vacuo. The resulting residue was purified by FCC on silica, using a gradient of 0-10% MeOH in DCM, to afford the title compound (362 mg, 66%). LCMS (Method 2): Rt 3.29 min, m/z 649 [MH$^+$].

c. Methanesulfonic acid 3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-benzyl ester (Intermediate H)

To an ice-bath cooled solution of Intermediate Hb (316 mg, 0.49 mmol) in DCM (5.0 mL) was added DIPEA (339 μL, 1.95 mmol) followed by methanesulfonyl chloride (76 μL, 0.97 mmol). The reaction mixture was stirred for 3 h and then quenched with water. The aqueous phase was extracted with DCM (×3) and the combined organic layers were washed with brine, dried (MgSO$_4$) and concentrated in vacuo to afford the title compound (Quantitative, assumed 0.49 mmol). The isolated product was used in the following step without further purification. LCMS (Method 2): Rt 3.61 min, m/z 727 [MH$^+$].

Examples 1-12

General Displacement Procedure

A mixture of Intermediate A-H (0.14 mmol) and an appropriate amine [see table 2](2.15 mmol) in anhydrous THF (3 mL) was stirred at 40° C. for 18 h in a sealed vial. The volatiles were concentrated in vacuo and the resultant residue was purified by HPLC (Gemini C18, 20-40% MeCN in H$_2$O, 0.1% HCO$_2$H, 18 ml/min.) and freeze dried to afford the title compound (30-50%).

| Ex. No. | Amine | Intermediate Used | Example Structure | NMR (400 MHz) δ | LCMS |
|---|---|---|---|---|---|
| 1 | Dimethylamine | A | 1-[1'-(2-Dimethylamino-ethyl)-3-isopropyl-1'H-[1,4']bipyrazolyl-5-yl]-3-{(1S,4R)-4-[3-((2S,6R)-2,6-dimethyl-piperidin-1-yl)-[1,2,4]triazolo[4,3a]pyridin-6-yloxy]-1,2,3,4-tetrahydro-naphthalen-1-yl}-urea formate salt | $^1$H NMR (400 MHz, d$_6$-DMSO): 0.61 (6H, dd, J = 6.3 Hz), 1.21 (6H, d), 1.37-1.58 (3H, m), 1.66-1.74 (2H, m), 1.76-1.83 (1H, m), 1.84-1.93 (1H, m), 1.93-2.02 (1H, m), 1.94-2.13 (1H, m), 2.16 (6H, s), 2.67 (2H, t, J = 6.3 Hz), 2.77-2.89 (1H, m), 3.09-3.22 (4H, m), 4.23 (2H, t, J = 6.3 Hz), 4.80-4.88 (1H, m), 5.54 (1H, t, J = 3.8 Hz), 6.22 (1H, s), 7.13-7.18 (1H, m), 7.18-7.23 (1H, dd, J = 9.7, 2.2 Hz), 7.23-7.30 (1H, m), 7.33-7.38 (3H, m), 7.63 (1H, s), 7.66 (1H, d, J = 9.6 Hz), 7.89 (1H, d), 8.05 (2H, s), 8.18 (1.4H, s). | (Method 5): Rt 3.62 min, m/z 680 [MH$^+$]. |
| 2 | 1-Methylpiperazine | A | 1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-{3-isopropyl-1'-[2-(4-methyl-piperazin-1-yl)-ethyl]-1'H-[1,4']bipyrazolyl-5-yl}-urea formate salt | $^1$H NMR (400 MHz, d$_6$-DMSO): 0.61 (6H, dd, J = 6.3 Hz), 1.21 (6H, d), 1.42-1.63 (3H, m), 1.70-1.78 (2H, m), 1.80-1.88 (1H, m), 1.87-1.98 (1H, m), 1.97-2.07 (1H, m), 2.15 (3H, s), 2.15-209 (2H, m), 2.32 (3H, bs), 2.46 (3H, bs), 2.76 (2H, t, J = 6.3 Hz), 2.83-2.94 (1H, m), 3.15-3.29 (4H, m), 4.26 (2H, t, J = 6.3 Hz), 4.85-4.93 (1H, m), 5.58 (1H, t, J = 3.8 Hz), 6.26 (1H, s), 7.13-7.18 (1H, m), 7.18-7.23 (1H, dd, J = 9.7, 2.2 Hz), 7.27-7.35 (1H, m), 7.37-7.42 (3H, m), 7.67 (1H, s), 7.70 (1H, d, J = 9.6 Hz), 7.93 (1H, d), 8.09 (1H, s), 8.11 (1H, s), 8.3 (0.55H, s). | (Method 5): Rt 3.61 min; m/z 735 [MH$^+$]. |

| Ex. No. | Amine | Intermediate Used | Example Structure | NMR (400 MHz) δ | LCMS |
|---|---|---|---|---|---|
| 3 |  Pyrrolidine | A | 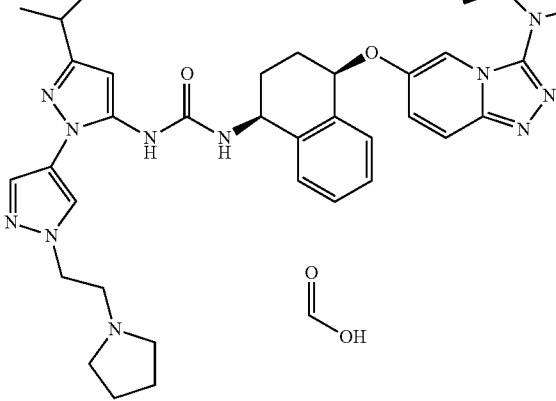 1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-[3-isopropyl-1'-(2-pyrrolidin-1-yl-ethyl)-1'H-[1,4']bipyrazolyl-5-yl]-urea formate salt | $^1$H NMR (400 MHz, d$_6$-DMSO): 0.63 (6H, dd, J = 6.3 Hz), 1.20 (6H, d), 1.39-1.58 (3H, m), 1.62-1.68 (4H, m), 1.68-1.75 (2H, m), 1.76-1.84 (1H, m), 1.84-1.93 (1H, m), 1.94-2.03 (1H, m), 2.05-2.13 (2H, m), 2.46 (3H, br t), 2.79-2.88 (3H, m), 3.11-3.23 (3H, m), 4.23 (2H, t, J = 6.3 Hz), 4.82-4.90 (1H, m), 5.55 (1H, t, J = 3.8 Hz), 6.22 (1H, s), 7.15-7.20 (1H, m), 7.20-7.24 (1H, dd, J = 9.7, 2.2 Hz), 7.24-7.30 (1H, m), 7.33-7.39 (3H, m), 7.64 (1H, s), 7.67 (1H, d, J = 9.6 Hz), 7.89 (1H, d), 8.06 (2H, d), 8.27 (0.37H, s). | (Method 5): Rt 3.68 min, m/z 706 [MH$^+$]. |
| 4 | 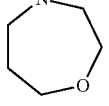 [1,4]Oxazepane | A | 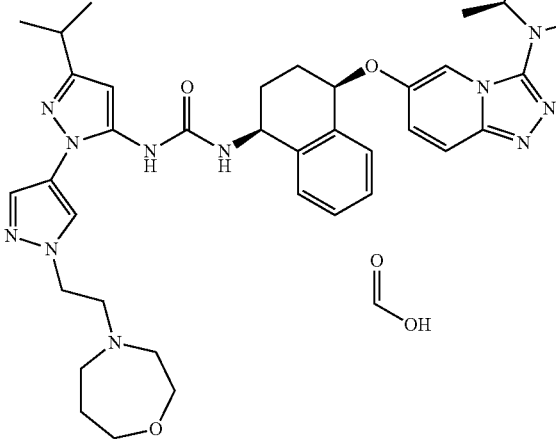 1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-[3-isopropyl-1'-(2-[1,4]oxazepan-4-yl-ethyl)-1'H-[1,4']bipyrazolyl-5-yl]-urea formate salt | $^1$H NMR (400 MHz, d$_6$-DMSO): 0.61 (6H, dd, J = 6.3 Hz), 1.20 (6H, d), 1.37-1.62 (3H, m), 1.66-1.84 (5H, m), 1.84-1.93 (1H, m), 1.94-2.02 (1H, m), 2.05-2.13 (2H, m), 2.65-2.71 (4H, m), 2.78-2.88 (1H, m), 2.89-2.95 (2H, t, J = 6.7 Hz), 3.12-3.21 (2H, m), 3.54-3.58 (2H, dd), 3.60-3.65 (2H, t, J = 5.6 Hz), 4.17-4.23 (2H, t, J = 7.1 Hz), 4.79-4.90 (1H, m), 5.54 (1H, t, J = 3.8 Hz), 6.22 (1H, s), 7.16-7.19 (1H, m), 7.20-7.24 (1H, dd, J = 9.7, 2.2 Hz), 7.24-7.30 (1H, m), 7.32-7.39 (3H, m), 7.64 (1H, s), 7.67 (1H, d, J = 9.6 Hz), 7.89 (1H, d), 8.06 (2H, s), 8.40 (0.21H, s). | (Method 5): Rt 365 min, m/z 736 [MH$^+$]. |

| Ex. No. | Amine | Intermediate Used | Example Structure | NMR (400 MHz) δ | LCMS |
|---|---|---|---|---|---|
| 5 | Dimethylamine | F | 1-[1'-(2-Dimethylamino-ethyl)-3-isopropyl-1'H-[1,3']bipyrazolyl-5-yl]-3-{(1S,4R)-4-[3-((2S,6R)-2,6-dimethyl-piperidin-1-yl)-[1,2,4]triazolo[4,3a]pyridin-6-yloxy]-1,2,3,4-tetrahydro-naphthalen-1-yl}-urea formate salt | $^1$H NMR (400 MHz, d$_6$-DMSO): 0.62 (6H, dd, J = 11.1, 6.3 Hz), 1.21 (6H, dd, J = 6.9, 0.8 Hz), 1.38-1.62 (3H, m), 1.67-1.75 (2H, m), 1.77-1.85 (1H, m), 1.89-2.02 (2H, m), 2.03-2.13 (1H, m), 2.19 (6H, s), 2.66 (2H, t, J = 6.3 Hz), 2.79-2.91 (1H, m), 3.12-3.23 (3H, m), 4.23 (2H, t, J = 6.3 Hz), 4.90-4.99 (1H, m), 5.55 (1H, t, J = 3.8 Hz), 6.32 (1H, d), 6.37 (1H, s), 7.21 (1H, dd, J = 9.7, 2.2 Hz), 7.24-7.30 (1H, m), 7.33-7.40 (3H, m), 7.66 (1H, d, J = 9.87 Hz), 7.82 (1H, d, J = 2.54 Hz), 7.88-7.92 (2H, m), 8.26 (0.4H, s), 9.3 (1H, s) | (Method 5): Rt 3.72 min, m/z 680.4 [MH$^+$]. |
| 6 | Dimethylamine | B | 1-[1'-(2-Dimethylamino-ethyl)-3-isopropyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | | (Method 3): Rt 2.71 min, m/z 666 [MH$^+$]. |

| Ex. No. | Amine | Intermediate Used | Example Structure | NMR (400 MHz) δ | LCMS |
|---|---|---|---|---|---|
| 7 | Dimethylamine | D | 1-[1'-(2-Dimethylamino-ethyl)-3-ethyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | | (Method 3): Rt 2.63 min, m/z 652 [MH+]. |
| 8 | Dimethylamine | C | 1-[1'-(2-Dimethylamino-ethyl)-3-ethyl-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | | (Method 3): Rt 2.73 min, m/z 666 [MH+]. |

| Ex. No. | Amine | Intermediate Used | Example Structure | NMR (400 MHz) δ | LCMS |
|---|---|---|---|---|---|
| 9 | <br>Dimethylamine | E | 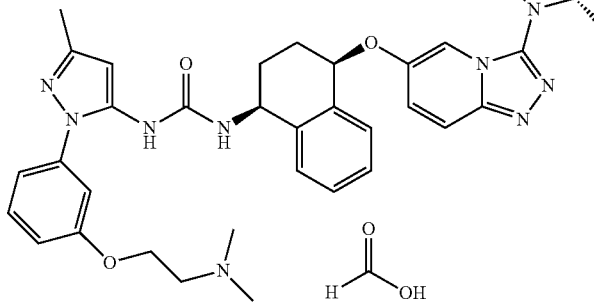<br>1-{2-[3-(2-Dimethylamino-ethoxy)-phenyl]-5-methyl-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^{1}$H NMR (400 MHz, $d_6$-DMSO): 0.91 (3H, d), 1.44-1.54 (2H, m), 1.60-1.69 (2H, m), 1.74-1.95 (4H, m), 1.98-2.14 (3H, m), 2.17 (3H, s), 2.61 (2H, t, J = 6.3 Hz), 2.85-2.94 (1H, m), 3.12-3.21 (3H, m), 4.07 (2H, t, J = 5.1 Hz), 4.78-4.86 (1H, m), 5.63 (1H, t, J = 4.6 Hz), 6.23 (1H, s), 6.96 (1H, dd, J = 8.6, 2.6 Hz), 7.03-7.11 (3H, m), 7.18 (1H, dd, J = 9.74, 2.1 Hz), 7.24-7.43 (5H, m), 7.64 (1H, d, J = 9.78 Hz), 7.69 (1H, d), 8.14 (1H, bs), 8.18 (1H, s). | (Method 5): Rt 3.18 min, m/z 664 [MH$^+$]. |
| 10 | <br>Azetidine | G | 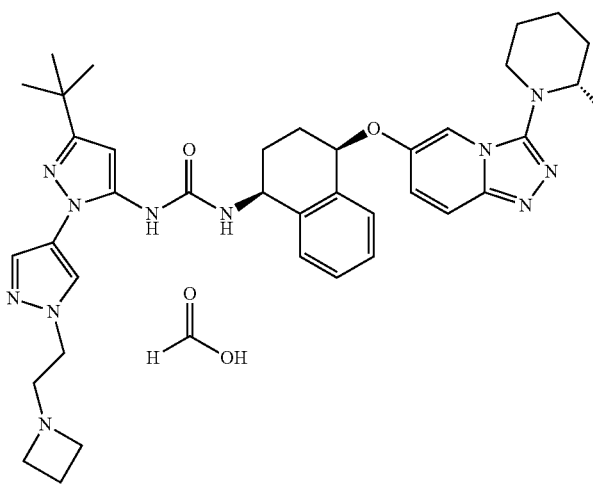<br>1-[1'-(2-Azetidin-1-yl-ethyl)-3-tert-butyl-1'H-[1,4']bipyrazolyl-5-yl]-3-{(1S,4R)-4-[3-((S)-2-methyl-piperidin-1-yl)-[1,2,4]triazolo[4,3a]pyridin-6-yloxy]-1,2,3,4-tetrahydro-naphthalen-1-yl}-urea formate salt | $^{1}$H NMR (400 MHz, $d_6$-DMSO): 0.91 (3H, d, J = 6.4 Hz), 1.25 (9H, s), 1.45-1.57 (2H, m), 1.61-1.72 (2H, m), 1.74-2.01 (6H, m), 2.01-2.18 (2H, m), 2.77 (2H, t, J = 6.2 Hz), 2.89-2.95 (1H, m), 3.11 (4H, t, J = 7.0 Hz), 3.13-3.20 (m, obscured by water), 3.27-3.36 (m, obscured by water), 4.04 (2H, t, J = 6.2 Hz), 4.80-4.88 (1H, m), 5.53 (1H, t, J = 4.4 Hz), 6.26 (1H, s), 7.15-7.22 (2H, m), 7.25-7.31 (1H, m), 7.31-7.40 (3H, m), 7.61-7.66 (2H, m), 7.70 (1H, d, J = 1.8 Hz), 8.02 (2H, s), 8.19 (1.5H, s). | (Method 3): Rt 3.55 min, m/z 692.5 [MH$^+$]. |

-continued

| Ex. No. | Amine | Intermediate Used | Example Structure | NMR (400 MHz) δ | LCMS |
|---|---|---|---|---|---|
| 11 | Azetidin-3-yl-dimethyl-amine | G | 1-{3-tert-Butyl-1'-[2-(3-dimethylamino-azetidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | ¹H NMR (400 MHz, d6-DMSO): 0.91 (3H, d, J = 6.1 Hz), 1.25 (9H, s), 1.44-1.57 (2H, m), 1.61-1.73 (2H, m), 1.74-1.93 (4H, m), 1.96 (6H, s), 2.02-2.18 (2H, m), 2.69-2.77 (3H, m), 2.80 (2H, t, J = 6.2 Hz), 2.86-2.95 (1H, m), 3.12-3.20 (m, obscured by water and solvent), 3.27-3.39 m, obscured by water), 4.06 (2H, t, J = 6.2 Hz), 4.80-4.88 (1H, m), 5.53 (1H, t, J = 4.5 Hz), 6.27 (1H, s), 7.15-7.23 (2H, m), 7.25-7.31 (1H, m), 7.33-7.41 (3H, m), 7.61-7.66 (2H, m), 7.69-7.71 (1H, m), 8.00-8.04 (2H, m), 8.18 (1H, s). | (Method 3): Rt: 3.36 min, m/z 735.5 [MH⁺]. |
| 12 | Azetidin-3-yl-dimethyl-amine | H | 1-{5-tert-Butyl-2-[3-(3-dimethylamino-azetidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | ¹H NMR (400 MHz, d6-DMSO): 0.86 (3H, d, J = 6.2 Hz), 1.23 (9H, s), 1.42-1.50 (2H, m), 1.58-1.67 (2H, m), 1.72-1.84 (3H, m), 1.84-1.91 (3H, m), 1.91 (6H, s), 1.95-2.10 (2H, m), 2.66-2.77 (3H, m), 2.86 (1H, ddd, J = 12.7, 9.0, 3.9 Hz), 3.08-3.16 (1H, dt, J = 12.3, 4.3 Hz), (m, obscured by solvent peak), 3.56 (2H, s), 4.77 (1H, td, J = 8.4, 5.7 Hz), 5.47 (1H, t, J = 4.2 Hz), 6.28 (1H, s), 7.02 (1H, d, J = 8.6 Hz), 7.14 (1H, dd, J = 9.8, 2.1 Hz), 7.20-7.25 (3H, m), 7.25-7.34 (4H, m), 7.38 (1H, t, J = 7.7 Hz), 7.59 (1H, d, J = 10.0 Hz), 7.64 (1H, d, J = 1.8 Hz), 8.06 (1H, s), 8.25 (0.5H, s). | (Method 3): Rt: 3.34 min, m/z 731 [MH⁺]. |

Example 13

1-(5-tert-Butyl-2-methyl-2H-pyrazol-3-yl)-3-((1S,4R)-4-{3-[2,6-dichloro-4-(4-methyl-piperazin-1-ylmethyl)-phenyl]-[1,2,4]triazolo[4,3-a]pyridin-6-yloxy}-1,2,3,4-tetrahydro-naphthalen-1-yl)-urea formate salt

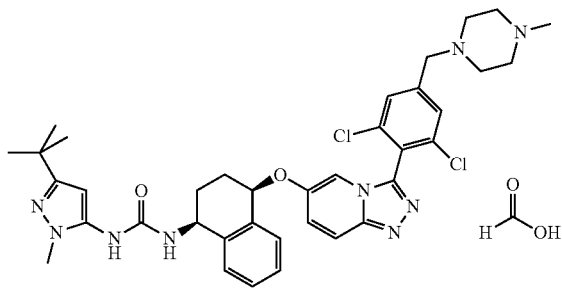 [SMILES: CN1CCN(Cc2cc(Cl)c(-c3nnc4ccc(O[C@@H]5CC[C@H](NC(=O)Nc6cc(C(C)(C)C)nn6C)c6ccccc65)cn34)c(Cl)c2)CC1 ; O=CO]

a. {3,5-Dichloro-4-[(5-fluoro-pyridin-2-yl)-hydrazonomethyl]-phenyl}-methanol (Intermediate 13a)

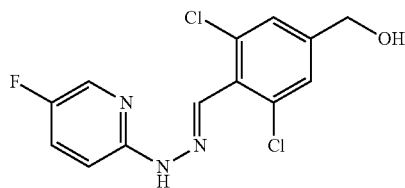 [SMILES: OCc1cc(Cl)c(/C=N/Nc2ccc(F)cn2)c(Cl)c1]

A solution of 2,6-dichloro-4-hydroxymethylbenzaldehyde (0.50 g, 2.40 mmol) in propionitrile (4.8 mL) was treated with (5-fluoro-pyridin-2-yl)-hydrazine (0.41 g, 2.40 mmol) and the solution was heated to 85° C. for 2 h then cooled to 0° C. The solid was filtered off, washed with ice-cold propionitrile and dried at 50° C. in vacuo to give the title compound (0.73 g, 95%). LCMS (Method 3): Rt 3.55 min, m/z 314, 316 [MH$^+$].

b. [3,5-Dichloro-4-(6-fluoro[1,2,4]triazolo[4,3-a]pyridin-3-yl)-phenyl]-methanol (Intermediate 13b)

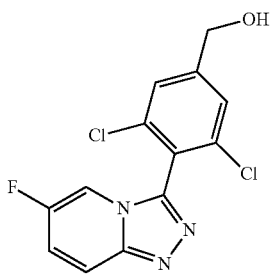 [SMILES: OCc1cc(Cl)c(-c2nnc3ccc(F)cn23)c(Cl)c1]

A suspension of Intermediate 13a (0.73 g, 2.30 mmol) in DCM (7.3 mL) was treated with diacetoxyiodobenzene (0.79 g, 2.40 mmol) and the solution was cooled to 0° C. MeOH (0.8 mL) was added dropwise and the mixture was stirred at ambient temperature for 4.5 h. The mixture was cooled to 0° C. and treated slowly with aqueous 1N NaOH solution (~5 mL). The layers were separated and the aqueous layer was then extracted with DCM (2×). The combined organic layers were washed with water and brine, dried (Na$_2$SO$_4$), filtered and evaporated in vacuo. The aqueous layers were combined and extracted with 20% MeOH in DCM. The organic layer was dried (Na$_2$SO$_4$), filtered and evaporated in vacuo. The residues were dissolved in MeOH/DCM, combined, preadsorbed onto diatomaceous earth and purified by FCC, using 0-8% MeOH in DCM, to give the title compound (0.57 g, 78%). LCMS (Method 3): Rt 2.72 min, m/z 312, 314 [MH$^+$].

c. 3,5-Dichloro-4-(6-fluoro-[1,2,4]triazolo[4,3-a]pyridin-3-yl)-benzaldehyde (Intermediate 13c)

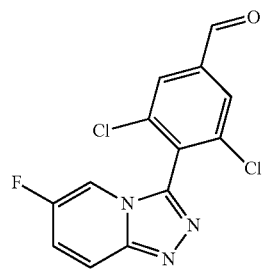 [SMILES: O=Cc1cc(Cl)c(-c2nnc3ccc(F)cn23)c(Cl)c1]

A suspension of Intermediate 13b (0.57 g, 1.80 mmol) in DCM (18 mL) at 0° C. was treated with Dess Martin periodinane (0.85 g, 2.00 mmol) and the solution was stirred at 0° C. for 1 h. The mixture was diluted with a saturated aqueous sodium bicarbonate solution and the layers were separated. The aqueous layer was then extracted with DCM (2×). The combined organic layers were washed with a saturated aqueous sodium bicarbonate solution and brine, dried (Na$_2$SO$_4$), filtered and evaporated in vacuo. The residue was dissolved in DCM containing a few drops of MeOH and purified by FCC, using 0-5% MeOH in DCM, to give the title compound (0.66 g, quant). LCMS (Method 3): Rt 3.03 min, m/z 328, 330 [MH$^+$].

d. 3-[2,6-Dichloro-4-(4-methyl-piperazin-1-ylmethyl)-phenyl]-6-fluoro-[1,2,4]triazolo[4,3-a]pyridine (Intermediate 13d)

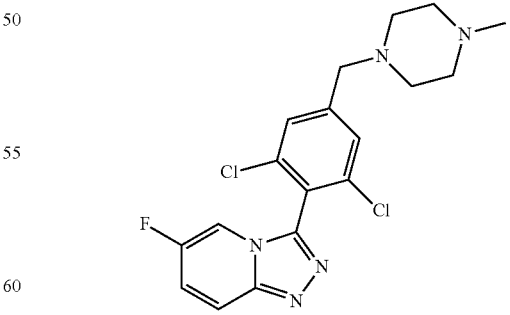

A cloudy solution of Intermediate 13c (0.66 g, 1.80 mmol) in DCE (18 mL) was treated with 1-methylpiperazine (0.22 mL, 2.00 mmol) then sodium triacetoxyborohydride (0.58 g, 2.70 mmol), and the solution was stirred at ambient temperature overnight. The mixture was treated with another portion of 1-methylpiperazine (0.22 mL, 2.00 mmol) and sodium triacetoxyborohydride (0.58 g, 2.70 mmol), and stirred for 5 h. The mixture was cautiously diluted with a saturated aqueous sodium bicarbonate solution and the layers were separated. The aqueous layer was then extracted with DCM (2×). The combined organic layers were washed with a saturated aqueous sodium bicarbonate solution and brine, dried (Na$_2$SO$_4$), filtered and evaporated in vacuo. The residue was dissolved in DCM and purified by FCC, using 0-8% [2M NH$_3$ in MeOH] in DCM, to give the title compound (0.41 g, 57%). LCMS (Method 3): Rt 2.11 min, m/z 394, 396 [MH$^+$].

e. (1S,4R)-4-{3-[2,6-Dichloro-4-(4-methyl-piperazin-1-ylmethyl)-phenyl]-[1,2,4]triazolo[4,3-a]pyridin-6-yloxy}-1,2,3,4-tetrahydro-naphthalen-1-ylamine (Intermediate 13e)

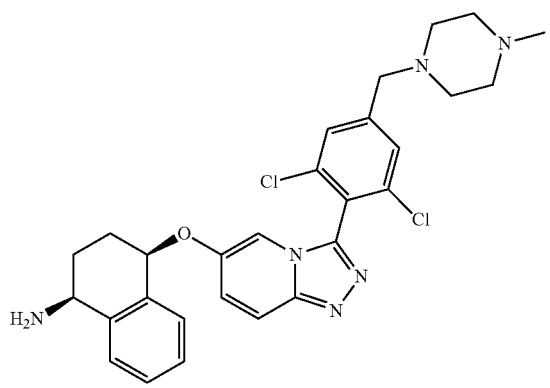 [SMILES: CN1CCN(Cc2cc(Cl)c(-c3nnc4ccc(O[C@@H]5CC[C@H](N)c6ccccc65)cn34)c(Cl)c2)CC1]

A suspension of sodium hydride (60% dispersion in oil, 56 mg, 1.39 mmol) in dry DMF (2.0 mL) under nitrogen was treated with Intermediate 1 (46 mg, 0.28 mmol) and the mixture was stirred for 20 min. Intermediate 13d (110 mg, 0.28 mmol) was added and the mixture was heated to 60° C. for 1.75 h then quenched with MeOH. The mixture was further diluted with MeOH and applied to a pre-conditioned (MeOH) SCX-2 cartridge (10g). The cartridge was eluted with MeOH then 2M NH$_3$ in MeOH. The relevant fractions were combined and concentrated in vacuo. The residue was dissolved in DCM containing a few drops of MeOH and purified by FCC, using 0-10% [2M NH$_3$ in MeOH] in DCM, to give the title compound (28 mg, 19%). LCMS (Method 3): Rt 2.08 min, m/z 537, 539 [MH$^+$].

f. 1-(5-tert-Butyl-2-methyl-2H-pyrazol-3-yl)-3-((1S, 4R)-4-{3-[2,6-dichloro-4-(4-methyl-piperazin-1-ylmethyl)-phenyl]-[1,2,4]triazolo[4,3-a]pyridin-6-yloxy}-1,2,3,4-tetrahydro-naphthalen-1-yl)-urea formate salt (Example 13)

(5-tert-Butyl-2-methyl-2H-pyrazol-3-yl)-carbamic acid 2,2,2-trichloro-ethyl ester (US 2004/0192653, which is incorporated herein by reference in its entirety; 17 mg, 0.051 mmol) was treated with a solution of Intermediate 13e (25 mg, 0.047 mmol) in 1,4-dioxane (0.4 mL) then DIPEA (10 μL, 0.058 mmol) was added. The mixture was stirred at 70° C. overnight. The mixture was treated with another portion of (5-tert-butyl-2-methyl-2H-pyrazol-3-yl)-carbamic acid 2,2,2-trichloro-ethyl ester (7.8 mg, 0.024 mmol) in 1,4-dioxane (0.1 mL) and stirred at 70° C. for 6 h. The mixture was evaporated in vacuo and the residue was partitioned between DCM and water. The aqueous layer was then extracted with DCM (2×). The combined organic layers were washed with brine, dried (Na2SO4), filtered and evaporated in vacuo. The residue was purified by HPLC in 4 portions (Method 6, 5-95% MeCN in H$_2$O, 0.1% HCO$_2$H over 30 min), and the isolated product triturated (diethyl ether) to give a solid. The solid was collected by filtration, washed with ether and dried at 50° C. in vacuo to give the title compound. (5.4 mg, 16%). LCMS (Method 5): Rt 3.27 min, m/z 716.3 [MH$^+$]. $^1$H NMR (400 MHz, d$_6$-DMSO): 1.20 (9H, s), 1.82-1.99 (2H, m), 1.99-2.05 (1H, m), 2.05-2.14 (1H, m), 2.18 (3H, s), 2.29-2.42 (4H, br s), 2.42-2.52 (4H, br s, partially obscured by DMSO), 3.56 (3H, s, partially obscured by water), 3.60 (2H, s, partially obscured by water), 4.79-4.88 (1H, m), 5.54 (1H, t, J=4.3 Hz), 6.01 (1H, s), 6.91 (1H, d, J=8.4 Hz), 7.23-7.30 (1H, m), 7.33-7.39 (4H, m), 7.66 (2H, s), 7.91 (1H, d, J=10.2 Hz), 7.97 (1H, d, J=1.7 Hz), 8.21 (1H, s), 8.29 (1H, s).

Example 14

1-(5-tert-Butyl-2-methyl-2H-pyrazol-3-yl)-3-{(1S, 4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt

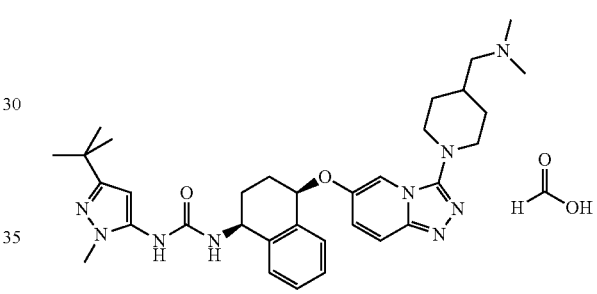

a. 6-Fluoro-[1,2,4]triazolo[4,3-a]pyridine (Intermediate 14a)

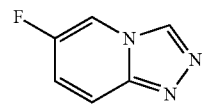

(5-Fluoro-pyridin-2-yl)-hydrazine (500 mg, 3.93 mmol) in diethoxymethyl acetate (5 mL) was stirred at RT for 2 h. The resulting precipitate was diluted with cyclohexane (5 mL) and filtered to give the title compound (379 mg, 70%). $^1$H NMR (400 MHz, CDCl$_3$): 7.25 (1H, m), 7.84 (1H, m), 8.09 (1H, t), 8.84 (1H, s).

b. 3-Chloro-6-fluoro-[1,2,4]triazolo[4,3-a]pyridine (Intermediate 14b)

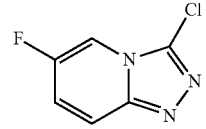 [SMILES: Fc1ccc2nnc(Cl)n2c1]

A solution of Intermediate 14a (789 mg, 5.98 mmol) and N-chlorosuccinimide (878 mg, 6.57 mmol) in chloroform (15 mL) was heated at 65° C. overnight. The cooled mixture was washed with sat. aq. NaHCO$_3$ solution (2×15 mL) and dried (Na$_2$SO$_4$). The solvent was evaporated, then the residue suspended in diethyl ether (10 mL) and filtered to give the title compound (730 mg, 76%). LCMS (Method 1): Rt 1.83 min, m/z 172 [MH$^+$].

c. [1-(6-Fluoro-[1,2,4]triazolo[4,3-a]pyridin-3-yl)-piperidin-4-yl]-methanol (Intermediate 14c)

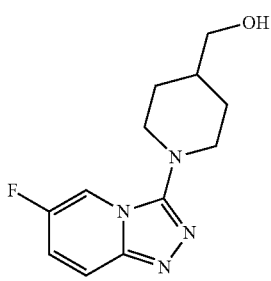 [SMILES: OCC1CCN(c2nnc3ccc(F)cn23)CC1]

A solution of Intermediate 14b (593 mg, 3.45 mmol) and 4-piperidinemethanol (1.59 g, 13.8 mmol) in NMP (10 mL) was heated in the microwave at 170° C. for 3 h. The cooled mixture was applied to an SCX-2 cartridge (70 g), washing with methanol then eluting basic components with 0.4-2 M NH$_3$ in MeOH. Product containing fractions were combined and concentrated in vacuo. The residue was purified by FCC, using 0-15% MeOH in EtOAc, to give the title compound as a brown gum (481 mg, 56%). LCMS (Method 3): Rt 2.12 min, m/z 251 [MH$^+$].

d. 6-Fluoro-3-(4-triisopropylsilanyloxymethyl-piperidin-1-yl)-[1,2,4]triazolo[4,3-a]pyridin (Intermediate 14d)

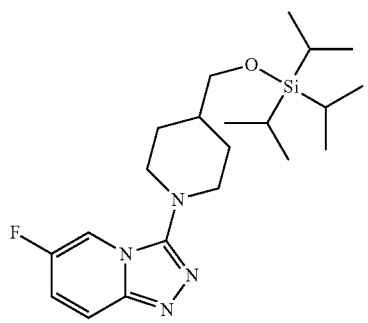 [SMILES: CC(C)[Si](OCC1CCN(c2nnc3ccc(F)cn23)CC1)(C(C)C)C(C)C]

To a solution of Intermediate 14c (470 mg, 1.88 mmol) and Et$_3$N (390 μL, 2.82 mmol) in DCM (5 mL) was added triisopropylsilyltrifluoromethane sulfonate (607 μL, 2.26 mmol) and the mixture stirred at RT for 0.5 h. The mixture was washed with sat. aq. NaHCO$_3$ solution, dried and concentrated in vacuo. The residue was purified by FCC, using 0-100% EtOAc in cyclohexane, then 10% MeOH in EtOAc, to give the title compound (565 mg, 74%). LCMS (Method 3): Rt 5.21 min, m/z 407 [MH$^+$].

e. (1S,4R)-4-[3-(4-Triisopropylsilanyloxymethyl-piperidin-1-yl)-[1,2,4]triazolo[4,3-a]pyridin-6-yloxy]-1,2,3,4-tetrahydro-naphthalen-1-ylamine (Intermediate 14e)

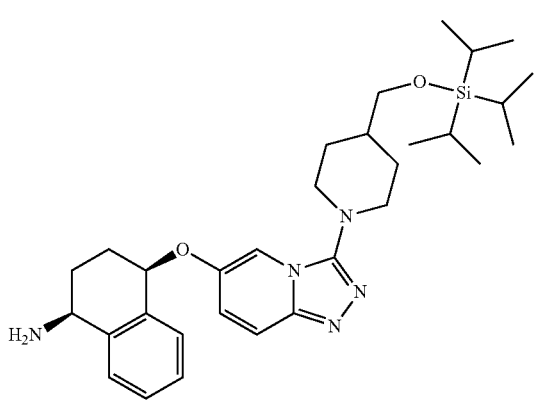 [SMILES: CC(C)[Si](OCC1CCN(c2nnc3ccc(O[C@@H]4CC[C@H](N)c5ccccc54)cn23)CC1)(C(C)C)C(C)C]

To a solution of Intermediate 1 (223 mg, 1.37 mmol) in DMF (3 mL) was added NaH (60% dispersion in oil, 168 mg, 4.20 mmol) and the mixture stirred at RT for 15 min. A solution of Intermediate 14d (555 mg, 1.37 mmol) in DMF (3 mL) was added and the mixture stirred at 60° C. for 1.75 h. The cooled mixture was diluted with water and extracted with DCM (5×20 mL). The combined organics were dried and concentrated in vacuo. The residue was purified by FCC, using 0-14% [2M NH$_3$ in MeOH] in DCM, to give the title compound as a brown gum (344 mg, 46%). LCMS (Method 3): Rt 3.29 min, m/z 550 [MH$^+$].

f. 1-(5-tert-Butyl-2-methyl-2H-pyrazol-3-yl)-3-{(1S,4R)-4-[3-(4-triisopropylsilanyloxymethyl-piperidin-1-yl)-[1,2,4]triazolo[4,3-a]pyridin-6-yloxy]-1,2,3,4-tetrahydro-naphthalen-1-yl}-urea (Intermediate 14f)

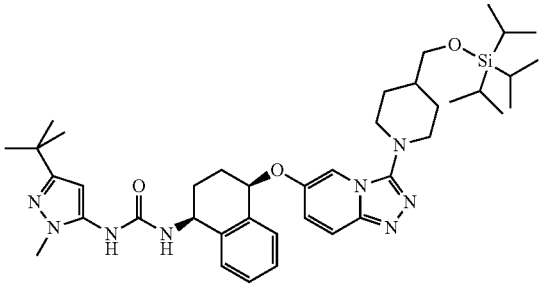 [SMILES: CC(C)[Si](OCC1CCN(c2nnc3ccc(O[C@@H]4CC[C@H](NC(=O)Nc5cc(C(C)(C)C)nn5C)c5ccccc54)cn23)CC1)(C(C)C)C(C)C]

A solution of (5-tert-butyl-2-methyl-2H-pyrazol-3-yl)-carbamic acid 2,2,2-trichloro-ethyl ester (US 20040192653, 90 mg, 0.273 mmol), Intermediate 14e (150 mg, 0.273 mmol) and DIPEA (71 μL, 0.409 mmol) in dioxane (2 mL) was heated at 60° C. for 48 h. The reaction mixture was cooled and diluted with DCM (5 mL). The organic layer was washed with water (3×5 mL), passed through a phase separator and concentrated in vacuo. The residue was purified by FCC, using 0-10% [2M NH3 in MeOH] in DCM, to afford the title compound (117 mg, 59%). LCMS (Method 3): Rt: 5.12 min, m/z 729 [MH$^+$].

g. 1-(5-tert-Butyl-2-methyl-2H-pyrazol-3-yl)-3-{(1S, 4R)-4-[3-(4-hydroxymethyl-piperidin-1-yl)-[1,2,4] triazolo[4,3-a]pyridin-6-yloxy]-1,2,3,4-tetrahydro-naphthalen-1-yl}-urea (Intermediate 14g)

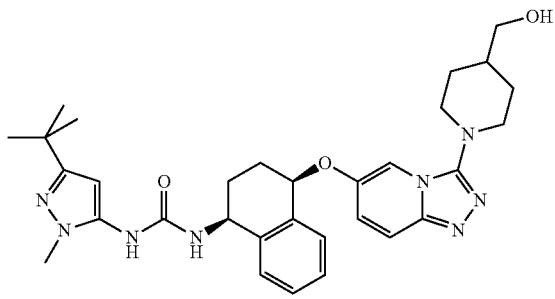 [SMILES: Cn1nc(C(C)(C)C)cc1NC(=O)N[C@H]1CC[C@@H](Oc2ccc3nnc(N4CCC(CO)CC4)n3c2)c2ccccc21]

Tetrabutylammonium fluoride (1M solution in THF, 211 μL, 0.211 mmol) was added to a solution of Intermediate 14f (110 mg, 0.151 mmol) in THF (3 mL) and the reaction mixture was stirred at RT for 1 h. The mixture was diluted with DCM (5 mL) and washed with water (2×5 mL) and brine (5 mL). The organic layer was passed through a phase separator and concentrated in vacuo. The residue was purified by FCC, using 0-10% [2M NH3 in MeOH] in DCM, to afford the title compound (52 mg, 60%). LCMS (Method 3): Rt: 2.91 min, m/z 573 [MH+].

h. Methanesulfonic acid 1-(6-{(1R,4S)-4-[3-(5-tert-butyl-2-methyl-2H-pyrazol-3-yl)-ureido]-1,2,3,4-tetrahydro-naphthalen-1-yloxy}-[1,2,4]triazolo[4,3-a]pyridin-3-yl)-piperidin-4-ylmethyl ester (Intermediate 14h)

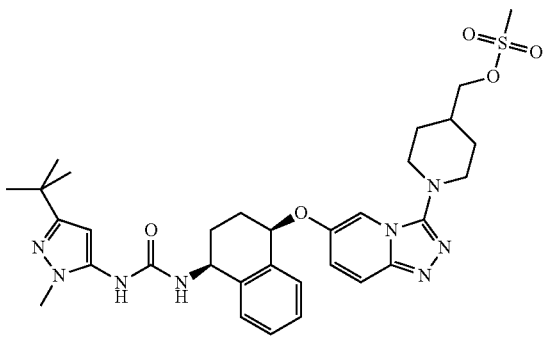 [SMILES: Cn1nc(C(C)(C)C)cc1NC(=O)N[C@H]1CC[C@@H](Oc2ccc3nnc(N4CCC(COS(C)(=O)=O)CC4)n3c2)c2ccccc21]

Methanesulfonyl chloride (8.8 μL, 0.13 mmol) was added to a solution of Intermediate 14g (50 mg, 0.08 mmol) and DIPEA (46 μL, 0.26 mmol) in DCM (1.5 mL) and the reaction mixture was stirred at RT for 1 h. The mixture was diluted with DCM (5 mL) and washed with water (3×5 mL). The organic layer was passed through a phase separator and concentrated in vacuo to afford the title compound (57 mg, 100%). LCMS (Method 3): Rt: 3.21 min, m/z 651 [MH+].

i. 1-(5-tert-Butyl-2-methyl-2H-pyrazol-3-yl)-3-{(1S, 4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt (Example 14)

A solution of Intermediate 14h (57 mg, 0.08 mmol) and dimethylamine (2M in THF, 0.873 mL, 1.75 mmol) in THF (4 mL) was heated at 60° C. for 18 h. A further 1.4 mL of dimethylamine (2M in THF) was added and the reaction mixture was heated at 65° C. for 48 h. The reaction mixture was cooled to RT and the solvent was removed by air, to leave a residue which was purified by MDAP (Method 7), to afford the title compound (18 mg, 35%). LCMS (Method 5): Rt: 3.00 min, m/z 600.4 [MH+]. $^1$H NMR (400 MHz, d$_6$-DMSO): 1.20 (9H, s), 1.32-1.47 (2H, m), 1.64-1.76 (1H, m), 1.76-1.86 (2H, m), 1.87-2.12 (4H, m), 2.13-2.21 (9H, m), 2.86-2.99 (2H, m, obscured by water), 3.35-3.48 (2H, m, obscured by water), 3.57 (2H, s, obscured by water), 4.82-4.91 (1H, m), 5.57 (1H, t, J=4.5 Hz), 6.02 (1H, s), 6.91 (1H, d, J=8.8 Hz), 7.18 (1H, dd, J=9.8, 1.9 Hz), 7.26-7.33 (1H, m), 7.34-7.43 (3H, m), 7.62 (1H, d, J=10.0 Hz), 7.65 (1H, d, J=1.8 Hz), 8.19 (1H, s), 8.27 (1H, s).

Example 15

1-(5-tert-Butyl-isoxazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea a. 1-(5-tert-Butyl-isoxazol-3-yl)-3-{(1S,4R)-4-[3-(4-triisopropylsilanyloxymethyl-piperidin-1-yl)-[1,2,4] triazolo[4,3-a]pyridin-6-yloxy]-1,2,3,4-tetrahydro-naphthalen-1-yl}-urea (Intermediate 15a)

Intermediate 14e was reacted with (5-tert-butyl-isoxazol-3-yl)-carbamic acid 2,2,2-trichloro-ethyl ester (WO 2006/091671, which is incorporated herein by reference in its entirety) in an analogous manner to that described in Example 14 step f to give the title compound. LCMS (Method 3): Rt: 5.43 min, m/z 717 [MH⁺].

b. 1-(5-tert-Butyl-isoxazol-3-yl)-3-{(1S,4R)-4-[3-(4-hydroxymethyl-piperidin-1-yl)-[1,2,4]triazolo[4,3-a]pyridin-6-yloxy]-1,2,3,4-tetrahydro-naphthalen-1-yl}-urea (Intermediate 15b)

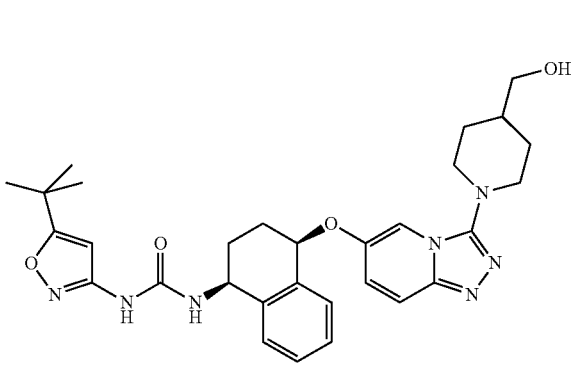 [SMILES: CC(C)(C)c1cc(NC(=O)N[C@H]2CC[C@@H](Oc3ccc4nnc(N5CCC(CO)CC5)n4c3)c3ccccc32)no1]

Intermediate 15a was reacted in an analogous manner to that described in Example 14 step g to give the title compound. LCMS (Method 3): Rt: 3.18 min, m/z 560 [MH⁺].

c. Methanesulfonic acid 1-(6-{(1R,4S)-4-[3-(5-tert-butyl-isoxazol-3-yl)-ureido]-1,2,3,4-tetrahydro-naphthalen-1-yloxy}-[1,2,4]triazolo[4,3-a]pyridin-3-yl)-piperidin-4-ylmethyl ester (Intermediate 15c)

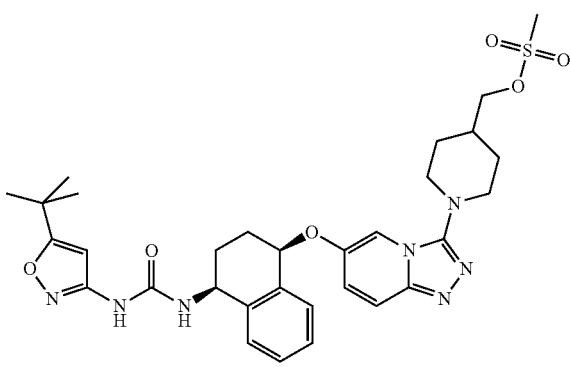 [SMILES: CC(C)(C)c1cc(NC(=O)N[C@H]2CC[C@@H](Oc3ccc4nnc(N5CCC(COS(C)(=O)=O)CC5)n4c3)c3ccccc32)no1]

Intermediate 15b was reacted in an analogous manner to that described in Example 14 step h to give the title compound. LCMS (Method 3): Rt: 3.46 min, m/z 638 [MH⁺].

d. 1-(5-tert-Butyl-isoxazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea (Example 15)

Intermediate 15c was reacted with dimethylamine in an analogous manner to that described in Example 14 step i to give the title compound. LCMS (Method 5): Rt: 3.30 min, m/z 587.4 [MH⁺]. ¹H NMR (400 MHz, d₆-DMSO): 1.28 (9H, s), 1.33-1.47 (2H, m), 1.64-1.75 (1H, m), 1.75-1.84 (2H, m), 1.85-2.11 (4H, m), 2.13-2.20 (8H, m), 2.85-2.99 (2H, m), 3.35-3.47 (2H, m, obscured by water), 4.86-4.94 (1H, m), 5.56 (1H, t, J=4.5 Hz), 6.41 (1H, s), 7.01 (1H, d, J=8.4 Hz), 7.20 (1H, dd, J=9.8, 2.2 Hz), 7.27-7.34 (1H, m), 7.35-7.43 (3H, m), 7.62 (1H, d, J=10.2 Hz), 7.65 (1H, d, J=1.7 Hz), 8.20 (1H, s).

Example 16

1-(3-tert-Butyl-1'-methyl-1'H-[1,4']bipyrazolyl-5-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt

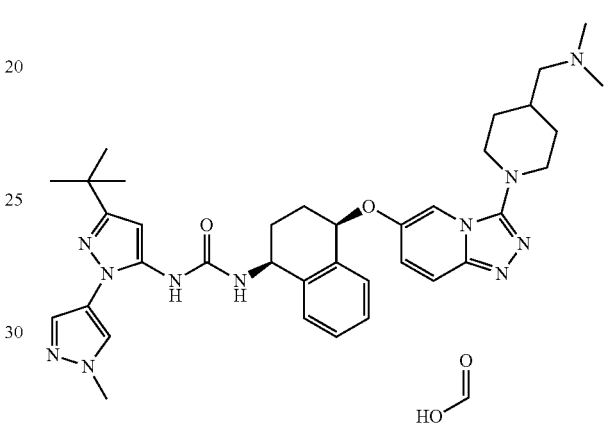

a. 1-(3-tert-Butyl-1'-methyl-1'H-[1,4']bipyrazolyl-5-yl)-3-{(1S,4R)-4-[3-(4-triisopropylsilanyloxymethyl-piperidin-1-yl)-[1,2,4]triazolo[4,3-a]pyridin-6-yloxy]-1,2,3,4-tetrahydro-naphthalen-1-yl}-urea (Intermediate 16a)

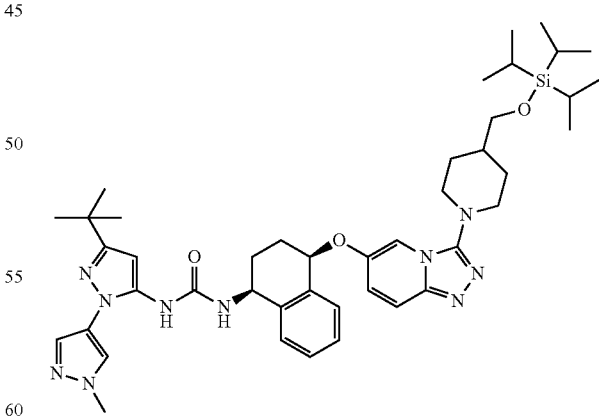

Intermediate 2e was reacted with (3-tert-butyl-1'-methyl-1'H-[1,4']bipyrazolyl-5-yl)-carbamic acid 2,2,2-trichloro-ethyl ester (U.S. Pat. No. 6,492,529) in an analogous manner to that described in Example 14 step f to give the title compound. LCMS (Method 3): Rt: 5.04 min, m/z 795 [MH⁺].

b. 1-(3-tert-Butyl-1'-methyl-1'H-[1,4']bipyrazolyl-5-yl)-3-{(1S,4R)-4-[3-(4-hydroxymethyl-piperidin-1-yl)-[1,2,4]triazolo[4,3-a]pyridin-6-yloxy]-1,2,3,4-tetrahydro-naphthalen-1-yl}-urea (Intermediate 16b)

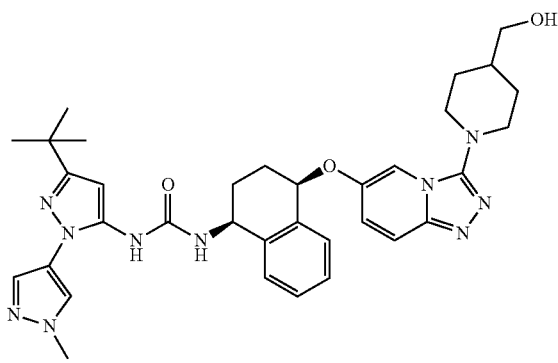 [SMILES: Cn1cc(-n2nc(C(C)(C)C)cc2NC(=O)N[C@H]2CC[C@@H](Oc3ccc4nnc(N5CCC(CO)CC5)n4c3)c3ccccc32)cn1]

Intermediate 16a was reacted in an analogous manner to that described in Example 14 step g to give the title compound. LCMS (Method 3): Rt: 2.96 min, m/z 639 [MH⁺].

c. Methanesulfonic acid 1-(6-{(1R,4S)-4-[3-(3-tert-butyl-1'-methyl-1'H-[1,4']bipyrazolyl-5-yl)-ureido]-1,2,3,4-tetrahydro-naphthalen-1-yloxy}-[1,2,4]triazolo[4,3-a]pyridin-3-yl)-piperidin-4-ylmethyl ester (Intermediate 16c)

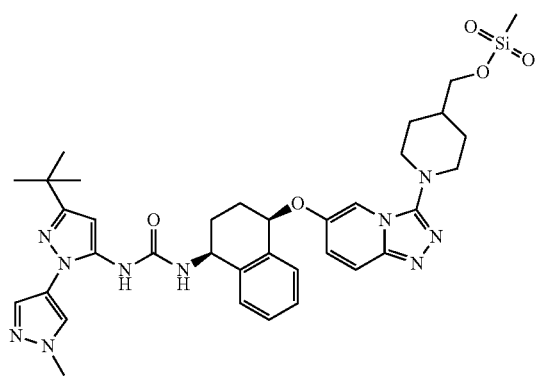

Intermediate 16b was reacted in an analogous manner to that described in Example 14 step h to give the title compound. LCMS (Method 3): Rt: 3.22 min, m/z 717 [MH⁺].

d. 1-(3-tert-Butyl-1'-methyl-1'H-[1,4']bipyrazolyl-5-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt (Example 16)

Intermediate 16c was reacted with dimethylamine in an analogous manner to that described in Example 14 step i to give the title compound. LCMS (Method 5): Rt: 3.05 min, m/z 666.4 [MH⁺]. ¹H NMR (400 MHz, d₆-DMSO): 1.24 (9H, s), 1.33-1.47 (2H, m), 1.63-1.75 (1H, m), 1.75-2.01 (4H, m), 2.01-2.11 (2H, m), 2.13 (2H, d, J=7.5 Hz), 2.15 (6H, s), 2.87-2.98 (2H, m), 3.35-3.47 (2H, m, obscured by water), 3.87 (3H, s), 4.79-4.88 (1H, m), 5.56 (1H, t, J=4.5 Hz), 6.27 (1H, s), 7.12-7.18 (2H, m), 7.26-7.41 (4H, m), 7.59-7.65 (3H, m), 8.00-8.04 (2H, m), 8.23 (0.6H, s).

Example 17

1-[3-tert-Butyl-1'-(2-dimethylamino-ethyl)-1'H-[1,4']bipyrazolyl-5-yl]-3-{4-[3-((2S,6R)-2,6-dimethyl-piperidin-1-yl)-[1,2,4]triazolo[4,3-a]pyridin-6-yloxy]-cyclohexyl}-urea

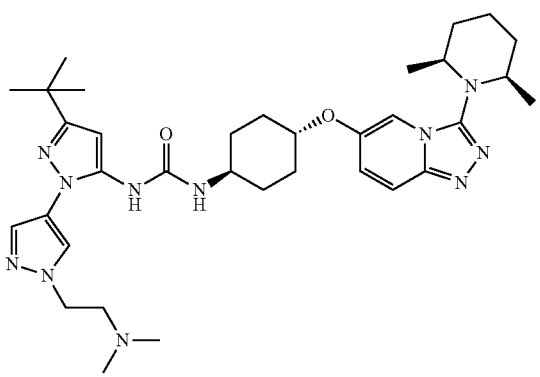 [SMILES: C[C@@H]1CCC[C@H](C)N1c1nnc2ccc(O[C@H]3CC[C@H](NC(=O)Nc4cc(C(C)(C)C)nn4-c4cnn(CCN(C)C)c4)CC3)cn12]

a. 4-[3-((2S,6R)-2,6-Dimethyl-piperidin-1-yl)-[1,2,4]triazolo[4,3-a]pyridin-6-yloxy]-cyclohexylamine (Intermediate 17a)

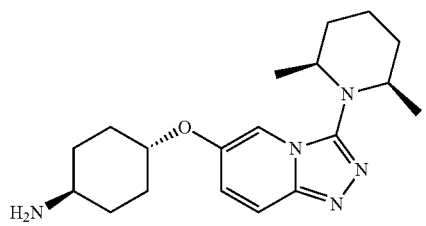 [SMILES: C[C@@H]1CCC[C@H](C)N1c1nnc2ccc(O[C@H]3CC[C@H](N)CC3)cn12]

Sodium hydride (60% in mineral oil, 0.24 g, 6.00 mmol) was added to a stirred solution of trans-4-amino cyclohexanol (0.24 g, 2.08 mmol) in anhydrous DMF (8 mL) at RT under an argon atmosphere. The reaction mixture was stirred at RT for 30 min, then Intermediate 3c (0.50 g, 2.01 mmol) in anhydrous DMF (7 mL) was added and stirred at 60° C. for 4 h. After cooling, the reaction mixture was quenched by careful addition of a saturated aqueous solution of NH₄Cl and water (1:1) and extracted with DCM (3×50 mL). The combined organic layers were washed with water followed by brine, dried and concentrated in vacuo. The resultant residue was purified by FCC using 0-10% [2M NH₃ in MeOH] in DCM to afford the title compound (0.61 g, 88%) as a brown oil. LCMS (Method 3): Rt 2.19 min, m/z 344 [MH⁺].

b. 1-[3-tert-Butyl-1'-(2-hydroxy-ethyl)-1'H-[1,4']bipyrazolyl-5-yl]-3-{4-[3-((2S,6R)-2,6-dimethyl-piperidin-1-yl)-[1,2,4]triazolo[4,3-a]pyridin-6-yloxy]-cyclohexyl}-urea (Intermediate 17b)

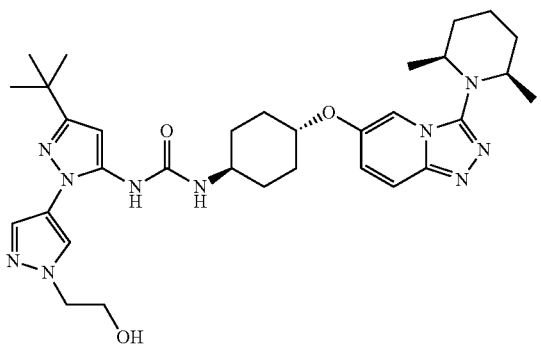 [SMILES: C[C@@H]1CCC[C@H](C)N1c1nnc2ccc(O[C@H]3CC[C@H](NC(=O)Nc4cc(C(C)(C)C)nn4-c4cnn(CCO)c4)CC3)cn12]

A mixture of Intermediate Gc (0.75 g, 1.77 mmol), Intermediate 17a (0.61 g, 1.77 mmol) and DIPEA (0.46 mL, 2.64 mmol) in dioxane (10 mL) was stirred at 70° C. for 18 h. The volatiles were concentrated in vacuo and the resultant residue redissolved in DCM (50 mL), washed with water and brine then dried and evaporated to afford the title compound (1.35g, >100%). LCMS (Method 3): Rt 3.34 min, m/z 619 [MH$^+$].

c. Methanesulfonic acid 2-[3-tert-butyl-5-(3-{4-[3-((2S,6R)-2,6-dimethyl-piperidin-1-yl)-[1,2,4]triazolo[4,3-a]pyridin-6-yloxy]-cyclohexyl}-ureido)-[1,4']bipyrazolyl-1'-yl]-ethyl ester (Intermediate 17c)

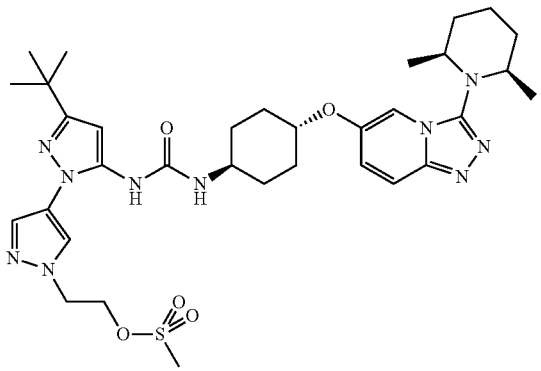 [SMILES: C[C@@H]1CCC[C@H](C)N1c1nnc2ccc(O[C@H]3CC[C@H](NC(=O)Nc4cc(C(C)(C)C)nn4-c4cnn(CCOS(C)(=O)=O)c4)CC3)cn12]

A mixture of Intermediate 17b (0.75 g, 1.21 mmol), methanesulfonyl chloride (140 μL, 1.81 mmol) and DIPEA (0.63 mL, 3.62 mmol) in DCM (15 mL) was stirred at RT for 1 h. The reaction mixture was partitioned between DCM and water. The organic layer was washed with brine, separated through a phase separating cartridge and concentrated in vacuo to afford the title compound (0.82 g, 97%). LCMS (Method 3): Rt 3.59 min, m/z 697 [MH$^+$].

d. 1-[3-tert-Butyl-1'-(2-dimethylamino-ethyl)-1'H-[1,4']bipyrazolyl-5-yl]-3-{4-[3-((2S,6R)-2,6-dimethyl-piperidin-1-yl)-[1,2,4]triazolo[4,3-a]pyridin-6-yloxy]-cyclohexyl}-urea (Example 17)

A mixture of Intermediate 17c (0.82 g, 1.17 mmol) and dimethylamine (2.0M in THF, 12 mL, 24 mmol) was stirred at 60° C. for 18 h in a sealed vial. The volatiles were concentrated in vacuo and the resultant residue was purified by FCC, using 0-10% [2M NH$_3$ in MeOH] in DCM, to afford the title compound (280 mg, 36%). LCMS (Method 5): Rt 3.43 min, m/z 646.4 [MH$^+$]. $^1$H NMR (400 MHz, d$_6$-DMSO): 1.23 (9H, s), 1.28-2.06 (14H, m), 2.19 (6H, s), 2.68 (2H, t, J=6.5 Hz), 3.12-3.21 (1H, m), 3.43-3.54 (1H, m), 4.21 (2H, t, J=6.5 Hz), 4.33-4.43 (1H, m), 6.18 (1H, s), 6.61 (1H, d J=7.4 Hz), 7.18 (1H, dd, J=9.8 2.2 Hz), 7.59 (1H, s), 7.63 (1H, dd, J=9.7 0.6 Hz), 7.71-7.73 (1H, m), 7.92 (1H, s), 8.02 (1H, s), 8.18 (0.5H, s).

Example 18

1-(5-tert-Butyl)-2-p-tolyl-2H-pyrazol-3-yl)-3-{4-[3-((S)-2-methyl-piperidin-1-yl)-[1,2,4]triazolo[4,3-a]pyridin-6-yloxy]-cyclohexyl}-urea

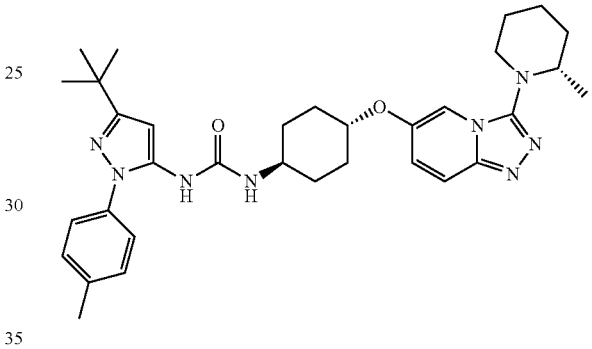

a. 4-[3-((2S,6R)-2,6-Dimethyl-piperidin-1-yl)-[1,2,4]triazolo[4,3-a]pyridin-6-yloxy]-cyclohexylamine (Intermediate 18a)

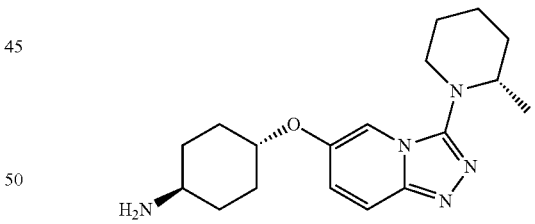

Sodium hydride (60% in mineral oil, 0.26 g, 6.39 mmol) was added to a stirred solution of trans-4-amino cyclohexanol (0.397 g, 3.45 mmol) in anhydrous DMF (10 mL) at RT under an argon atmosphere. The reaction mixture was stirred at RT for 30 min, then Intermediate 2d (0.50 g, 2.13 mmol) in anhydrous DMF (4 mL) was added and stirred at 60° C. for 10 h. After cooling, the reaction mixture was quenched by careful addition of a saturated aqueous solution of NH$_4$Cl and water (1:1) and extracted with EtOAc and then DCM. The combined organic extracts were concentrated in vacuo and the resultant residue was purified by FCC, using 0-25% [2M NH$_3$ in MeOH] in DCM, to afford the title compound (0.193 g, 27%) as an orange residue. LCMS (Method 3): Rt 2.00 min, m/z 330 [MH$^+$].

b. 1-(5-tert-Butyl)-2-p-tolyl-2H-pyrazol-3-yl)-3-{4-[3-((S)-2-methyl-piperidin-1-yl)-[1,2,4]triazolo[4,3-a]pyridin-6-yloxy]-cyclohexyl}-urea (Example 18)

A mixture of (5-tert-butyl-2-p-tolyl-2H-pyrazol-3-yl)-carbamic acid 2,2,2-trichloro-ethyl ester (73.7 mg, 0.182 mmol), Intermediate 18a (40 mg, 0.121 mmol) and DIPEA (63.2 μL, 0.363 mmol) in dioxane (2 mL) was stirred at 60° C. for 24 h. The volatiles were concentrated in vacuo and the resultant residue redissolved in DCM washed with water and brine then dried and evaporated to give a residue that was purified by MDAP to afford the title compound as a beige foam (45 mg, 63%). LCMS (Method 5): Rt 4.69 min, m/z 585.4 [MH$^+$].
$^1$H NMR (400 MHz, d$_6$-DMSO): 0.89 (3H, d J=6.2 Hz), 1.25 (9H, s), 1.27-2.08 (14H, m), 2.36 (3H, s), 2.87-2.97 (1H, m), 3.11-3.20 (2H, m), 3.41-3.53 (1H, m), 4.04-4.11 (1H, m), 4.31-4.40 (1H, m), 6.25 (1H, s), 6.55 (1H, d, J=7.4 Hz), 7.15 (1H, dd, J=9.9 2.2 Hz), 7.28-7.35 (4H, m), 7.54 (1H, d, J=1.6 Hz), 7.60 (1H, d, J=9.7 Hz), 7.95 (1H, s).

Example 19

1-{5-tert-Butyl-2-[3-(2-dimethylamino-ethoxy)-phenyl]-2H-pyrazol-3-yl}-3-{4-[3-((S)-2-methyl-piperidin-1-yl)-[1,2,4]triazolo[4,3-a]pyridin-6-yloxy]-cyclohexyl}-urea

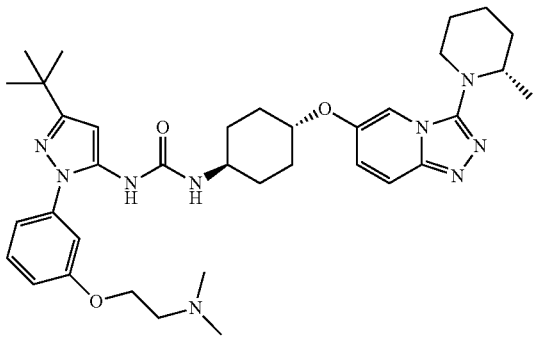 [SMILES: C[C@H]1CCCCN1c1nnc2ccc(O[C@H]3CC[C@H](NC(=O)Nc4cc(C(C)(C)C)nn4-c4cccc(OCCN(C)C)c4)CC3)cn12]

a. 1-{5-tert-Butyl-2-[3-(2-hydroxy-ethoxy)-phenyl]-2H-pyrazol-3-yl}-3-{4-[3-((S)-2-methyl-piperidin-1-yl)-[1,2,4]triazolo[4,3-a]pyridin-6-yloxy]-cyclohexyl}-urea (Intermediate 19a)

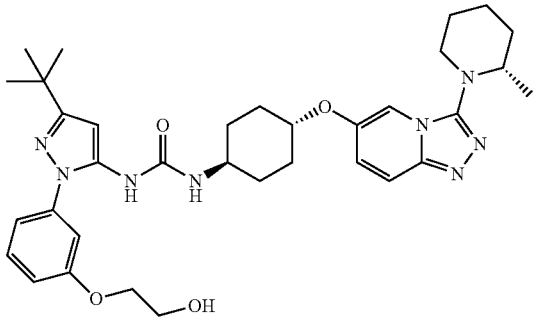 [SMILES: C[C@H]1CCCCN1c1nnc2ccc(O[C@H]3CC[C@H](NC(=O)Nc4cc(C(C)(C)C)nn4-c4cccc(OCCO)c4)CC3)cn12]

A mixture of {5-tert-butyl-2-[3-(2-hydroxy-ethoxy)-phenyl]-2H-pyrazol-3-yl}-carbamic acid 2,2,2-trichloro-ethyl ester (WO 2007/063868, which is incorporated herein by reference in its entirety, 287.6 mg, 0.638 mmol), Intermediate 18a (140 mg, 0.425 mmol) and DIPEA (223 μL, 1.28 mmol) in dioxane (10 mL) was stirred at 60° C. for 18 h. The volatiles were concentrated in vacuo and the resultant residue was purified by FCC, using 0-10% [2M NH$_3$ in MeOH] in DCM, to afford the title compound (222 mg, 82%). LCMS (Method 3): Rt 3.35 min, m/z 631 [MH$^+$].

b. Methanesulfonic acid 2-{3-[3-tert-butyl-5-(3-{4-[3-((S)-2-methyl-piperidin-1-yl)-[1,2,4]triazolo[4,3-a]pyridin-6-yloxy]-cyclohexyl}-ureido)-pyrazol-1-yl]-phenoxy}-ethyl (Intermediate 19b)

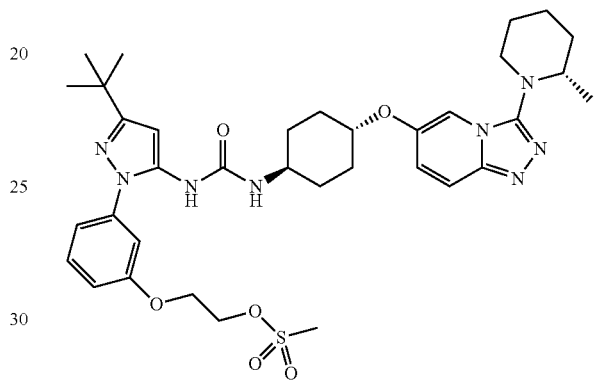

A mixture of Intermediate 19a (216 mg, 0.342 mmol), methanesulfonyl chloride (39.7 μL, 0.513 mmol) and DIPEA (179 μL, 1.03 mmol) in DCM (5 mL) was stirred at RT for 30 min. The reaction mixture was partitioned between DCM and water. The organic layer was washed with brine, separated through a phase separating cartridge and concentrated in vacuo to afford the title compound (233 mg, 96%) as a cream foam. LCMS (Method 3): Rt 3.69 min, m/z 709 [MH$^+$].

c. 1-{5-tert-Butyl-2-[3-(2-dimethylamino-ethoxy)-phenyl]-2H-pyrazol-3-yl}-3-{4-[3-((S)-2-methyl-piperidin-1-yl)-[1,2,4]triazolo[4,3-a]pyridin-6-yloxy]-cyclohexyl}-urea (Example 19)

A mixture of Intermediate 19b (233 mg, 0.33 mmol) and dimethylamine (2.0M in THF, 1.65 mL, 3.30 mmol) was stirred at 60° C. for 18 h in a sealed vial. The volatiles were concentrated in vacuo, the resultant residue was redissolved in EtOAc, washed with water and brine then dried and evaporated to give a residue that was purified by FCC using 0-10% [2M NH$_3$ in MeOH] in DCM and then MDAP to afford the title compound (62 mg, 28%). LCMS (Method 5): Rt 3.38 min, m/z 658.4 [MH$^+$]. $^1$H NMR (400 MHz, d$_6$-DMSO): 1.26 (9H, s), 1.28-2.08 (14H, m), 2.25 (6H, s), 2.68 (2H, t, J=5.7 Hz), 2.87-2.96 (1H, m), 3.11-3.19 (2H, m), 3.25-3.35 (2H, m), 3.43-3.53 (3H, m), 4.10 (2H, t, J=5.7 Hz), 4.31-4.40 (1H, m), 6.26 (1H, s), 6.58 (1H, d, J=7.5 Hz), 6.93-6.97 (1H, m), 7.01-7.07 (2H, m), 7.15 (1H, dd, J=9.8 2.2 Hz), 7.39 (1H, t, J=8.0 Hz), 7.54 (1H, d, J=1.5 Hz), 7.60 (1H, t, J=9.9 Hz), 8.03 (1H, s), 8.17 (1H, s).

Example 20

1-{5-(Cyano-dimethyl-methyl)-2-[3-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl}-urea

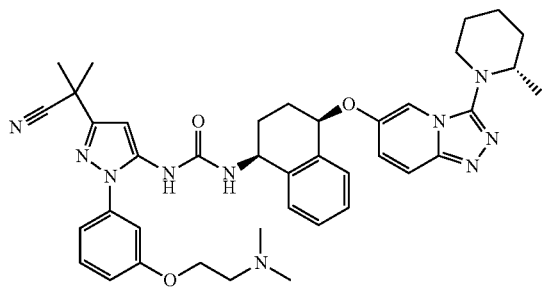 [SMILES: C[C@H]1CCCCN1c1nnc2ccc(O[C@@H]3CC[C@H](NC(=O)Nc4cc(C(C)(C)C#N)nn4-c4cccc(OCCN(C)C)c4)c4ccccc43)cn12]

a. 3-Hydrazinophenol (Intermediate 20a)

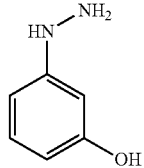

To a stirred, ice cooled solution of 3-aminophenol (2.00 g, 18.3 mmol) in concentrated HCl (20 mL) was added dropwise a solution of sodium nitrite (1.33 g, 19.24 mmol) in H$_2$O (10 mL), ensuring the internal temperature did not exceed 10° C. After 10 min, a solution of tin (II) chloride (7.645 g, 40.3 mmol) in concentrated HCl (10 mL) was added dropwise, and the ice bath removed. After stirring at RT for 45 min, the reaction was basified to pH 10 with careful addition of 10 M NaOH solution (50 mL), and then extracted with EtOAc (3×). The organic extracts were dried over MgSO$_4$, concentrated in vacuo and triturated with Et$_2$O to afford the title compound as a brown solid (353 mg, 16%). $^1$H NMR (300 MHz, d$_6$-DMSO): 3.83 (2H, br s), 5.96-6.02 (1H, m), 6.15-6.21 (1H, m), 6.22 (1H, t, J=2.2 Hz), 6.52 (1H, br s), 6.84 (1H, t, J=8.0 Hz), 8.91 (1H, br s).

b. 2-[5-Amino-1-(3-hydroxy-phenyl)-1H-pyrazol-3-yl]-2-methyl-propionitrile (Intermediate 20b)

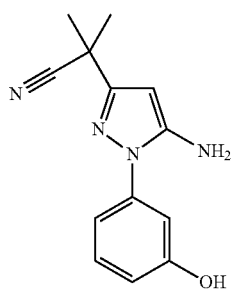 [SMILES: CC(C)(C#N)c1cc(N)n(-c2cccc(O)c2)n1]

2,2-Dimethyl-3-oxo-pentanedinitrile (WO 2008/034008, which is incorporated herein by reference in its entirety, 353 mg, 2.80 mmol) and Intermediate 20a (387 mg, 2.80 mmol) were suspended in EtOH (10 mL) and concentrated HCl was added (711 µL, 8.53 mmol) and the reaction was refluxed for 90 min. The reaction was cooled, concentrated in vacuo and partitioned between H$_2$O and EtOAc. The organic layer was separated, dried over MgSO$_4$ and concentrated in vacuo and the resulting oil was triturated with pentane/Et$_2$O (9:1) to afford the title compound as a brown solid (363 mg, 53%). LCMS (Method 3): Rt 2.77 min, m/z 243.3 [MH$^+$].

c. 2-(5-Amino-1-{3-[2-(tetrahydro-pyran-2-yloxy)-ethoxy]-phenyl}-1H-pyrazol-3-yl)-2-methyl-propionitrile (Intermediate 20c)

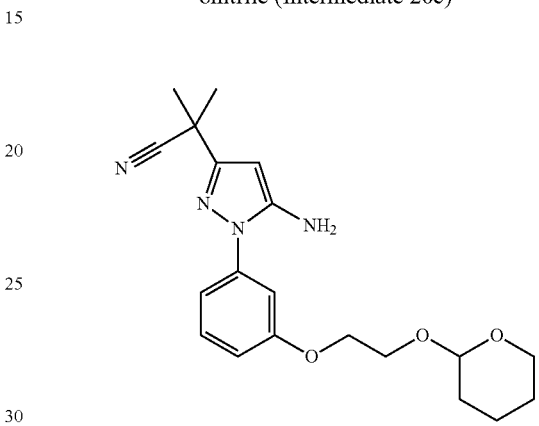

To an ice cooled solution of Intermediate 20b (363 mg, 1.50 mmol), 2-(tetrahydro-2H-pyran-2-yloxy)ethanol (329 mg, 305 µL, 2.25 mmol) and triphenylphosphine (786 mg, 3.00 mmol) in anhydrous THF (10 mL) was added dropwise diisopropyl azodicarboxylate (606 mg, 590 µL), and the ice bath removed and stirring continued under an Ar atmosphere. After 3 h, a further 1.0 eq of diisopropyl azodicarboxylate was added and the reaction stirred overnight. The reaction mixture was then concentrated in vacuo and subjected to FCC, eluting with 5-50% EtOAc in cyclohexane. The isolated product was repurified using FCC, eluting with 2.5-7.5% Et$_2$O in DCM, to afford the title compound as a yellow oil (317 mg, 57%). LCMS (Method 3): Rt 3.67 min, m/z 393.3 [M+Na].

d. (5-(Cyano-dimethyl-methyl)-2-{3-[2-(tetrahydro-pyran-2-yloxy)-ethoxy]-phenyl}-2H-pyrazol-3-yl)-carbamic acid 2,2,2-trichloro-ethyl ester (Intermediate 20d)

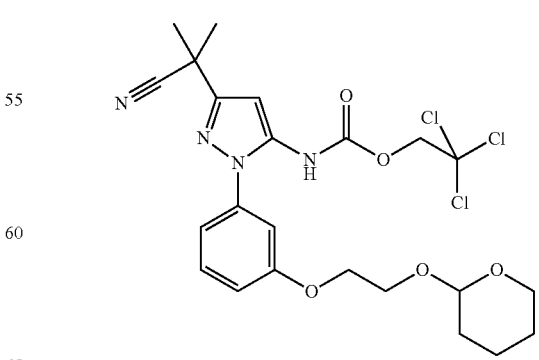

Intermediate 20c (317 mg, 0.86 mmol) was dissolved in EtOAc (2.5 mL) and 1M NaOH solution (1.4 mL, 2.14 mmol)

and cooled in an ice bath. While stirring, 2,2,2-trichloroethyl chloroformate (227 mg, μL, 1.07 mmol) was then added dropwise, and the ice bath removed. After 30 min, a further 0.65 eq. of 2,2,2-trichloroethyl chloroformate was added, and the reaction continued. After 30 min, a further 0.65 eq. of 2,2,2-trichloroethyl chloroformate was added, and the reaction continued overnight. The reaction was then partitioned between H$_2$O and EtOAc, the organic layer was separated, and the aqueous layer extracted again with EtOAc. The combined organics were dried over MgSO$_4$, concentrated in vacuo and subjected to FCC, eluting with 5-30% EtOAc in cyclohexane, to afford the title compound as a light yellow oil (375 mg, 80%). LCMS (Method 3): Rt 4.41 min, m/z 567, 569 [M+Na].

e. {5-(Cyano-dimethyl-methyl)-2-[3-(2-hydroxy-ethoxy)-phenyl]-2H-pyrazol-3-yl}-carbamic acid 2,2,2-trichloro-ethyl ester (Intermediate 20e)

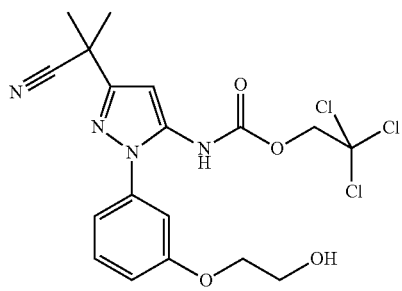 [SMILES: CC(C)(C#N)c1cc(NC(=O)OCC(Cl)(Cl)Cl)n(-c2cccc(OCCO)c2)n1]

Intermediate 20d (375 mg, 0.69 mmol) was dissolved in MeOH (5 mL) and loaded onto a 20 g SCX-2 SPE cartridge (pre-conditioned with MeOH). The cartridge was then washed with MeOH (2 column volumes) and the eluent concentrated in vacuo to afford the title compound as a colorless oil (283 mg, 89%). LCMS (Method 3): Rt 3.71 min, m/z 461, 463 [MH$^+$].

f. 1-{5-(Cyano-dimethyl-methyl)-2-[3-(2-hydroxy-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 20f)

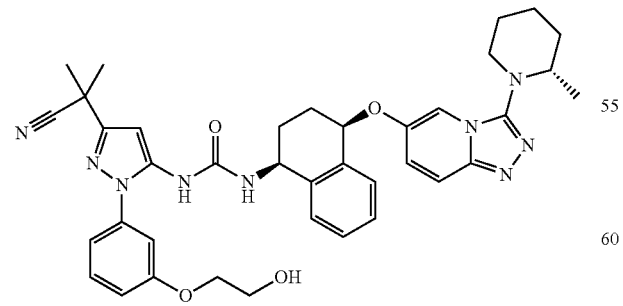

The title compound was prepared using Intermediate 20e and Intermediate 2 in an analogous fashion to the procedure described for Intermediate A step d. LCMS (Method 3): Rt 3.39 min, m/z 690.4 [MH$^+$].

g. Methanesulfonic acid 2-{3-[3-(cyano-dimethyl-methyl)-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-phenoxy}-ethyl ester (Intermediate 20g)

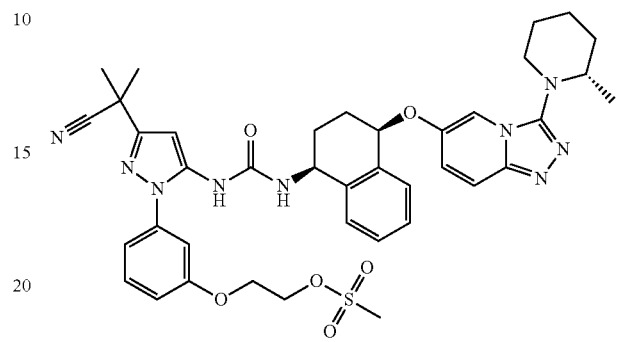

The title compound was prepared using Intermediate 20f in an analogous fashion to the procedures described for Intermediate A step e. LCMS (Method 3): Rt 3.64 min, m/z 768.5 [MH$^+$].

h. 1-{5-(Cyano-dimethyl-methyl)-2-[3-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl}-urea (Example 20)

The title compound was prepared using Intermediate 20g using the general displacement procedure described for Example 1. LCMS (Method 5): Rt 3.46 min, m/z 717.5 [MH$^+$].

Example 21

1-{5-(Cyano-dimethyl-methyl)-2-[3-(2-dimethylamino-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea

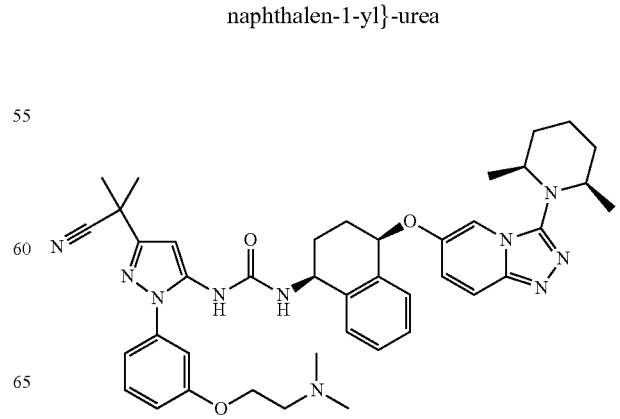

a. 1-{5-(Cyano-dimethyl-methyl)-2-[3-(2-hydroxy-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Intermediate 21a)

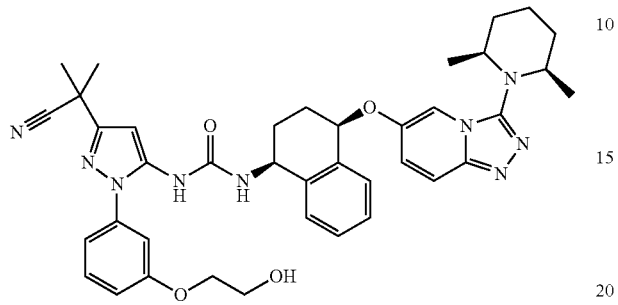

The title compound was prepared using Intermediate 20e and Intermediate 3 in an analogous fashion to the procedure described for Intermediate A step d. LCMS (Method 3): Rt 3.61 min, m/z 704.5 [MH+].

b. Methanesulfonic acid 2-{3-[3-(cyano-dimethyl-methyl)-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-phenoxy}-ethyl ester (Intermediate 21b)

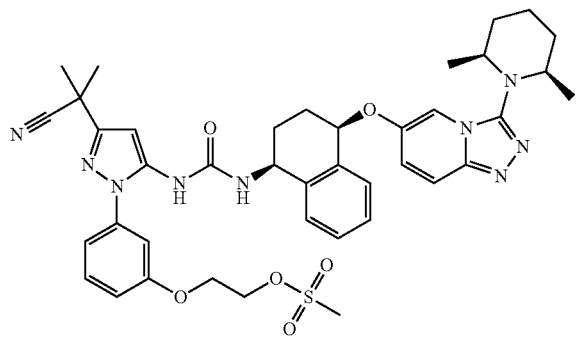 [SMILES: C[C@@H]1CCC[C@H](C)N1c1nnc2ccc(O[C@@H]3CC[C@H](NC(=O)Nc4cc(C(C)(C)C#N)nn4-c4cccc(OCCOS(C)(=O)=O)c4)c4ccccc43)cn12]

The title compound was prepared using Intermediate 21a in an analogous fashion to the procedures described for Intermediate A step e. LCMS (Method 3): Rt 3.85 min, m/z 782.5 [MH+].

c. 1-{5-(Cyano-dimethyl-methyl)-2-[3-(2-dimethylamino-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Example 21)

The title compound was prepared using Intermediate 21b using the general displacement procedure described for Example 1. LCMS (Method 3): Rt 2.83 min, m/z 731.5 [MH+].

Intermediate 22. [5-tert-Butyl-2-(2-methoxyethyl)-2H-pyrazol-3-yl]carbamic acid 2,2,2-trichloroethyl ester

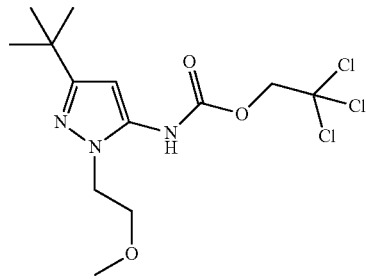 [SMILES: COCCn1nc(C(C)(C)C)cc1NC(=O)OCC(Cl)(Cl)Cl]

a. 5-tert-Butyl-2-(2-methoxyethyl)-2H-pyrazol-3-ylamine (Intermediate 22b)

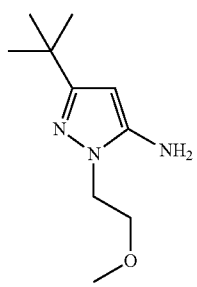

A stirred suspension of (2-methoxyethyl) hydrazine oxalic acid (0.50 g, 2.77 mmol) and 4,4-dimethyl-3-oxopentanenitrile (0.347 g, 2.77 mmol) in ethanol (6 mL) was heated at 85° C. for 4.5 h during which time all solids dissolved. The reaction mixture was allowed to cool overnight and then the solvent was evaporated. The residue was dissolved in dichloromethane (20 mL) and washed with saturated aqueous NaHCO$_3$ (10 mL). The organic layer was separated using a phase separator cartridge and evaporated. The residual oil was dissolved in diethyl ether and evaporated to afford the title compound (0.538 g, 98%) as a solid. $^1$H NMR (300 MHz, CDCl$_3$): 1.26 (9H, s), 3.33 (3H, s), 3.67 (2H, t, J 4.3 Hz), 3.95 (2H, br s), 4.13 (2H, t, J 4.6 Hz), 5.36 (1H, s).

b. [5-tert-Butyl-2-(2-methoxy-ethyl)-2H-pyrazol-3-yl]carbamic acid 2,2,2-trichloroethyl ester (Intermediate 22)

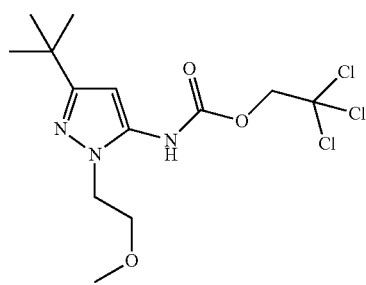 [SMILES: COCCn1nc(C(C)(C)C)cc1NC(=O)OCC(Cl)(Cl)Cl]

Intermediate 23.
[5-tert-Butyl-2-propyl-2H-pyrazol-3-yl]carbamic acid 2,2,2-trichloroethyl ester

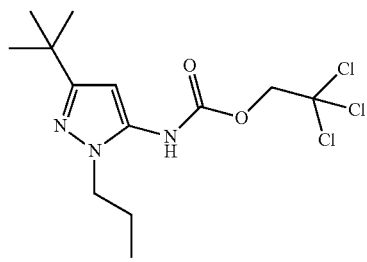 [SMILES: CCCn1nc(C(C)(C)C)cc1NC(=O)OCC(Cl)(Cl)Cl]

a. 5-tert-Butyl-2-propyl-2H-pyrazol-3-ylamine (Intermediate 23a)

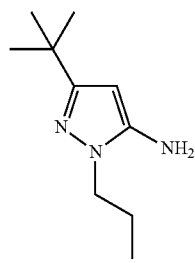

A stirred solution of propylhydrazine hydrochloride (0.50 g, 4.52 mmol) and 4,4-dimethyl-3-oxopentanenitrile (0.566 g, 2.77 mmol) in ethanol (6 mL) was treated with concd. HCl (1 drop) and heated at 85° C. for 4.5 h. The reaction mixture was allowed to cool overnight and then the solvent was evaporated. The residue was dissolved in dichloromethane (20 mL) and washed with saturated aqueous NaHCO$_3$ (10 mL). The organic layer was separated using a phase separator cartridge and evaporated. The residual oil was dissolved in diethyl ether and evaporated to afford the title compound (0.776 g, 95%) as an oil that slowly solidified. $^1$H NMR (300 MHz, CDCl$_3$): 0.92 (3H, t, J 7.4 Hz), 1.25 (9H, s), 1.87-1.79 (2H, sextet, J 7.4 Hz), 3.35 (2H, br s), 3.85 (2H, t, J 7.4 Hz), 5.41 (1H, s).

b. [5-tert-Butyl-2-propyl-2H-pyrazol-3-yl]carbamic acid 2,2,2-trichloroethyl ester (Intermediate 23)

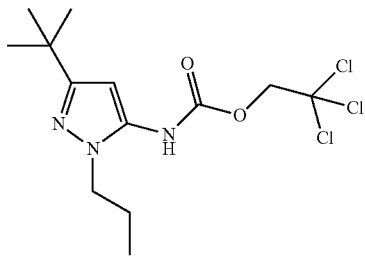 [SMILES: CCCn1nc(C(C)(C)C)cc1NC(=O)OCC(Cl)(Cl)Cl]

To a stirred mixture of Intermediate 23a (0.774 g, 4.27 mmol) in ethyl acetate (4 mL) and 1 M aqueous NaOH (7.7 mL, 7.7 mmol) was added 2,2,2-trichloroethyl chloroformate (0.62 mL, 4.50 mmol) and the mixture was stirred at room temperature for 1.5 h. The mixture was diluted with water (50 mL) and extracted with ethyl acetate (2×25 mL). The combined organic extracts were washed with water and saturated aqueous NaCl, then evaporated to give the title compound (1.57 g) as an oil. LCMS (Method 3): Rt 4.28 min, m/z 356/358/360 [MH$^+$]. $^1$H NMR (300 MHz, CDCl$_3$): 0.90 (3H, t, J 7.5 Hz), 1.28 (9H, s), 1.78-1.87 (2H, m), 3.92 (2H, t, J 7.4 Hz), 4.83 (2H, s), 6.08 (1H, s), 6.46 (1H, s).

Intermediate 24.
[5-tert-Butyl-2-ethyl-2H-pyrazol-3-yl]carbamic acid 2,2,2-trichloroethyl ester

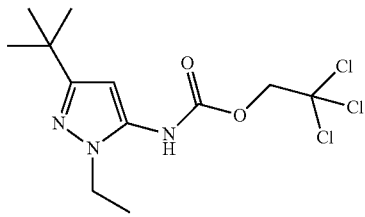 [SMILES: CCn1nc(C(C)(C)C)cc1NC(=O)OCC(Cl)(Cl)Cl]

To a stirred mixture of 3-tert-butyl-1-ethyl-1H-pyrazole-5-amine (0.500 g, 2.99 mmol) in ethyl acetate (7.5 mL) and 1 M aqueous NaOH (7.5 mL, 7.5 mmol), cooled in an ice bath, was added 2,2,2-trichloroethyl chloroformate (0.453 mL, 3.29 mmol) and the mixture was stirred for 45 min. The mixture was diluted with water and extracted twice with ethyl acetate. The combined organic extracts were dried (MgSO$_4$) and evaporated. The residue was crystallised from pentane-diethyl ether (1:1) to give the title compound (0.078 g) as a white solid. The mother liquors were evaporated and purified by column chromatography (0-40% EtOAc/cyclohexane) to give the title compound (0.817 g) as a colorless oil (Total yield 0.895 g, 87%). LCMS (Method 3): Rt 4.09 min, m/z 342/344/346 [MH$^+$]. $^1$H NMR (300 MHz, CDCl$_3$): 1.44 (12H, m), 4.78-4.83 (2H, m), 4.88 (2H, s), 6.53 (1H, s), 9.82 (1H, s).

---

To a stirred mixture of Intermediate 22a (0.535 g, 2.71 mmol) in ethyl acetate (4 mL) and 1 M aqueous NaOH (4.9 mL, 4.90 mmol) was added 2,2,2-trichloroethyl chloroformate (0.40 mL, 2.90 mmol) and the mixture was stirred at room temperature for 1.5 h. The mixture was diluted with water (50 mL) and extracted with ethyl acetate (2×25 mL). The combined organic extracts were washed with water and saturated aqueous NaCl, then evaporated. The residual oil was dissolved in diethyl ether and evaporated to give the title compound (1.06 g) as an oil. LCMS (Method 3): Rt 4.17 min, m/z 372/374/376 [MH$^+$]; $^1$H NMR (300 MHz, CDCl3): 1.30 (9H, s), 3.44 (3H, s), 3.74 (2H, t, J 4.3 Hz), 4.29 (2H, t, J 4.3 Hz), 4.82 (2H, s), 6.26 (1H, s), 8.93 (1H, s).

Intermediate I. (1S,4R)-4-{3-[4-(2-Dimethylamino-ethoxy)-piperidin-1-yl]-[1,2,4]triazolo[4,3-a]pyridin-6-yloxy}-1,2,3,4-tetrahydro-naphthalen-1-ylamine

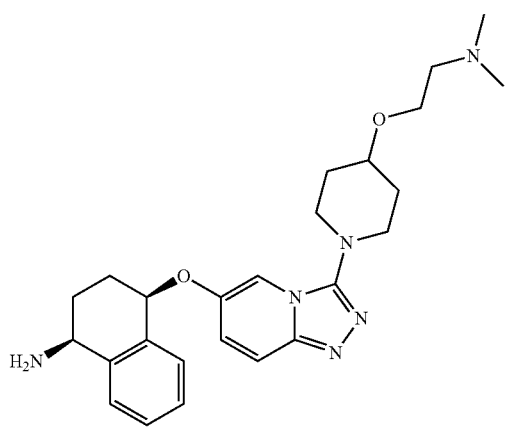 [SMILES: CN(C)CCOC1CCN(c2nnc3ccc(O[C@@H]4CC[C@H](N)c5ccccc54)cn23)CC1]

a. 3-Chloro-6-fluoro-[1,2,4]triazolo[4,3-a]pyridine (Intermediate Ia)

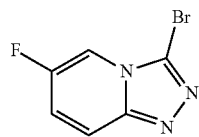

Intermediate 14a (908 mg, 6.60 mmol) was dissolved in DCM (50 mL) and N-bromosuccinimide (1.29 g, 7.26 mmol) added. The reaction was heated to 45° C. for 4 h, then cooled and partitioned between DCM (150 mL) and saturated aqueous NaHCO$_3$ (150 mL), and extracted into DCM (3×). The combined organic layers were washed with brine, dried (MgSO$_4$) and evaporated in vacuo. Purification by FCC, using 0-5% [2M NH$_3$ in MeOH] in DCM, gave the title compound (900 mg, 63%). LCMS (Method 1): Rt 1.94 min, m/z 216/218 [MH$^+$].

b. {2-[1-(6-Fluoro-[1,2,4]triazolo[4,3-a]pyridin-3-yl)-piperidin-4-yloxy]-ethyl}-dimethyl-ami (Intermediate Ib)

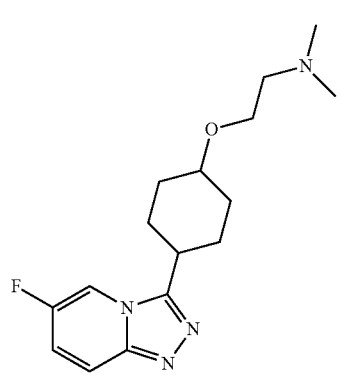 [SMILES: CN(C)CCOC1CCC(c2nnc3ccc(F)cn23)CC1]

A solution of Intermediate Ia (435 mg, 2.01 mmol) and Dimethyl-[2-(piperidin-4-yloxy)-ethyl]-amine (1.09 g, 6.01 mmol) in DMA (6.0 mL) was heated in the microwave at 180° C. for 6 h. The cooled mixture was applied to an SCX-2 cartridge (20 g), washing with methanol then eluting basic components with 2 M NH$_3$ in MeOH. Product containing fractions were combined and concentrated in vacuo. The residue was purified by FCC, using 0-10% [2M NH$_3$ in MeOH] in DCM, to give the title compound as yellow oil (570 mg, 92%). LCMS (Method 4): Rt 1.61 and 0.41 min, m/z 308 [MH$^+$].

c. (1S,4R)-4-{3-[4-(2-Dimethylamino-ethoxy)-piperidin-1-yl]-[1,2,4]triazolo[4,3-a]pyridin-6-yloxy}-1,2,3,4-tetrahydro-naphthalen-1-ylamine (Intermediate I)

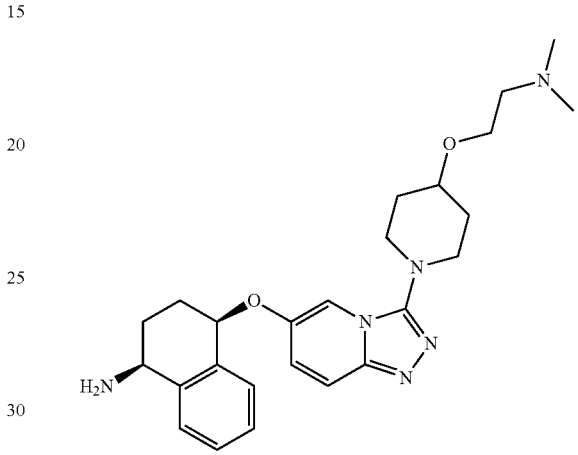

To a solution of Intermediate 1 (318 mg, 1.95 mmol) in DMF (8 mL) was added NaH (60% dispersion in oil, 223 mg, 5.57 mmol) and the mixture stirred at RT for 15 min. A solution of Intermediate Ib (570 mg, 1.85 mmol) in DMF (7 mL) was added and the mixture stirred at RT for 18 hours. The cooled mixture was diluted with water and extracted with DCM (5×20 mL). The combined organics were dried and concentrated in vacuo. The residue was purified by FCC, using 0-10% [2M NH$_3$ in MeOH] in DCM, to give the title compound as a brown gum (294 mg, 34%). LCMS (Method 4): Rt 1.65 min and 0.42 min, m/z 451 [MH$^+$].

Intermediate J (WO2013083604). (1S,4R)-4-[3-((R)-3-Triisopropylsilanyloxymethyl-piperidin-1-yl)-[1,2,4]triazolo[4,3-a]pyridin-6-yloxy]-1,2,3,4-tetrahydro-naphthalen-1-ylamine

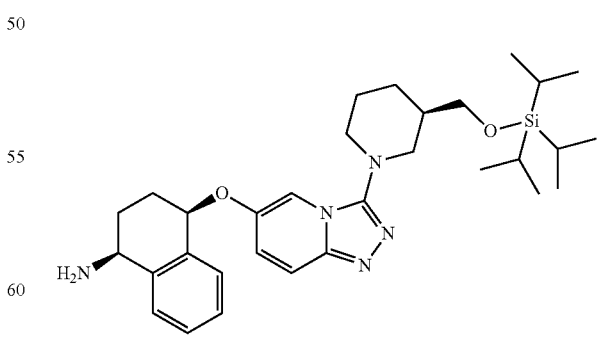

Intermediate K (WO2013/083604, which is incorporated herein by reference in its entirety). (1S,4R)-4-[3-((S)-3-Triisopropylsilanyloxymethyl-piperidin-1-yl)-[1,2,4]triazolo[4,3-a]pyridin-6-yloxy]-1,2,3,4-tetrahydro-naphthalen-1-ylamine.

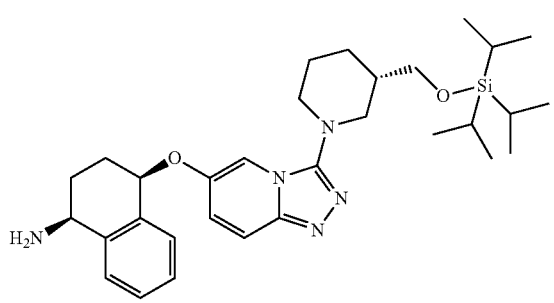 [SMILES: CC(C)[Si](OC[C@H]1CCCN(c2nnc3ccc(O[C@@H]4CC[C@H](N)c5ccccc54)cn23)C1)(C(C)C)C(C)C]

General Urea Formation Procedure (GP1).

A solution of the appropriate LHS (Ex. 20-35) (0.273 mmol), the appropriate Intermediate 14e or Intermediate I-K (0.273 mmol) and DIPEA (0.409 mmol) in dioxane (2 mL) was heated at 60° C. for 48 h. The reaction mixture was cooled and diluted with DCM (5 mL). The organic layer was washed with water (3×5 mL), passed through a phase separator and concentrated in vacuo. The residue was purified by FCC, using 0-10% [2M NH3 in MeOH] in DCM to afford the desired urea intermediate or Examples 22-27 (40-80%).

General Procedure for TBAF Deprotection, Mesylation and Displacement (GP2).

Tetrabutylammonium fluoride (1M solution in THF, 0.211 mmol) was added to a solution of the appropriate triisopropylsilanyloxymethyl-piperidin-intermediate (Ex. 30-37) (0.151 mmol) in THF (3 mL) and the reaction mixture was stirred at RT for 1 h. The mixture was diluted with DCM (5 mL) and washed with water (2×5 mL) and brine (5 mL). The organic layer was passed through a phase separator and concentrated in vacuo. The residue was purified by FCC, using 0-10% [2M NH3 in MeOH] in DCM to afford the desired hydroxyl-intermediate (60-80%).

Methanesulfonyl chloride (0.13 mmol) was added to a solution of the appropriate hydroxyl-intermediate (0.08 mmol) and DIPEA (0.26 mmol) in DCM (1.5 mL) and the reaction mixture was stirred at RT for 1 h. The mixture was diluted with DCM (5 mL) and washed with water (3×5 mL). The organic layer was passed through a phase separator and concentrated in vacuo to afford the desired mesylate intermediate in quantitative yields.

A mixture of the appropriate mesylate intermediate (0.14 mmol) and an appropriate amine [see table below] (2.15 mmol) in anhydrous THF (3 mL) was stirred at 40° C. for 18 h in a sealed vial. The volatiles were concentrated in vacuo and the resultant residue was purified by HPLC (Gemini C18, 20-40% MeCN in H$_2$O, 0.1% HCO$_2$H, 18 ml/min.) and freeze dried to afford the Examples 28-37 (30-50%).

| Example No. | LHS | Amine | General method | Intermediate Used | Example Structure | NMR (400 MHz) δ | LCMS |
|---|---|---|---|---|---|---|---|
| 22 | ![LHS structure] US2004/192653 | N/A | GP1 | I | 1-(5-tert-Butyl-2-methyl-2H-pyrazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt | (d$_6$-DMSO): 1.16 (9H, s), 1.69-1.79 (2H, m), 1.81-2.06 (5H, m), 2.09-2.16 (1H, m), 2.75 (3H, s), 2.77 (3H, s), 3.00-3.06 (2H, m), 3.23-3.39 (4H, m), 3.55 (3H, s), 3.59-3.65 (1H, m), 3.74 (2H, t, J 5.1 Hz), 4.80-4.85 (1H, m), 5.56 (1H, s), 7.03 (1H, d, J 8.7 Hz), 7.23-7.28 (2H, m), 7.33-7.37 (3H, m), 7.63 (1H, d, J 10.0 Hz), 7.72 (1H, s), 8.54 (1H, s), 9.67 (1H, br s) | (Method 5): Rt 3.03 mins, m/z 630 [MH$^+$]. |

| Example No. | LHS | Amine | General method | Intermediate Used | Example Structure | NMR (400 MHz) δ | LCMS |
|---|---|---|---|---|---|---|---|
| 23 | ![Troc-pyrazole structure] WO2013/083604 | N/A | GP1 | I | 1-[5-tert-Butyl-2-(2-hydroxy-ethyl)-2H-pyrazol-3-yl]-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt | (d₆-DMSO): 1.21 (9H, s), 1.73-1.85 (2H, m), 1.85-2.12 (5H, m), 2.13-2.22 (1H, m), 2.54 (1H, s), 2.80 (3H, s), 2.81 (3H, s), 3.02-3.11 (2H, m), 3.63-3.70 (3H, m), 3.77-3.82 (2¼H, m), 3.98 (2H, t, J 5.9 Hz), 4.83-4.90 (1H, m), 5.59 (1H, t, J 4.2 Hz), 6.07 (1H, s), 7.20 (1H, d, J 8.7 Hz), 7.23-7.33 (2H, m), 7.35-7.43 (3H, m), 7.66 (1H, d, J 9.9 Hz), 7.74 (1H, s), 8.47 (1H, br s) plus 4 protons obscured by solvent peaks | (Method 5): Rt 2.91 mins, m/z 660 [MH⁺]. |

| Example No. | LHS | Amine | General method | Intermediate Used | Example Structure | NMR (400 MHz) δ | LCMS |
|---|---|---|---|---|---|---|---|
| 24 | ![LHS structure with Troc] U.S. Pat. No. 6,492,529 | N/A | GP1 | I | 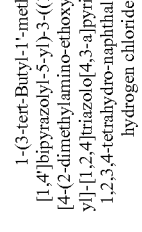<br>HCl<br>1-(3-tert-Butyl-1'-methyl-1'H-[1,4']bipyrazolyl-5-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt | (d₆-DMSO): 1.24 (9H, s), 1.72-1.92 (3H, m), 1.92-2.17 (5H, m), 2.54 (1H, s), 2.80 (6H, s), 3.01-3.11 (2H, m), 3.25-3.30 (1H, m), 3.36-3.45 (2H, m), 3.62-3.70 (1H, m), 3.78 (2H, t, J 5.3 Hz), 3.87 (3H, s), 4.80-4.88 (1H, m), 5.57 (1H, t, J 4.4 Hz), 6.26 (1H, s), 7.17 (2H, dd, J 9.8, 2.0 Hz), 7.27-7.33 (1H, m), 7.33-7.37 (2H, m), 7.38-7.42 (1H, m), 7.62 (2H, t, J 4.5 Hz), 7.70 (1H, d, J 1.7 Hz), 8.02 (1H, s), 8.05 (1H, s), 9.48 (1H, br s) | (Method 5): Rt 3.10 mins, m/z 696 [MH⁺]. |

| Example No. | LHS | Amine | General method | Intermediate Used | Example Structure | NMR (400 MHz) δ | LCMS |
|---|---|---|---|---|---|---|---|
| 25 | 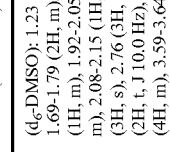WO206/091671 | N/A | GP1 | I | 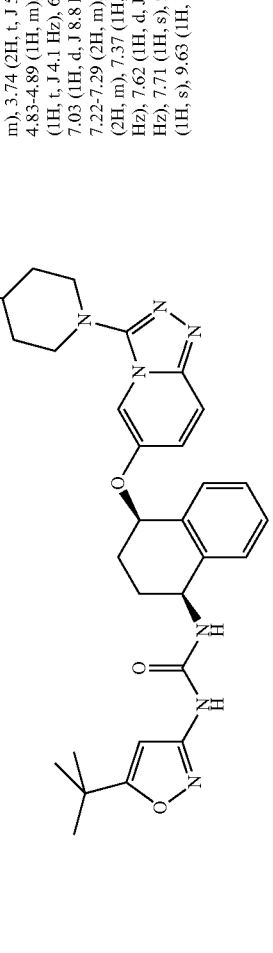HCl<br>1-(5-tert-Butyl-isoxazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt | (d$_6$-DMSO): 1.23 (9H, s), 1.69-1.79 (2H, m), 1.80-1.90 (1H, m), 1.92-2.05 (4H, m), 2.08-2.15 (1H, m), 2.75 (3H, s), 2.76 (3H, s), 3.02 (2H, t, J 10.0 Hz), 3.22-3.34 (4H, m), 3.59-3.64 (1H, m), 3.74 (2H, t, J 5.1 Hz), 4.83-4.89 (1H, m), 5.55 (1H, t, J 4.1 Hz), 6.35 (1H, s), 7.03 (1H, d, J 8.8 Hz), 7.22-7.29 (2H, m), 7.32-7.34 (2H, m), 7.37 (1H, d, J 7.7 Hz), 7.62 (1H, d, J 10.1 Hz), 7.71 (1H, s), 9.33 (1H, s), 9.63 (1H, br s) | (Method 5): Rt 3.40 mins, m/z 617 [MH$^+$]. |

| Example No. | LHS | Amine | General method | Intermediate Used | Example Structure | NMR (400 MHz) δ | LCMS |
|---|---|---|---|---|---|---|---|
| 26 | Intermediate 23 | N/A | GP1 | I | 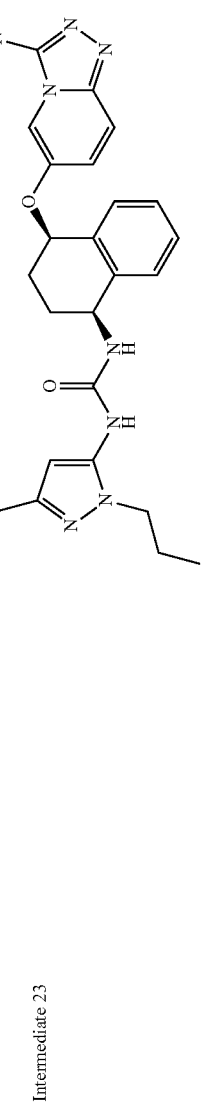<br>HCl<br>1-(5-tert-Butyl-2-propyl-2H-pyrazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt | (d$_6$-DMSO): 0.80 (3H, t, J 7.4 Hz), 1.16 (9H, s), 1.64 (2H, sext., J 7.4 Hz), 1.69-2.15 (8H, m), 2.75 (3H, s), 2.76 (3H, s), 3.00-3.06 (2H, m), 3.23-3.91 (4H, m), 3.59-3.65 (1H, m), 3.74 (2H, t, J 5.1 Hz), 3.81 (2H, t, J 7.4 Hz), 4.79-4.85 (1H, m), 5.56 (1H, t, J 4.3 Hz), 6.00 (1H, s), 7.04 (1H, d, J 8.7 Hz), 7.23-7.28 (2H, m), 7.33-7.37 (3H, m), 7.63 (1H, d, J 10.2 Hz), 7.73 (1H, d, J 1.2 Hz), 8.45 (1H, s), 9.59 (1H, br s). | (Method 5): Rt 3.30 mins, m/z 658 [MH$^+$]. |

| Example No. | LHS | Amine | General method | Intermediate Used | Example Structure | NMR (400 MHz) δ | LCMS |
|---|---|---|---|---|---|---|---|
| 27 | Intermediate 22 | N/A | GP1 | I | 1-[5-tert-Butyl-2-(2-methoxy-ethyl)-2H-pyrazol-3-yl]-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt HCl | (d$_6$-DMSO): 1.16 (9H, s), 1.69-1.79 (2H, m), 1.81-2.06 (5H, m), 2.08-2.16 (1H, m), 2.73 (6H, s), 2.98-3.04 (2H, m), 3.17-3.22 (5H, m), 3.34-3.38 (2H, m), 3.55-3.64 (3H, m), 3.72 (2H, t, J 5.1 Hz), 4.00 (2H, t, J 6.0 Hz), 4.79-4.84 (1H, m), 5.53 (1H, t, J 4.3 Hz), 6.00 (1H, s), 7.06 (1H, d, J 8.7 Hz), 7.14 (1H, dd, J 2.0, 9.8 Hz), 7.24-7.28 (1H, m), 7.31-7.37 (3H, m), 7.58 (1H, d, J 10.0 Hz), 7.66 (1H, d, J 1.8 Hz), 8.25 (1H, s), 9.55 (1H, br s). | (Method 5): Rt 3.22 mins, m/z 674 [MH$^+$]. |

| Example No. | LHS | Amine | General method | Intermediate Used | Example Structure | NMR (400 MHz) δ | LCMS |
|---|---|---|---|---|---|---|---|
| 28 | (structure from US2004/192653: tert-butyl-pyrazole with NHTroc) | 2-Methylamino-ethanol | GP1, GP2 | J | 1-(5-tert-Butyl-2-methyl-2H-pyrazol-3-yl)-3-[(1S,4R)-4-[3-((S)-3-{[(2-hydroxy-ethyl)-methyl-amino]-methyl}-piperidin-1-yl)-[1,2,4]triazolo[4,3-a]pyridin-6-yloxy]-1,2,3,4-tetrahydro-naphthalen-1-yl]-urea hydrogen chloride salt · HCl | (d₆-DMSO): 1.21 (9H, s), 1.79-2.22 (8H, m), 2.39 (1H, m), 2.80-2.83 (4H, m), 2.85-2.90 (1H, m), 2.95-3.04 (2H, m), 3.07-3.35 (3H, m, partially obscured by water), 3.61 (3H, s), 3.70 (1H, m), 3.75 (2H, s), 4.88 (1H, t, J 5.0 Hz), 5.69 (1H, m), 6.06 (1H, s), 7.10 (1H, d, J 8.5 Hz), 7.29-7.33 (1H, m), 7.37-7.48 (4H, m), 7.78 (1H, d, J 9.9 Hz), 7.91 (1H, d, J 5.8 Hz), 8.65 (1H, br s), 9.50 (1H, br s). | (Method 5): Rt 2.98 mins, m/z 630 [MH⁺]. |

| Example No. | LHS | Amine | General method | Intermediate Used | Example Structure | NMR (400 MHz) δ | LCMS |
|---|---|---|---|---|---|---|---|
| 29 | US2004/192653 | Dimethylamine | GP1, GP2 | J | 1-(5-tert-Butyl-2-methyl-2H-pyrazol-3-yl)-3-{(1S,4R)-4-[3-((S)-3-dimethylaminomethyl-piperidin-1-yl)-[1,2,4]triazolo[4,3-a]pyridin-6-yloxy]-1,2,3,4-tetrahydro-naphthalen-1-yl}-urea hydrogen chloride salt HCl | (d₆-DMSO): 1.23 (9H, s), 1.77-2.24 (8H, m), 2.37 (1H, m), 2.75-2.92 (8H, m), 2.99-3.74 (7H, m, partially obscured by water), 4.90 (1H, m), 5.81 (1H, t, J 4.1 Hz), 6.14 (1H, s), 7.30-7.34 (2H, m), 7.37-7.42 (2H, m), 7.47 (1H, d, 7.6 Hz), 7.70 (1H, m), 7.87-7.91 (1H, m), 8.07 (1H, s), 9.09 (1H, br s), 10.22 (1H, br s). | (Method 5): Rt 3.01 mins, m/z 600 [MH⁺]. |
| 30 | US2004/192653 | (2-Methoxyethyl)-methylamine | GP1, GP2 | 14e | 1-(5-tert-Butyl-2-methyl-2H-pyrazol-3-yl)-3-{(1S,4R)-4-[3-(4-{[(2-methoxyethyl)-methyl-amino]-methyl}-piperidin-1-yl)-[1,2,4]triazolo[4,3-a]pyridin-6-yloxy]-1,2,3,4-tetrahydro-naphthalen-1-yl}-urea | (d₆-DMSO): 1.20 (9H, s), 1.31-1.46 (2H, m), 1.65-1.75 (1H, m), 1.86-2.17 (4H, m), 2.20 (3H, s), 2.22-2.27 (2H, m), 2.86-2.97 (3H, m), 3.23 (3H, s), 3.29-3.47 (5H, m, obstructed by water), 3.57 (3H, s), 4.82-4.90 (1H, m), 5.55-5.60 (1H, m), 6.02 (1H, s), 6.92 (1H, d, J 8.69 Hz), 7.18 (1H, dd, J 1.96, 9.78 Hz), 7.27-7.33 (1H, m), 7.34-7.42 (3H, m), 7.59-7.67 (2H, m), 8.28 (1H, s). | (Method 5): Rt 3.02 mins, m/z 644.5 [MH⁺]. |

| Example No. | LHS | Amine | General method | Intermediate Used | Example Structure | NMR (400 MHz) δ | LCMS |
|---|---|---|---|---|---|---|---|
| 31 | US20041/92653 (Troc-protected tert-butyl-methylpyrazol-amine) | 2-Methylamino-ethanol | GP1, GP2 | 14e | 1-(5-tert-Butyl-2-methyl-2H-pyrazol-3-yl)-3-{(1S,4R)-4-[3-(4-{[(2-hydroxy-ethyl)-methyl-amino]-methyl}-piperidin-1-yl)-[1,2,4]triazolo[4,3-a]pyridin-6-yloxy]-1,2,3,4-tetrahydro-naphthalen-1-yl}-urea hydrogen chloride salt HCl | (d$_6$-DMSO): 1.20 (9H, s), 1.45-1.64 (2H, m), 1.75-2.22 (7H, m), 2.27-2.90 (2H, m), 2.92-3.07 (3H, m), 3.08-3.25 (2H, m), 3.22-3.38 (2H, m, obstructed by water), 3.40-3.53 (2H, m), 3.58 (3H, s), 3.70-3.83 (2H, m), 4.82-4.91 (1H, m), 5.34 (1H, bs), 5.54-5.60 (1H, m), 6.02 (1H, s), 6.97-7.04 (1H, m), 7.20 (1H, dd, J 2.37, 9.89 Hz), 7.24-7.44 (4H, m), 7.34 (1H, d, J 9.89 Hz), 7.67-7.70 (1H, m), 8.44 (1H, bs). | (Method 5): Rt 2.88 mins, m/z 630.4 [MH$^+$]. |

| Example No. | LHS | Amine | General method | Intermediate Used | Example Structure | NMR (400 MHz) δ | LCMS |
|---|---|---|---|---|---|---|---|
| 32 | US2004/192653 (pyrazole with NHTroc, tert-butyl, N-methyl) | [1,4]Oxazepane | GP1, GP2 | 14e | 1-(5-tert-Butyl-2-methyl-2H-pyrazol-3-yl)-3-{(1S,4R)-4-[3-(4-[1,4]oxazepan-4-ylmethyl-piperidin-1-yl)-[1,2,4]triazolo[4,3-a]pyridin-6-yloxy]-1,2,3,4-tetrahydro-naphthalen-1-yl}-urea hydrogen chloride salt | (d$_6$-DMSO): 1.20 (9H, s), 1.46-1.64 (2H, m), 1.82-2.28 (9H, m), 2.91-3.05 (2H, m), 3.09-3.33 (4H, m, obstructed by water), 3.41-3.60 (4H, m), 3.58 (3H, s), 3.66-3.93 (4H, m), 4.82-4.91 (1H, m), 5.53-5.59 (1H, m), 6.02 (1H, s), 6.98(1H, d, J 8.92 Hz), 7.20 (1H, dd, J 1.82, 9.69 Hz), 7.28-7.34 (1H, m), 7.35-7.44 (3H, m), 7.64 (1H, d, J 9.69 Hz), 7.68 (1H, bs), 8.42 (1H, bs). | (Method 5): Rt 2.98 mins, m/z 656.4 [MH$^+$]. |

| Example No. | LHS | Amine | General method | Intermediate Used | Example Structure | NMR (400 MHz) δ | LCMS |
|---|---|---|---|---|---|---|---|
| 33 | US2004/192653 (pyrazole with Troc-NH and tert-butyl, N-methyl) | 1-Methyl-piperazine | GP1, GP2 | 14e | <br>1-(5-tert-Butyl-2-methyl-2H-pyrazol-3-yl)-3-((1S,4R)-4-{3-[4-(4-methyl-piperazin-1-ylmethyl)-piperidin-1-yl]-[1,2,4]triazolo[4,3-a]pyridin-6-yloxy}-1,2,3,4-tetrahydro-naphthalen-1-yl)-urea hydrogen chloride salt | (d$_6$-DMSO): 1.20 (9H, s), 1.33-1.49 (2H, m), 1.70-2.31 (13H, m), 2.76 (3H, bs), 2.85-3.06 (6H, m), 3.36-3.50 (2H, m), 3.58 (3H, s), 4.82-4.92 (1H, m), 5.54-5.59 (1H, m), 6.02 (1H, s), 6.97 (1H, d, J 8.76 Hz), 7.19 (1H, dd, J 2.13, 9.95 Hz), 7.27-7.33 (1H, m), 7.35-7.43 (3H, m), 7.60-7.67 (2H, m), 8.39 (1H, bs). | (Method 5): Rt 3.59 mins m/z 655.5 [MH$^+$]. |

| Example No. | LHS | Amine | General method | Intermediate Used | Example Structure | NMR (400 MHz) δ | LCMS |
|---|---|---|---|---|---|---|---|
| 34 | ![LHS structure with tert-butyl pyrazole, Troc, N-methyl], US2004/192653 | 2-Methylamino-ethanol | GP1, GP2 | K | 1-(5-tert-Butyl-2-methyl-2H-pyrazol-3-yl)-3-{(1S,4R)-4-[3-((R)-3-{[(2-hydroxy-ethyl)-methyl-amino]-methyl}-piperidin-1-yl)-[1,2,4]triazolo[4,3-a]pyridin-6-yloxy]-1,2,3,4-tetrahydro-naphthalen-1-yl}-urea hydrogen chloride salt HCl | (CDCl₃): 1.28 (9H, s), 1.70-2.36 (9H, m), 2.59 (3H, br s), 2.67-3.04 (6H, m), 3.21 (1H, m), 3.49 (1H, d, J 10.4 Hz), 3.75 (5H, s), 5.14 (1H, m), 5.23 (1H, s), 6.14 (1H, s), 6.45 (1H, br s), 7.09 (1H, dd, J 9.9, 1.5 Hz), 7.20 (2H, d, J 4.1 Hz), 7.32 (1H, m), 7.40 (1H, s), 7.51-7.56 (2H, m), 7.61 (1H, br s). | (Method 5): Rt 2.98 mins, m/z 630 [MH⁺]. |
| 35 | Intermediate 22 | Dimethyl-amine | GP1, GP2 | 14e | 1-[5-tert-Butyl-2-(2-methoxy-ethyl)-2H-pyrazol-3-yl]-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea | (CDCl₃): 1.27 (9H, s), 1.61-1.74 (2H, m), 1.98-2.26 (5H, m), 2.27-2.36 (1H, m), 2.80 (6H, br s), 2.89 (2H, br s), 3.03-3.16 (2H, m), 3.31 (3H, s), 3.36-3.44 (1H, m), 3.48-3.56 (1H, m), 3.70 (2H, t, J 4.8 Hz), 4.21-4.27 (2H, m), 5.09-5.17 (1H, m), 5.22 (1H, t, J 3.6 Hz), 5.48-5.54 (1H, m), 6.08 (1H, dd, J 10.0, 1.9 Hz), 7.03 (1H, m), 7.21-7.30 (2H, m), 7.37 (1H, dt, J 7.9, 1.7 Hz), 7.46 (1H, s), 7.51 (1H, d, J 8.1 Hz), 7.58 (1H, d, J 9.9 Hz) plus 2 protons obscured by solvent signals | (Method 5): Rt 3.11 mins, m/z 644 [MH⁺]. |

| Example No. | LHS | Amine | General method | Intermediate Used | Example Structure | NMR (400 MHz) δ | LCMS |
|---|---|---|---|---|---|---|---|
| 36 | Intermediate 24 | Dimethylamine | GP1, GP2 | 14e | 1-(5-tert-Butyl-2-ethyl-2H-pyrazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 1.21 (9H, s), 1.26 (3H, t, J 7.1 Hz), 1.33-1.48 (2H, m), 1.66-1.76 (1H, m), 1.76-1.84 (2H, m), 1.86-2.00 (2H, m), 2.03-2.17 (4H, m), 2.18 (6H, s), 2.93 (2H, qd, J 10.2, 2.3 Hz), 3.42 (2H, m), 3.91 (2H, q, J 7.2 Hz), 4.82-4.90 (1H, m), 5.57 (1H, t, J 4.5 Hz), 6.03 (1H, s), 6.91 (1H, d, J 8.6 Hz), 7.18 (1H, dd, J 9.9, 2.2 Hz), 7.27-7.32 (1H, m), 7.35-7.42 (3H, m), 7.62 (1H, d, J 9.9 Hz), 7.65 (1H, d, J 6.5 Hz), 8.19 (1H, s), 8.22 (1H, s). | (Method 5): Rt 3.0 mins, m/z 614 [MH$^+$]. |

| Example No. | LHS | Amine | General method | Intermediate Used | Example Structure | NMR (400 MHz) δ | LCMS |
|---|---|---|---|---|---|---|---|
| 37 | WO2013083604 (structure with tert-butyl, methoxy, methanesulfonamide, NHTroc) | Dimethylamine | GP1, GP2 | 14e | N-[5-tert-Butyl-3-(3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-ureido)-2-methoxyphenyl]methanesulfonamide hydrogen chloride salt · HCl | (d$_6$-DMSO): 1.25 (9H, s), 1.46-1.53 (2H, m), 1.81-1.93 (4H, m), 1.99-2.17 (3H, m), 2.49-2.60 (8H, m, partially obscured by DMSO), 2.94-3.02 (2H, m), 3.05 (3H, s), 3.46 (2H, t, J 11.2 Hz), 3.69 (3H, s), 4.89-4.94 (1H, m), 5.59 (1H, t, J 4.4 Hz), 6.93 (1H, d, J 2.3 Hz), 7.19 (1H, dd, J 2.1, 9.8 Hz), 7.31 (1H, td, J 7.3, 1.5 Hz), 7.36-7.43 (4H, m), 7.63 (1H, d, J 9.8 Hz), 7.68 (1H, d, J 11.4 Hz), 8.08 (1H, s), 8.19 (1H, d, J 2.3 Hz), 9.02 (1H, s). | (Method 5): Rt 3.35 mins, m/z 719 [MH$^+$]. |

Example 38

1-(5-tert-Butyl-2-methyl-2H-pyrazol-3-yl)-3-{(1S, 4R)-4-[3-((2S,4S)-4-dimethylamino-1-methyl-pyrrolidin-2-yl)-[1,2,4]triazolo[4,3-a]pyridin-6-yloxy]-1, 2,3,4-tetrahydro-naphthalen-1-yl}-urea hydrochloride salt

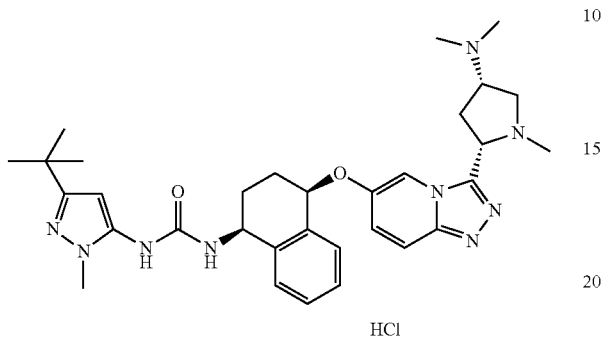

a. (2S,4S)-4-Dimethylamino-1-methyl-pyrrolidine-2-carboxylic acid (Intermediate 38a)

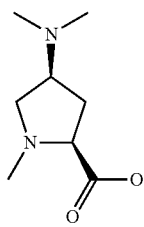

A solution of 1-methyl-4-amino-L-proline carboxylic acid (5.0 g, 34.2 mmol) in trifluoroethanol (40 mL) was treated with paraformaldeyde (5.13 g, 171 mmol). The reaction mixture was stirred for 15 min. at RT and NaBH₄ was added to the mixture. The reaction mixture was then heated for 2 hours at 90° C. The reaction was quenched with MeOH and the volatiles were evaporated to dryness under reduced pressure, affording the title compound as an off white foam that was used without further purification (6.0 g, 99%). LCMS (Method 3): Rt 0.43, m/z 173[MH⁻].

b. (2S,4S)-4-Dimethylamino-1-methyl-pyrrolidine-2-carboxylic acid N'-(5-fluoro-pyridin-2-yl)-hydrazide (Intermediate 38b)

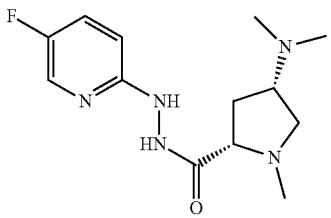 [SMILES: CN(C)[C@H]1C[C@@H](C(=O)NNc2ccc(F)cn2)N(C)C1]

A solution of Intermediate 38a (5.95 g, 34.2 mmol) in DCM (60 mL) was treated with EDCI (7.87 g, 34.2 mmol), HOBt (0.462 g, 41.0 mmol) and (5-fluoro-pyridin-2-yl)-hy-drazine (4.35g g, 34.2 mmol) and the solution was stirred at RT for 16 hours. The reaction mixture was partitioned between H₂O (50 mL) and DCM (40 mL) and the phases were separated. The organic phase was washed with sat. bicarbonate solution and the brine. The volatiles were concentrated in vacuo and the resultant residue was purified by FCC using 0-10% MeOH in DCM to afford the title compound (1.74 g, 20%). LCMS (Method 3): Rt 0.44 min, m/z 282 [MH⁺].

c. [(3S,5S)-5-(6-Fluoro-[1,2,4]triazolo[4,3-a]pyridin-3-yl)-1-methyl-pyrrolidin-3-yl]-dimethyl-amine (Intermediate 38c)

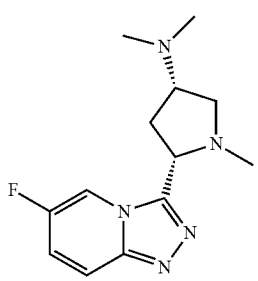 [SMILES: CN(C)[C@H]1C[C@@H](c2nnc3ccc(F)cn23)N(C)C1]

A solution of Intermediate 38b (1.73 g, 6.15 mmol) in THF (40 mL) was treated with triphenyl phospine (3.22 g, 12.3 mmol) and TEA (3.43 mL, 24.6 mmol). Hexachloroethane (2.91 g, 12.3 mmol) was added to the solution portion wise over a period of 5 minutes. The reaction mixture was heated at 60° C. for 16 hours. The reaction mixture was cooled down, treated with acetone to precipitate the triethylammonium chloride, which was then filtered; the filter cake was washed abundantly with acetone and the solvent was evaporated under reduced pressure. The residue was purified by SCX-2 cartridge eluting with DCM (40 mL), MeOH (40 mL) and 2M NH₃ in MeOH (40 mL). The product containing fractions were evaporated under reduced pressure to give the title compound as a brown oil (1.3 g, 80%). ¹H NMR (300 MHz, d6-DMSO): 201-2.13 (1H, m), 2.2 (3H, s), 2.29 (6H, s), 2.31-2.33 (1H, m), 2.34-2.39 (1H, m), 2.51-2.61 (1H, m), 2.88-2.98 (1H, m), 3.31-3.39 (1H, dd), 3.50 (1H, s), 4.17-4.27 (1H, m), 7.14-7.24 (1H, m), 7.67-7.77 (1H, m), 9.00-9.07 (1H, m).

d. {(3S,5S)-5-[6-((1R,4S)-4-Amino-1,2,3,4-tetrahydro-naphthalen-1-yloxy)-[1,2,4]triazolo[4,3-a]pyridin-3-yl]-1-methyl-pyrrolidin-3-yl}-dimethyl-amine (Intermediate 38d)

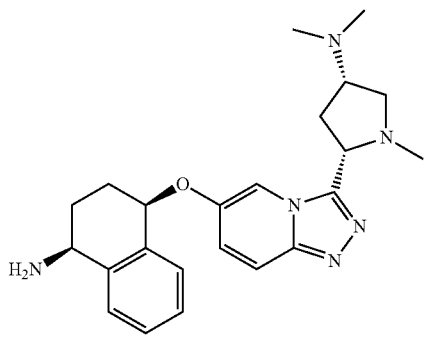 [SMILES: CN(C)[C@H]1C[C@@H](c2nnc3ccc(O[C@@H]4CC[C@H](N)c5ccccc54)cn23)N(C)C1]

A suspension of sodium hydride (60% dispersion in oil, 548 mg, 14.6 mmol) in dry DMF (10.0 mL) under nitrogen was treated with Intermediate 1 (800 mg, 4.9 mmol) and the mixture was stirred for 20 min. Intermediate 38c (1.28 g, 4.6 mmol) was added and the mixture was stirred at RT for 4 hours then quenched with MeOH. The mixture was further diluted with MeOH and applied to a pre-conditioned (MeOH) SCX-2 cartridge (25 g). The cartridge was eluted with MeOH then 2M NH$_3$ in MeOH. The relevant product containing fractions were combined and concentrated in vacuo to give the title compound as a dark brown oil (1.8 g, 86%). LCMS (Method 3): Rt 0.6, m/z 407 [MH$^+$].

e. 1-(5-tert-Butyl-2-methyl-2H-pyrazol-3-yl)-3-{(1S, 4R)-4-[3-((2S,4S)-4-dimethylamino-1-methyl-pyrrolidin-2-yl)-[1,2,4]triazolo[4,3-a]pyridin-6-yloxy]-1,2,3,4-tetrahydro-naphthalen-1-yl}-urea hydrochloride salt (Example 38)

(5-Tert-butyl-2-methyl-2H-pyrazol-3-yl)-carbamic acid 2,2,2-trichloro-ethyl ester (US2004/0192653, which is incorporated herein by reference in its entirety; 242 mg, 0.74 mmol) was treated with a solution of Intermediate 38d (300 mg, 0.74 mmol) in 1,4-dioxane (5 mL) then DIPEA (185 µL, 1.1 mmol) was added. The mixture was stirred at 50° C. overnight. The mixture was evaporated in vacuo and the residue purified by HPLC (Method 6, 20-40% MeCN in H$_2$O, 0.1% HCO$_2$H over 30 min) to give a colourless glass that was dissolved in MeCN and treated with 1N HCl (550 µL, 1 eq.). The volatiles were evaporated to drieness under reduced pressure affording a colourless glass that upon trituration with ether gave a solid. The solid was collected by filtration, washed with ether and dried at 50° C. in vacuo to give the title compound as an off white solid (346 mg, 74%). LCMS (Method 5): Rt 3.01 min, m/z 586.4 [MH$^+$]. $^1$H NMR (400 MHz, d6-DMSO): 1.20 (9H, s), 1.81-2.15 (5H, m), 2.16-2.24 (2H, bs), 2.42-2.52 (4H, br s, partially obscured by DMSO), 2.74-2.80 (6H, s), 3.45-3.53 (2H, m), 3.56 (3H, s), 3.97-4.06 (1H, m), 4.79-4.88 (1H, m), 5.54 (1H, t, J 4.3 Hz), 6.00 (1H, s), 7.08 (1H, d, J 8.4 Hz), 7.22-7.27 (1H, m), 7.33-7.39 (4H, m), 7.77 (1H, d, J 9.3 Hz), 8.45 (1H, bs), 8.60 (1H, s).

Example 39

1-(5-tert-Butyl-2-methyl-2H-pyrazol-3-yl)-3-{(1S,4R)-4-[3-(1,4-dimethyl-1,4,9-triaza-spiro[5.5]undec-9-yl)-[1,2,4]triazolo[4,3-a]pyridin-6-yloxy]-1,2,3,4-tetrahydro-naphthalen-1-yl}-urea hydrochloride salt

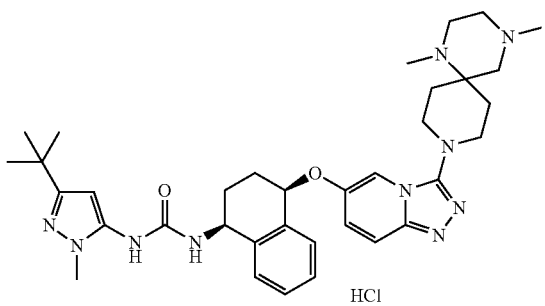 [SMILES: CN1CCN(C)C2(CCN(c3nnc4ccc(O[C@@H]5CC[C@H](NC(=O)Nc6cc(C(C)(C)C)nn6C)c6ccccc65)cn34)CC2)C1 ; Cl]

a. 9-(6-Fluoro-[1,2,4]triazolo[4,3-a]pyridin-3-yl)-1,4-dimethyl-1,4,9-triaza-spiro[5.5]undecane (Intermediate 39a)

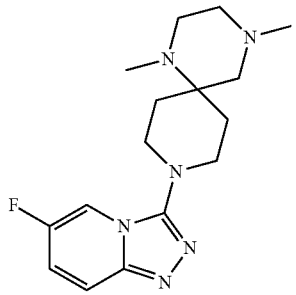 [SMILES: CN1CCN(C)C2(CCN(c3nnc4ccc(F)cn34)CC2)C1]

A mixture of Intermediate Ia (713 mg, 3.30 mmol), 1,4-Dimethyl-1,4,9-triaza-spiro[5.5]undecane (2.93g, 10.0 mmol) and DIPEA (6.1 mL, 35.0 mmol) in DMA (6 mL), under nitrogen was stirred at RT for 5 min, then treated with microwave irradiation at 170° C. for 6 h. The RM was concentrated in vacuo and the residue was purified by FCC, using 0-10% MeOH in DCM, then 0-20% [2M NH$_3$ in MeOH] in DCM to give a dark brown gum. This was re-purified by FCC, using 0-20% [2M NH$_3$ in MeOH] in DCM to afford the title compound (520 mg, 50%), as a brown gum. LCMS (Method 3): Rt 0.38/0.42 min, m/z 319. [MH$^+$].

b. (1S,4R)-4-[3-(1,4-Dimethyl-1,4,9-triazo-spiro[5 0.5]undec-9-yl)-[1,2,4]triazolo[4,3-a]pyridin-6-yloxy]-1,2,3,4-tetrahydro-naphthalen-1-ylamine (Intermediate 39b)

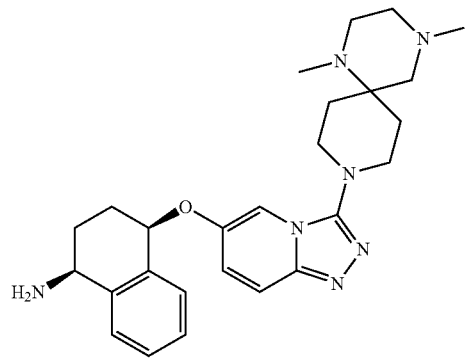 [SMILES: CN1CCN(C)C2(CCN(c3nnc4ccc(O[C@@H]5CC[C@H](N)c6ccccc65)cn34)CC2)C1]

Sodium hydride (200 mg, 5.0 mmol) was added to a mixture of Intermediate 1 (269 mg, 1.65 mmol) in anhydrous DMF (3 mL) and the RM was stirred at RT under an argon atmosphere for 30 min. Intermediate 39a (515 mg, 1.62 mmol) was added and the RM was stirred at RT for 22.5 h. The reaction mixture was diluted with water (10 mL) and extracted with DCM (5×20 mL). The combined organic layers were passed through a phase separator and concentrated in vacuo. The resultant residue was purified by FCC, using 0-22% [2M NH$_3$ in MeOH] in DCM to afford the title compound (425 mg, 57%). LCMS (Method 3): Rt 0.37/0.41 min, m/z 462. [MH$^+$].

c. 1-(5-tert-Butyl-2-methyl-2H-pyrazol-3-yl)-3-{(1S,4R)-4-[3-(1,4-dimethyl-1,4,9-triaza-spiro[5.5]undec-9-yl)-[1,2,4]triazolo[4,3-a]pyridin-6-yloxy]-1,2,3,4-tetrahydro-naphthalen-1-yl}-urea hydrochloride salt (Example 39)

A mixture of (5-tert-Butyl-2-methyl-2H-pyrazol-3-yl)-carbamic acid 2,2,2-trichloro-ethyl ester (US2004/192653, which is incorporated herein by reference in its entirety) (325 mg, 0.99 mmol), Intermediate 39b (420 mg, 0.90 mmol) and DIPEA (261 µL, 1.50 mmol) in 2-methyl-THF (4 mL) was stirred at 60° C. for 16.5 h and at 65° C. for 3 h. The volatiles were concentrated in vacuo and the resultant residue was purified by FCC, using 0-20% [2M $NH_3$ in MeOH] in DCM to give a pale orange foam (403 mg, 70%). This was purified by MDAP to afford the title compound, monoformic acid salt (239 mg, 38%) as a white solid. This was dissolved in MeCN and water, treated with 1M HCl (0.194 µL, 0.194 mmol) and freeze-dried to afford the title compound, monohydrogen chloride salt (121 mg, 20%), as a white solid. LCMS (Method 5): Rt 2.86 min, m/z 641.4[MH$^+$]. $^1$H NMR (400 MHz, DMSO): 8.53 (1H, s), 7.75 (1H, s), 7.66 (1H, d, J 9.62 Hz), 7.45-7.34 (3H, m), 7.34-7.22 (2H, m), 7.05 (1H, d, J 8.55 Hz), 6.03 (1H, s), 5.62-5.56 (1H, m), 4.92-4.83 (1H, m), 3.59 (3H, s), 3.48-3.09 (10H, m, obscured by water), 2.93-2.64 (4H, m), 2.47-1.84 (10H, m), 1.20 (9H, s).

Biological Assays.
P38alpha Enzyme Inhibition Assay.

The inhibitory activity of compounds was determined using an Alphascreen® (Perkin Elmer) based kinase activity assay. Kinase reactions consisted of 25 mM HEPES pH 7.5, 10 mM $MgCl_2$, 100 µM $Na_3VO_4$, 2 mM DTT, 0.05 mg/ml Tween 20, 100 pM p38alpha (Invitrogen, PV3304), 1% DMSO and 0.3 µg/ml ATF-2 fusion protein (New England Biolabs, 9224). Compounds were incubated under these conditions for 2 hours, at 25° C., prior to the initiation of the kinase activity by the addition of the 250 µM ATP. Reaction volumes were 20 uL. After 1 hr at 25° C. reactions were stopped by the adding 10 uL of 25 mM HEPES pH 7.5 containing 62.5 mM EDTA, 0.05% Triton X-100, 10% BSA and 0.83ng/uL anti-phospho-ATF2 antibody (Abcam, ab28812). Detection was performed by measuring luminescence following the addition of Alphascreen Donor beads (Perkin Elmer 6765300) and Protein A Alphascreen Acceptor beads (Perkin Elmer 6760137), both at a final concentration of 20 ug/ml. $IC_{50}$ values were determined from concentration-response curves.

The compounds of the invention being exemplified and tested show p38a binding potencies ($IC_{50}$ values) lower than 10 nM.

LPS-Stimulated PBMC TNFα Release Assay.

Peripheral Blood Mononuclear Cells (PBMCs) were isolated from healthy human volunteer blood using a standard density gradient centrifugation technique. Citrated blood was placed onto Histopaque™ and centrifuged. The PBMCs were removed from the density gradient interface and washed in phosphate buffered saline (PBS). The PBMCs were suspended in RPMI 1640 medium (without serum), dispensed into a 96-well plate and incubated at 37° C. for 3h in a humidified incubator. After incubation, the medium was replaced (with medium containing 1% foetal bovine serum) and the plate incubated at 37° C., for 1 h, in the presence of test compound or the appropriate vehicle. LPS (10 ng/ml), or an appropriate vehicle control, was then added to the cells and the plate returned to the incubator for 18h. Cell-free supernatants were removed and assayed for TNFα levels using an ELISA kit from R&D Systems.

A dose response curve to each test compound was performed and the effect of compound in each experiment was expressed as a percentage inhibition of the control TNFα release. Dose response curves were plotted and compound potency ($IC_{50}$) was determined. Compounds were tested in at least three separate experiments.

The compounds of the invention being exemplified and tested show p38α potencies ($IC_{50}$ values) lower than 10 nM.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound or pharmaceutically acceptable salt, which is a compound selected from the group consisting of 1-[1'-(2-dimethylamino-ethyl)-3-isopropyl-1'H-[1,4']bipyrazolyl-5-yl]-3-{(1S,4R)-4-[3-((2S,6R)-2,6-dimethyl-piperidin-1-yl)-[1,2,4]triazolo[4,3a]pyridin-6-yloxy]-1,2,3,4-tetrahydro-naphthalen-1-yl}-urea formate salt;

1-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-3-{3-isopropyl-1'-[2-(4-methyl-piperazin-1-yl)-ethyl]-1'H-[1,4']bipyrazolyl-5-yl}-urea formate salt;

1-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-3-[3-isopropyl-1'-(2-pyrrolidin-1-yl-ethyl)-1'H-[1,4']bipyrazolyl-5-yl]-urea formate salt;

1-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-3-[3-isopropyl-1'-(2-[1,4]oxazepan-4-yl-ethyl)-1'H-[1,4']bipyrazolyl-5-yl]-urea formate salt;

1-[1'-(2-dimethylamino-ethyl)-3-isopropyl-1'H-[1,3']bipyrazolyl-5-yl]-3-{(1S,4R)-4-[3-((2S,6R)-2,6-dimethyl-piperidin-1-yl)-[1,2,4]triazolo[4,3a]pyridin-6-yloxy]-1,2,3,4-tetrahydro-naphthalen-1-yl}-urea formate salt;

1-[1'-(2-dimethylamino-ethyl)-3-isopropyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[1'-(2-dimethylamino-ethyl)-3-ethyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[1'-(2-dimethylamino-ethyl)-3-ethyl-1'H-[1,4']bipyrazolyl-5-yl]-3-{(1S,4R)-4-[3-((2S,6R)-2,6-dimethyl-piperidin-1-yl)-[1,2,4]triazolo[4,3a]pyridin-6-yloxy]-1,2,3,4-tetrahydro-naphthalen-1-yl}-urea formate salt;

1-{2-[3-(2-dimethylamino-ethoxy)-phenyl]-5-methyl-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[1'-(2-azetidin-1-yl-ethyl)-3-tert-butyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-butyl-1'-[2-(3-dimethylamino-azetidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[3-(3-dimethylamino-azetidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-(5-tert-butyl-2-methyl-2H-pyrazol-3-yl)-3-((1S,4R)-4-{3-[2,6-dichloro-4-(4-methyl-piperazin-1-ylmethyl)-phenyl]-[1,2,4]triazolo[4,3-a]pyridin-6-yloxy}-1,2,3,4-tetrahydro-naphthalen-1-yl)-urea formate salt;

1-(5-tert-butyl-2-methyl-2H-pyrazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt;

1-(5-tert-butyl-isoxazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea;

1-(3-tert-butyl-1'-methyl-1'H-[1,4']bipyrazolyl-5-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt;

1-[3-tert-butyl-1'-(2-dimethylamino-ethyl)-1'H-[1,4']bipyrazolyl-5-yl]-3-{4-[3-((2S,6R)-2,6-dimethyl-piperidin-1-yl)-[1,2,4]triazolo[4,3-a]pyridin-6-yloxy]-cyclohexyl}-urea;

1-(5-tert-butyl)-2-p-tolyl-2H-pyrazol-3-yl)-3-{4-[3-((S)-2-methyl-piperidin-1-yl)-[1,2,4]triazolo[4,3-a]pyridin-6-yloxy]-cyclohexyl}-urea;

1-{5-tert-butyl-2-[3-(2-dimethylamino-ethoxy)-phenyl]-2H-pyrazol-3-yl}-3-{4-[3-((S)-2-methyl-piperidin-1-yl)-[1,2,4]triazolo[4,3-a]pyridin-6-yloxy]-cyclohexyl}-urea;

1-{5-(cyano-dimethyl-methyl)-2-[3-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl}-urea;

1-{5-(cyano-dimethyl-methyl)-2-[3-(2-dimethylamino-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea;

1-(5-tert-butyl-2-methyl-2H-pyrazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-[5-tert-butyl-2-(2-hydroxy-ethyl)-2H-pyrazol-3-yl]-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-(3-tert-butyl-1'-methyl-1'H-[1,4']bipyrazolyl-5-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-(5-tert-butyl-isoxazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-(5-tert-butyl-2-propyl-2H-pyrazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-[5-tert-butyl-2-(2-methoxy-ethyl)-2H-pyrazol-3-yl]-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-(5-tert-butyl-2-methyl-2H-pyrazol-3-yl)-3-{(1S,4R)-4-[3-((S)-3-{[(2-hydroxy-ethyl)-methyl-amino]-methyl}-piperidin-1-yl)-[1,2,4]triazolo[4,3-a]pyridin-6-yloxy]-1,2,3,4-tetrahydro-naphthalen-1-yl}-urea hydrogen chloride salt;

1-(5-tert-butyl-2-methyl-2H-pyrazol-3-yl)-3-{(1S,4R)-4-[3-((S)-3-dimethylaminomethyl-piperidin-1-yl)-[1,2,4]triazolo[4,3-a]pyridin-6-yloxy]-1,2,3,4-tetrahydro-naphthalen-1-yl}-urea hydrogen chloride salt;

1-(5-tert-butyl-2-methyl-2H-pyrazol-3-yl)-3-{(1S,4R)-4-[3-(4-{[(2-methoxy-ethyl)-methyl-amino]-methyl}-piperidin-1-yl)-[1,2,4]triazolo[4,3-a]pyridin-6-yloxy]-1,2,3,4-tetrahydro-naphthalen-1-yl}-urea;

1-(5-tert-butyl-2-methyl-2H-pyrazol-3-yl)-3-{(1S,4R)-4-[3-(4-{[(2-hydroxy-ethyl)-methyl-amino]-methyl}-piperidin-1-yl)-[1,2,4]triazolo[4,3-a]pyridin-6-yloxy]-1,2,3,4-tetrahydro-naphthalen-1-yl}-urea hydrogen chloride salt;

1-(5-tert-butyl-2-methyl-2H-pyrazol-3-yl)-3-{(1S,4R)-4-[3-(4-[1,4]oxazepan-4-ylmethyl-piperidin-1-yl)-[1,2,4]triazolo[4,3-a]pyridin-6-yloxy]-1,2,3,4-tetrahydro-naphthalen-1-yl}-urea hydrogen chloride salt;

1-(5-tert-butyl-2-methyl-2H-pyrazol-3-yl)-3-((1S,4R)-4-{3-[4-(4-methyl-piperazin-1-ylmethyl)-piperidin-1-yl]-[1,2,4]triazolo[4,3-a]pyridin-6-yloxy}-1,2,3,4-tetrahydro-naphthalen-1-yl)-urea hydrogen chloride salt;

1-(5-tert-butyl-2-methyl-2H-pyrazol-3-yl)-3-{(1S,4R)-4-[3-((R)-3-{[(2-hydroxy-ethyl)-methyl-amino]-methyl}-piperidin-1-yl)-[1,2,4]triazolo[4,3-a]pyridin-6-yloxy]-1,2,3,4-tetrahydro-naphthalen-1-yl}-urea hydrogen chloride salt;

1-[5-tert-butyl-2-(2-methoxy-ethyl)-2H-pyrazol-3-yl]-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea;

1-(5-tert-butyl-2-ethyl-2H-pyrazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-urea formate salt;

N-[5-tert-butyl-3-(3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1-yl}-ureido)-2-methoxyphenyl]methanesulfonamide hydrogen chloride salt;

1-(5-tert-butyl-2-methyl-2H-pyrazol-3-yl)-3-{(1S,4R)-4-[3-((2S,4S)-4-dimethylamino-1-methyl-pyrrolidin-2-yl)-[1,2,4]triazolo[4,3-a]pyridin-6-yloxy]-1,2,3,4-tetrahydro-naphthalen-1-yl}-urea hydrochloride salt;

1-(5-tert-butyl-2-methyl-2H-pyrazol-3-yl)-3-(1S,4R)-4-[3-(1,4-dimethyl-1,4,9-triaza-spiro[5.5]undec-9-yl)-[1,2,4]triazolo[4,3-a]pyridin-6-yloxy]-1,2,3,4-tetrahydro-naphthalen-1-yl-urea hydrochloride salt or a pharmaceutically acceptable salt of said compound.

2. A pharmaceutical composition, comprising a compound or pharmaceutically acceptable salt as claimed in claim 1 and one or more pharmaceutically acceptable carriers.

3. A method of treating chronic eosinophilic pneumonia, asthma, chronic obstructive pulmonary disease, adult respiratory distress syndrome, exacerbation of airway hyper-reactivity consequent to other drug therapy, or airway disease that is associated with pulmonary hypertension, said method comprising administering to a subject in need thereof an effective amount of a compound or pharmaceutically acceptable salt as claimed in claim 1.

4. A compound or pharmaceutically acceptable salt, which is a compound selected from the group consisting of 1-[1'-(2-dimethylamino-ethyl)-3-isopropyl-1'H-[1,4']bipyrazolyl-5-yl]-3-{(1S,4R)-4-[3-((2S,6R)-2,6-dimethyl-piperidin-1-yl)-[1,2,4]triazolo[4,3a]pyridin-6-yloxy]-1,2,3,4-tetrahydro-naphthalen-l-yl}-urea formate salt;

1-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-3-{3-isopropyl-1'-[2-(4-methyl-piperazin-1-yl)-ethyl]-1'H-[1,4']bipyrazolyl-5-yl}-urea formate salt;

1-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-3-[3-isopropyl-1'-(2-pyrrolidin-1-yl-ethyl)-1'H-[1,4']bipyrazolyl-5yl]-urea formate salt;

1-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-3-[3-isopropyl-1'-(2-[1,4]oxazepan-4-yl-ethyl)-1'H-[1,4']bipyrazolyl-5-yl]-urea formate salt;

1-[1'-(2-dimethylamino-ethyl)-3-isopropyl-1'H-[1,3']bipyrazolyl-5-yl]-3-{(1S,4R)-4-[3-((2S,6R)-2,6-dimethyl-piperidin-1-yl)-[1,2,4]triazolo[4,3a]pyridin-6-yloxy]-1,2,3,4-tetrahydro-naphthalen-1-yl}-urea formate salt;

1-[1'-(2-dimethylamino-ethyl)-3-isopropyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[1'-(2-dimethylamino-ethyl)-3-ethyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[1'(2-dimethylamino-ethyl)-3-ethyl-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{2-[3-(2-dimethylamino-ethoxy)-phenyl]-5-methyl-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[1'-(2-azetidin-1yl-ethyl)-3tert-butyl-1'H-[1,4']bipyrazolyl-5-yl]-3-{(1S,4R)-4-[3-((S)-(2-methyl-piperidin-1yl)-[1,2,4]triazolo[4,3-a]pyridin-6-yloxy]-1,2,3,4-tetrahydro-naphthalen-1-yl}-urea formate salt;

1-{3-tert-butyl-1'-[2-(3-dimethylamino-azetidin-1-yl)-ethyl]-1'H-[1,4']bipyrazolyl-5-yl}-3-{(1S,4,R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[3(3-dimethylamino-azetidin-1ylmethyl)-phenyl]-2H-pyrazol-3 -yl}-3-{(1S,4R)-4-[3((S)-2-methyl-pipiridin-1-yl)-[1,2,4]triazolo[4,3-a]pyridin-6-yloxy]-1,2,3,4-tetrahydro-naphthalen-1-yl}-urea formate salt;

1-(5-tert-butyl-2-methyl-2H-pyrazol-3-yl)-3-((1S,4R)-4-{3-[2,6-dichloro-4-(4-methyl-piperazin1-ylmethyl)-phenyl]-[1,2,4]triazolo[4,3-a]pyridin-6-yloxy}-1,2,3,4-tetrahydro-naphthalen-1-yl)-urea formate salt;

1-(5-tert-butyl-2methyl-2H-pyrazol-3-yl)-3-{(1S,4R)-4-[3-(4-dimethylaminomethyl-piperidin-1-yl)-[1,2,4]triazolo[4,3-a]pyridin-6-yloxy]-1,2,3,4-tetrahydro-naphthalen-1--yl}--urea formate salt;

1-(3tert-butyl-1'-methyl-1'H-[1,4']bipyrazolyl-5-yl)-3-{(1S,4R)-4-[3-(4-dimethylaminomethyl-piperidin-1yl)-[1,2,4]triazolo[4,3-a]pyridin-6yloxy]-1,2,3,4-tetrahydro-naphthalen-1yl}-urea formate salt;

1-{5-(cyano-dimethyl-methyl)-2-[3-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl}-urea;

1-{5-(cyano-dimethyl-methyl)-2-[3-(2-dimethylamino-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydronaphthalen-1-yl}-urea;

1-(5-tert-butyl-2-methyl-2H-pyrazol-3-yl)-3-((1S,4R)-4-{3-[4-(2-dimethylamino-ethoxy)-piperidin-1-yl]-[1,2,4]triazolo[4,3-a]pyridin-6-yloxy}-1,2,3,4-tetrahydro-naphthalen-1-yl)-urea hydrogen chloride salt;

1-[5-tert-butyl-2-(2-hydroxy-ethyl)-2H-pyrazol-3-yl]-3-((1S,4R)-4-{3-[4-(2-dimethylamino-ethoxy)-piperidin-1-yl]-[1,2,4]triazolo[4,3-a]pyridin-6-yloxy]-1,2,3,4-tetrahydro-naphthalen-1-yl)-urea hydrogen chloride salt;

1-(3-tert-butyl-1'-methyl-1'H-[1,4']bipyrazolyl-5-yl)-3-((1S,4R)-4-{3-[4-(2-dimethylamino-ethoxy)-piperidin-1-yl]-[1,2,4]triazolo[4,3-a]pyridin-6-yloxy]-1,2,3,4-tetrahydro-naphthalen-1-yl)-urea hydrogen chloride salt;

1-(5-tert-butyl-2-propyl-2H-pyrazol-3-yl)-3-((1S,4R)-4-{3-[4-(2-dimethylamino-ethoxy)-piperidin-1-yl]-[1,2,4]triazolo[4,3-a]pyridin-6-yloxyl-1,2,3,4-tetrahydronaphthalen-1-yl)-urea hydrogen chloride salt;

1-[5-tert-butyl-2-(2-methoxy-ethyl)-2H-pyrazol-3-yl]-3-((1S,4R)-4-{3-[4-(2-dimethylamino-ethoxy)-piperidin-1-yl]-[1,2,4]triazolo[4,3-a]pyridin-6-yloxy]-1,2,3,4-tetrahydro-naphthalen-1-yl)-urea hydrogen chloride salt;

1-(5-tert-butyl-2-methyl-2H-pyrazol-3-yl)-3-{(1S,4R)-4-[3-((S)-3-{[(2-hydroxy-ethyl)-methyl-amino]-methyl}-piperidin-1-yl)-[1,2,4]triazolo[4,3-a]pyridin-6-yloxy]-1,2,3,4-tetrahydro-naphthalen-1-yl}-urea hydrogen chloride salt;

1-(5-tert-butyl-2-methyl-2H-pyrazol-3-yl)-3-{(1S,4R)-4-[3-((S)-3-dimethylaminomethyl-piperidin-1-yl)-[1,2,4]triazolo[4,3-a]pyridin-6-yloxyl-1,2,3,4-tetrahydro-naphthalen-1-yl}-urea hydrogen chloride salt;

1-(5-tert-butyl-2-methyl-2H-pyrazol-3-yl)-3-{(1S,4R)-4-[3-(4-{[(2-methoxy-ethyl)-methyl-amino]-methyl}-piperidin-1-yl)-[1,2,4]triazolo[4,3-a]pyridin-6-yloxy]-1,2,3,4-tetrahydro-naphthalen-1-yl)-urea;

1-(5-tert-butyl-2-methyl-2H-pyrazol-3-yl)-3-{(1S,4R)-4-[3-(4-{[(2-hydroxy-ethyl)-methyl-amino]-methyl}-piperidin-1-yl)-[1,2,4]triazolo[4,3-a]pyridin-6-yloxy]-1,2,3,4-tetrahydro-naphthalen-1-yl}-urea hydrogen chloride salt;

1-(5-tert-butyl-2-methyl-2H-pyrazol-3-yl)-3-{(1S,4R)-4-[3-(4[1,4]oxazepan-4-ylmethyl-piperidin-1-yl)1,2,4]triazolo[4,3-a]pyridin-6-yloxy]-1,2,3,4-tetrahydro-naphthalen-1-yl}-urea hydrogen chloride salt;

1-(5-tert-butyl-2-methyl-2H-pyrazol-3-yl)-3((1S,4R)-4-{3-[4-(4-methyl-piperazin-1-ylmethyp-piperidin-1-yl]-[1,2,4]triazolo[4,3-a]pyridin-6-yloxyl]-1,2,3,4-tetrahydro-naphthalen-1-yl)-urea hydrogen chloride salt;

1-(5-tert-butyl-2-methyl-2H-pyrazol-3-yl)-3-{(1S,4R)-4-[3-((R)-3-{[(2-hydroxy-ethyl)-methyl-amino]-methyl}-piperidin-1-yl)-[1,2,4]triazolo[4,3-a]pyridin-6-yloxy]-1,2,3,4-tetrahydro-naphthalen-1-yl}-urea hydrogen chloride salt;

1-[5-tert-butyl-2-(2-methoxy-ethyl)-2H-pyrazol-3-yl]-3-{(1S,4R)-4-[3-(4-dimethylaminomethyl-piperidin-1-yl)-[1,2,4triazolo[4,3-a]pyridin-6-yloxy]-1,2,3,4-tetrahydro-naphthalen-1-yl}-urea;

1-(5-tert-butyl-2-ethyl-2H-pyrazol-3-yl)-3-{(1S,4R)-4-[3-(4-dimethylaminomethyl-piperidin-1-yl)-1,2,4]triazolo[4,3-a]pyridin-6-yloxy]-1,2,3,4-tetrahydro-naphthalen-1-yl}-urea formate salt;

1-(5-tert-butyl-2-methyl-2H-pyrazol-3-yl)-3-{(1S,4R)-4-[3-((2S,4S)-4-dimethylamino-1-methyl-pyrrolidin-2-yl)-[1,2,4]triazolo[4,3-a]pyridin-6-yloxy]-1,2,3,4-tetrahydro-naphthalen-1-yl}-urea hydrochloride salt;

1-(5-tert-butyl-2-methyl-2H-pyrazol-3-yl)-3-{(1S,4R)-4-[3-(1,4-dimethyl-1,4,9-triaza-spiro[5.5]undec-9-yl)1,2,4]triazolo[4,3-a]pyridin-6-yloxyl-1,2,3,4-tetrahydro-naphthalen-1-yl}-urea hydrochloride salt or a pharmaceutically acceptable salt of said compound.

5. A pharmaceutical composition, comprising a compound or pharmaceutically acceptable salt as claimed in claim 4 and one or more pharmaceutically acceptable carriers.

6. A method of treating chronic eosinophilic pneumonia, asthma, chronic obstructive pulmonary disease, adult respiratory distress syndrome, exacerbation of airway hyper-reactivity consequent to other drug therapy, or airway disease that is associated with pulmonary hypertension, said method comprising administering to a subject in need thereof an effective amount of a compound or pharmaceutically acceptable salt as claimed in claim 4.

* * * * *